US008257502B2

(12) United States Patent
Frohberg et al.

(10) Patent No.: US 8,257,502 B2
(45) Date of Patent: Sep. 4, 2012

(54) PLANTS WITH REDUCED ACTIVITY OF A STARCH PHOSPHORYLATING ENZYME

(75) Inventors: Claus Frohberg, Kleinmachnow (DE); Oliver Koetting, Zürich (CH); Gerhard Ritte, Potsdam (DE); Martin Steup, Berlin (DE)

(73) Assignee: Bayer Cropscience AG, Monheim Am Rhein (DE)

( * ) Notice: Subject to any disclaimer, the term of this patent is extended or adjusted under 35 U.S.C. 154(b) by 0 days.

(21) Appl. No.: 13/033,495

(22) Filed: Feb. 23, 2011

(65) Prior Publication Data
US 2011/0269195 A1 Nov. 3, 2011

Related U.S. Application Data

(62) Division of application No. 10/591,540, filed as application No. PCT/EP2005/002450 on Mar. 4, 2005, now Pat. No. 7,919,682.

(60) Provisional application No. 60/550,022, filed on Mar. 5, 2004.

(30) Foreign Application Priority Data

Mar. 5, 2004 (EP) .................................. 04090088
Mar. 29, 2004 (EP) .................................. 04090121
May 21, 2004 (EP) .................................. 04090203
Dec. 9, 2004 (EP) .................................. 04090484

(51) Int. Cl.
*C08B 31/06* (2006.01)
*C08B 30/00* (2006.01)
*C07H 11/04* (2006.01)
*C07K 14/415* (2006.01)

(52) U.S. Cl. ....... 127/32; 435/183; 435/320.1; 435/410; 435/468; 530/370; 530/372; 536/23.1; 536/23.2; 536/23.6; 800/278; 800/284; 800/295; 930/230

(58) Field of Classification Search .......................... None
See application file for complete search history.

(56) References Cited

U.S. PATENT DOCUMENTS 6,521,816 B1 * 2/2003 Frohberg ...................... 800/284
2006/0123505 A1 6/2006 Kikuchi et al.

FOREIGN PATENT DOCUMENTS

| WO | WO 96/27674 | 9/1996 |
| WO | WO 97/11188 | 3/1997 |
| WO | WO 00/77229 | 12/2000 |
| WO | WO 02/10210 | 2/2002 |
| WO | WO 02/22675 | 3/2002 |
| WO | WO 02/34923 | 5/2002 |
| WO | WO 2005/095632 | 10/2005 |

OTHER PUBLICATIONS

Alonso et al.; Genome-Wide Insertional Mutagenesis of Arabidopsis thaliana; Science, Aug. 1, 2003; vol. 301; pp. 653-657.

Baunsgaard et al.; A novel Isoform of Glucan, Water Dikinase Phosphorylates Pre-Phosphorylated α-glucans and is Involved in Starch Degradation in Arabidopsis; The Plant Journal, 2005, vol. 41, pp. 595-605; XP-002339143.
Blennow et al.; Starch molecular structure and phosphorylation investigated by a combined chromatographic and chemometric approach; Carbohydrate Polymers; 2000, vol. 41, pp. 163-174.
Blennow et al.; Starch phosphorylation: a new front line in starch research; Trends in Plant Science; Oct. 2002; vol. 7, No. 10; pp. 445-450.
Blennow et al.; The distribution of covalendy bound phosphate in the starch granule in relation to starch crystallinity; International Journal of Biological Macromolecules; 2000; vol. 27, pp. 211-218.
GenBank Accession No. AF312027 (Aug. 24, 2001).
GenBank Accession No. AR400184 (Dec. 18, 2003).
GenBank Accession No. AR400813 (Dec. 18, 2003).
GenBank Accession No. AR400815 (Dec. 18, 2003).
GenBank Accession No. AY027522 (Feb. 26, 2001).
GenBank Accession No. AY094062 (Jul. 23, 2003).
GenBank Accession No. Y09533 (Jul. 22, 2003).
GenPept Accession No. AAN93923 (Dec. 20, 2002).
GenPept Accession No. AAR61444 (Dec. 18, 2003).
GenPept Accession No. AAR61445 (Dec. 18, 2003).
GenPept Accession No. AAR61446 (Dec. 18, 2003).
GenPept Accession No. AR236165 (Dec. 20, 2002).
GenPept Accession No. B29959 (Jun. 18, 1999).
GenPept Accession No. S01446 (Jul. 21, 2000).
Jane et al., Phosphorus in Rice and Other Starches; Cereal Foods World, Nov.-Dec. 1996; vol. 41; No. 11; pp. 827-832.
Kötting et al., Identification of a Novel Enzyme Required for Starch Metabolism in Arabidopsis Leaves. The Phosphoglucan, Water Dikinase; Plant Physiology, Jan. 2005, vol. 137, pp. 242-252; XP-002339144.
Lorberth et al.; Inhibition of a starch-granule-bound protein leads to modified starch and repression of cold sweetening; Nature Biotechnology; May 1998; vol. 16, pp. 473-477; XP002111459.
Mikkelsen et al. (2004) "Functional characterization of α-glucan, water dikinase, the starch phosphorylating enzyme." *Biochem. J.* 377: 525-532.

(Continued)

*Primary Examiner* — Brent T Page
(74) *Attorney, Agent, or Firm* — Hunton & Williams, LLP

(57) ABSTRACT

The present invention relates to plant cells and plants, which are genetically modified, wherein the genetic modification leads to the reduction of the activity of a starch phosphorylating OK1 protein in comparison with corresponding wild type plant cells or wild type plants that have not been genetically modified. Furthermore, the present invention relates to means and methods for the manufacture of such plant cells and plants. Plant cells and plants of this type synthesise a modified starch. The present invention therefore also relates to the starch synthesised by the plant cells and plants according to the invention, methods for the manufacture of this starch, and the manufacture of starch derivatives of this modified starch, as well as flours containing starches according to the invention. Furthermore, the present invention relates to nucleic acid molecules, which are suitable for manufacturing plants according to the invention.

7 Claims, 6 Drawing Sheets

OTHER PUBLICATIONS

NCBI Sequence Viewer; Novel isoform of glucan, water dikinase phosphorylates pre-phosphorylated alpha-glucans and is involved in starch degradation in Arabidopsis; Mar. 1, 2005; AY747068.

Ritte et al. (2000) "Compartmentation of the Starch-Related R1 Protein in Higher Plants." *Starch/Stärke* 52: 179-185.

Ritte et al. (2003) "Determination of the starch-phosphorylating enzyme activity in plant extracts." *Planta* 216(5): 798-801.

Ritte et al., FEBS Letters, vol. 580, pp. 4872-4876 (2006).

Ritte et al.; The starch-related R1 protein is an α-glucan, water dikinase; PNAS; May 14, 2002; vol. 99; No. 10; pp. 7166-7171.

Sitohy et al.; Optimizing the Conditions for Starch Dry Phosphorylation with Sodium Mono-and Dihydrogen Orthophosphate under Heat and Vacuum; Starch/Starke; 2000; vol. 52; No. 4; pp. 95-100.

Tabata et al.; Studies on Starch Phosphate; Die Stärke/Starch; 1971; vol. 23, pp. 267-272.

UniProtKB/Swiss-Prot entry Q6ZY51 (Jun. 13, 2006).

UniProtKB/TrEMBL entry Q84T18 (Jun. 1, 2003).

Yu et. al.; The Arabidopsis sex1 Mutant is Defective in the R1 Protein, a General Regulator of Starch Degradation in Plants, and Not in the Chloroplast Hexose Transporter; The Plant Cell; Aug. 2001; vol. 13, pp. 1907-1918; XP002252059.

\* cited by examiner

Fig.: 3

WT             OK1 Mutant (SALK_110814)

SEQUENCE LISTING

```
<160> NUMBER OF SEQ ID NOS: 31

<210> SEQ ID NO 1
<211> LENGTH: 3591
<212> TYPE: DNA
<213> ORGANISM: Arabidopsis thaliana
<220> FEATURE:
<221> NAME/KEY: CDS
<222> LOCATION: (1)..(3591)
<223> OTHER INFORMATION:

<400> SEQUENCE: 1 atg gag agc att ggc agc cat tgt tgc agc tct cct ttc acc ttc atc        48
Met Glu Ser Ile Gly Ser His Cys Cys Ser Ser Pro Phe Thr Phe Ile
1               5                   10                  15 act aga aac tca tca tca tca ctt cct aga ctc gtt aac atc act cac        96
Thr Arg Asn Ser Ser Ser Ser Leu Pro Arg Leu Val Asn Ile Thr His
            20                  25                  30 aga gtt aat ctc agc cac caa tct cac cga ctc aga aac tcc aat tct       144
Arg Val Asn Leu Ser His Gln Ser His Arg Leu Arg Asn Ser Asn Ser
        35                  40                  45 cgt ctc act tgc act gct act tct tct acc att gag gaa caa cgg            192
Arg Leu Thr Cys Thr Ala Thr Ser Ser Ser Thr Ile Glu Glu Gln Arg
    50                  55                  60 aag aag aaa gat gga tca gga acg aaa gtg agg ttg aat gtg agg tta       240
Lys Lys Lys Asp Gly Ser Gly Thr Lys Val Arg Leu Asn Val Arg Leu
65                  70                  75                  80 gat cat caa gtt aat ttt ggt gac cat gtg gct atg ttt gga tca gct       288
Asp His Gln Val Asn Phe Gly Asp His Val Ala Met Phe Gly Ser Ala
                85                  90                  95 aaa gag att ggt tca tgg aaa aag aaa tcg cct ttg aat tgg agt gag       336
Lys Glu Ile Gly Ser Trp Lys Lys Lys Ser Pro Leu Asn Trp Ser Glu
            100                 105                 110 aat gga tgg gtt tgt gag ttg gaa ctt gac ggt ggt cag gtt ttg gag       384
```

```
                Asn Gly Trp Val Cys Glu Leu Glu Leu Asp Gly Gly Gln Val Leu Glu
                            115                 120                 125 tat aag ttt gtc att gtt aag aat gat ggt tca ctt tca tgg gaa tct        432
Tyr Lys Phe Val Ile Val Lys Asn Asp Gly Ser Leu Ser Trp Glu Ser
            130                 135                 140 ggt gat aat cgt gtc ctt aag gtt cca aat tct ggg aat ttt tct gtt        480
Gly Asp Asn Arg Val Leu Lys Val Pro Asn Ser Gly Asn Phe Ser Val
145                 150                 155                 160 gtt tgt cat tgg gat gct act aga gaa acc ctt gat ttg cct cag gag        528
Val Cys His Trp Asp Ala Thr Arg Glu Thr Leu Asp Leu Pro Gln Glu
                165                 170                 175 gtt ggt aat gat gat gat gtt ggt gat ggt ggg cat gag agg gat aat        576
Val Gly Asn Asp Asp Asp Val Gly Asp Gly Gly His Glu Arg Asp Asn
            180                 185                 190 cat gat gtt ggt gat gat aga gta gtg gga agt gaa aat ggt gcg cag        624
His Asp Val Gly Asp Asp Arg Val Val Gly Ser Glu Asn Gly Ala Gln
        195                 200                 205 ctt cag aag agt aca ttg ggt ggg caa tgg caa ggt aaa gat gcg tcc        672
Leu Gln Lys Ser Thr Leu Gly Gly Gln Trp Gln Gly Lys Asp Ala Ser
    210                 215                 220 ttt atg cgt tct aat gat cat ggt aac aga gaa gtt ggt aga aat tgg        720
Phe Met Arg Ser Asn Asp His Gly Asn Arg Glu Val Gly Arg Asn Trp
225                 230                 235                 240 gat act agt ggt ctt gaa ggc aca gct ctt aag atg gtt gag ggt gat        768
Asp Thr Ser Gly Leu Glu Gly Thr Ala Leu Lys Met Val Glu Gly Asp
                245                 250                 255 cgc aac tct aag aac tgg tgg aga aag ctt gaa atg gta cgc gag gtt        816
Arg Asn Ser Lys Asn Trp Trp Arg Lys Leu Glu Met Val Arg Glu Val
            260                 265                 270 ata gtt ggg agt gtt gag agg gag gaa cga ttg aag gcg ctc ata tac        864
Ile Val Gly Ser Val Glu Arg Glu Glu Arg Leu Lys Ala Leu Ile Tyr
        275                 280                 285 tct gca att tat ttg aag tgg ata aac aca ggt cag att cct tgt ttt        912
Ser Ala Ile Tyr Leu Lys Trp Ile Asn Thr Gly Gln Ile Pro Cys Phe
    290                 295                 300 gaa gat gga ggg cat cac cgt cca aac agg cat gcc gag att tcc aga        960
Glu Asp Gly Gly His His Arg Pro Asn Arg His Ala Glu Ile Ser Arg
305                 310                 315                 320 ctt ata ttc cgt gag ttg gag cac att tgc agt aag aaa gat gct act       1008
Leu Ile Phe Arg Glu Leu Glu His Ile Cys Ser Lys Lys Asp Ala Thr
                325                 330                 335 cca gag gaa gtg ctt gtt gct cgg aaa atc cat ccg tgt tta cct tct       1056
Pro Glu Glu Val Leu Val Ala Arg Lys Ile His Pro Cys Leu Pro Ser
            340                 345                 350 ttc aaa gca gag ttt act gca gct gtc cct cta act cgg att agg gac       1104
Phe Lys Ala Glu Phe Thr Ala Ala Val Pro Leu Thr Arg Ile Arg Asp
        355                 360                 365 ata gcc cat cgg aat gat att cct cat gat ctc aag caa gaa atc aag       1152
Ile Ala His Arg Asn Asp Ile Pro His Asp Leu Lys Gln Glu Ile Lys
    370                 375                 380 cat acg ata caa aat aag ctt cac cgg aat gct ggt cca gaa gat cta       1200
His Thr Ile Gln Asn Lys Leu His Arg Asn Ala Gly Pro Glu Asp Leu
385                 390                 395                 400 att gca aca gaa gca atg ctt caa cga att acc gag acc cca gga aaa       1248
Ile Ala Thr Glu Ala Met Leu Gln Arg Ile Thr Glu Thr Pro Gly Lys
                405                 410                 415 tat agt gga gac ttt gtg gag cag ttt aaa ata ttc cat aat gag ctt       1296
Tyr Ser Gly Asp Phe Val Glu Gln Phe Lys Ile Phe His Asn Glu Leu
            420                 425                 430 aaa gat ttc ttt aat gct gga agt ctc act gaa cag ctt gat tct atg       1344
```

```
            Lys Asp Phe Phe Asn Ala Gly Ser Leu Thr Glu Gln Leu Asp Ser Met
                    435                 440                 445 aaa att tct atg gat gat aga ggt ctt tct gcg ctc aat ttg ttt ttt        1392
Lys Ile Ser Met Asp Asp Arg Gly Leu Ser Ala Leu Asn Leu Phe Phe
        450                 455                 460 gaa tgt aaa aag cgc ctt gac aca tca gga gaa tca agc aat gtt ttg        1440
Glu Cys Lys Lys Arg Leu Asp Thr Ser Gly Glu Ser Ser Asn Val Leu
465                 470                 475                 480 gag ttg att aaa acc atg cat tct cta gct tct tta aga gaa aca att        1488
Glu Leu Ile Lys Thr Met His Ser Leu Ala Ser Leu Arg Glu Thr Ile
                    485                 490                 495 ata aag gaa ctt aat agc ggc ttg cga aat gat gct cct gat act gcc        1536
Ile Lys Glu Leu Asn Ser Gly Leu Arg Asn Asp Ala Pro Asp Thr Ala
                500                 505                 510 att gca atg cgc cag aag tgg cgc ctt tgt gag atc ggc ctc gag gac        1584
Ile Ala Met Arg Gln Lys Trp Arg Leu Cys Glu Ile Gly Leu Glu Asp
            515                 520                 525 tac ttt ttt gtt cta cta agc aga ttc ctc aat gct ctt gaa act atg        1632
Tyr Phe Phe Val Leu Leu Ser Arg Phe Leu Asn Ala Leu Glu Thr Met
530                 535                 540 gga gga gct gat caa ctg gca aaa gat gtg gga tca aga aac gtt gcc        1680
Gly Gly Ala Asp Gln Leu Ala Lys Asp Val Gly Ser Arg Asn Val Ala
545                 550                 555                 560 tca tgg aat gat cca cta gat gct ttg gtg ttg ggt gtt cac caa gta        1728
Ser Trp Asn Asp Pro Leu Asp Ala Leu Val Leu Gly Val His Gln Val
                565                 570                 575 ggt cta tct ggt tgg aag caa gaa gaa tgt tta gcc att gga aat gaa        1776
Gly Leu Ser Gly Trp Lys Gln Glu Glu Cys Leu Ala Ile Gly Asn Glu
            580                 585                 590 ctc ctt gct tgg cga gaa agg gac cta ctt gaa aaa gaa ggg gaa gag        1824
Leu Leu Ala Trp Arg Glu Arg Asp Leu Leu Glu Lys Glu Gly Glu Glu
        595                 600                 605 gat gga aaa aca att tgg gcc atg agg ctg aaa gca act ctt gat cga        1872
Asp Gly Lys Thr Ile Trp Ala Met Arg Leu Lys Ala Thr Leu Asp Arg
610                 615                 620 gca cgc aga tta aca gca gaa tat tct gat ttg ctt ctt caa ata ttt        1920
Ala Arg Arg Leu Thr Ala Glu Tyr Ser Asp Leu Leu Leu Gln Ile Phe
625                 630                 635                 640 cct cct aat gtg gag att tta gga aaa gct cta gga att cca gag aat        1968
Pro Pro Asn Val Glu Ile Leu Gly Lys Ala Leu Gly Ile Pro Glu Asn
                645                 650                 655 agt gtc aag acc tat aca gaa gca gag att cgt gct gga att att ttc        2016
Ser Val Lys Thr Tyr Thr Glu Ala Glu Ile Arg Ala Gly Ile Ile Phe
            660                 665                 670 cag atc tca aag ctc tgc act gtt ctt cta aaa gct gta aga aat tca        2064
Gln Ile Ser Lys Leu Cys Thr Val Leu Leu Lys Ala Val Arg Asn Ser
        675                 680                 685 ctt ggt tct gag ggc tgg gat gtc gtt gta cct gga tcg acg tct ggg        2112
Leu Gly Ser Glu Gly Trp Asp Val Val Val Pro Gly Ser Thr Ser Gly
690                 695                 700 aca tta gtt cag gtt gag agc att gtt ccg gga tca ttg cca gca act        2160
Thr Leu Val Gln Val Glu Ser Ile Val Pro Gly Ser Leu Pro Ala Thr
705                 710                 715                 720 tct ggt ggt cct att att ctc ttg gtc aat aaa gct gat ggc gat gaa        2208
Ser Gly Gly Pro Ile Ile Leu Leu Val Asn Lys Ala Asp Gly Asp Glu
                725                 730                 735 gag gta agt gct gct aat ggg aac ata gct gga gtc atg ctt ctg cag        2256
Glu Val Ser Ala Ala Asn Gly Asn Ile Ala Gly Val Met Leu Leu Gln
            740                 745                 750 gag ctg cct cac ttg tct cac ctt ggc gtt aga gcg cgg cag gag aaa        2304
```

```
                Glu Leu Pro His Leu Ser His Leu Gly Val Arg Ala Arg Gln Glu Lys
                    755                 760                 765 att gtc ttt gtg aca tgt gat gat gat gac aag gtt gct gat ata cga        2352
Ile Val Phe Val Thr Cys Asp Asp Asp Asp Lys Val Ala Asp Ile Arg
770                 775                 780 cga ctt gtg gga aaa ttt gtg agg ttg gaa gca tct cca agt cat gtg        2400
Arg Leu Val Gly Lys Phe Val Arg Leu Glu Ala Ser Pro Ser His Val
785                 790                 795                 800 aat ctg ata ctt tca act gag ggt agg agt cgc act tcc aaa tcc agt        2448
Asn Leu Ile Leu Ser Thr Glu Gly Arg Ser Arg Thr Ser Lys Ser Ser
                805                 810                 815 gcg acc aaa aaa acg gat aag aac agc tta tct aag aaa aaa aca gat        2496
Ala Thr Lys Lys Thr Asp Lys Asn Ser Leu Ser Lys Lys Lys Thr Asp
            820                 825                 830 aag aag agc tta tct atc gat gat gaa gaa tca aag cct ggt tcc tca        2544
Lys Lys Ser Leu Ser Ile Asp Asp Glu Glu Ser Lys Pro Gly Ser Ser
        835                 840                 845 tct tcc aat agc ctc ctt tac tct tcc aag gat atc cct agt gga gga        2592
Ser Ser Asn Ser Leu Leu Tyr Ser Ser Lys Asp Ile Pro Ser Gly Gly
    850                 855                 860 atc ata gca ctt gct gat gca gat gta cca act tct ggt tca aaa tct        2640
Ile Ile Ala Leu Ala Asp Ala Asp Val Pro Thr Ser Gly Ser Lys Ser
865                 870                 875                 880 gct gca tgt ggt ctt ctt gca tct tta gca gaa gcc tct agt aaa gtg        2688
Ala Ala Cys Gly Leu Leu Ala Ser Leu Ala Glu Ala Ser Ser Lys Val
                885                 890                 895 cac agc gaa cac gga gtt ccg gca tca ttt aag gtt cca act gga gtt        2736
His Ser Glu His Gly Val Pro Ala Ser Phe Lys Val Pro Thr Gly Val
            900                 905                 910 gtc ata cct ttt gga tcg atg gaa tta gct tta aag caa aat aat tcg        2784
Val Ile Pro Phe Gly Ser Met Glu Leu Ala Leu Lys Gln Asn Asn Ser
        915                 920                 925 gaa gaa aag ttt gcg tct ttg cta gaa aaa cta gaa acc gcc aga cct        2832
Glu Glu Lys Phe Ala Ser Leu Leu Glu Lys Leu Glu Thr Ala Arg Pro
    930                 935                 940 gag ggt ggt gag cta gac gac ata tgt gac cag atc cat gaa gtg atg        2880
Glu Gly Gly Glu Leu Asp Asp Ile Cys Asp Gln Ile His Glu Val Met
945                 950                 955                 960 aaa acg ttg caa gtg cct aaa gaa aca atc aac agc ata agc aaa gcg        2928
Lys Thr Leu Gln Val Pro Lys Glu Thr Ile Asn Ser Ile Ser Lys Ala
                965                 970                 975 ttt ctc aaa gat gct cgt ctc att gtt cgt tca agt gct aac gtc gag        2976
Phe Leu Lys Asp Ala Arg Leu Ile Val Arg Ser Ser Ala Asn Val Glu
            980                 985                 990 gac tta gcc gga atg tca gct gca gga ctc tat gaa tca atc cct aac        3024
Asp Leu Ala Gly Met Ser Ala Ala Gly Leu Tyr Glu Ser Ile Pro Asn
        995                 1000                1005 gtg agt ccc tcg gat cct ttg gtg ttt tca gat tcg gtt tgc caa            3069
Val Ser Pro Ser Asp Pro Leu Val Phe Ser Asp Ser Val Cys Gln
    1010                1015                1020 gtt tgg gct tct ctc tac aca aga aga gct gtt cta agc cgt aga            3114
Val Trp Ala Ser Leu Tyr Thr Arg Arg Ala Val Leu Ser Arg Arg
    1025                1030                1035 gct gct ggt gtc tct caa aga gaa gct tca atg gct gtt ctc gtt            3159
Ala Ala Gly Val Ser Gln Arg Glu Ala Ser Met Ala Val Leu Val
    1040                1045                1050 caa gaa atg ctt tcg ccg gac tta tca ttc gtt ctg cac aca gtg            3204
Gln Glu Met Leu Ser Pro Asp Leu Ser Phe Val Leu His Thr Val
    1055                1060                1065 agt cca gct gat ccg gac agt aac ctt gtg gaa gcc gag atc gct            3249
```

```
Ser  Pro  Ala  Asp  Pro  Asp  Ser  Asn  Leu  Val  Glu  Ala  Glu  Ile  Ala
     1070                1075                1080 cct  ggt  tta  ggt  gag  act  tta  gct  tca  gga  aca  aga  gga  aca  cca    3294
Pro  Gly  Leu  Gly  Glu  Thr  Leu  Ala  Ser  Gly  Thr  Arg  Gly  Thr  Pro
1085                1090                1095 tgg  aga  ctc  gct  tcg  ggt  aag  ctc  gac  ggg  att  gta  caa  acc  tta    3339
Trp  Arg  Leu  Ala  Ser  Gly  Lys  Leu  Asp  Gly  Ile  Val  Gln  Thr  Leu
1100                1105                1110 gct  ttc  gca  aac  ttc  agc  gaa  gag  ctt  ctt  gtg  tca  gga  aca  ggt    3384
Ala  Phe  Ala  Asn  Phe  Ser  Glu  Glu  Leu  Leu  Val  Ser  Gly  Thr  Gly
1115                1120                1125 cct  gct  gat  gga  aaa  tac  gtt  cgg  ttg  acc  gtg  gac  tat  agc  aaa    3429
Pro  Ala  Asp  Gly  Lys  Tyr  Val  Arg  Leu  Thr  Val  Asp  Tyr  Ser  Lys
     1130                1135                1140 aaa  cgt  tta  act  gtt  gac  tcg  gtg  ttt  aga  cag  cag  ctc  ggt  cag    3474
Lys  Arg  Leu  Thr  Val  Asp  Ser  Val  Phe  Arg  Gln  Gln  Leu  Gly  Gln
1145                1150                1155 aga  ctc  ggt  tcg  gtt  ggt  ttc  ttc  ttg  gaa  aga  aac  ttt  ggc  tgt    3519
Arg  Leu  Gly  Ser  Val  Gly  Phe  Phe  Leu  Glu  Arg  Asn  Phe  Gly  Cys
1160                1165                1170 gct  caa  gac  gtt  gaa  ggt  tgt  ttg  gtt  ggt  gaa  gat  gtt  tac  att    3564
Ala  Gln  Asp  Val  Glu  Gly  Cys  Leu  Val  Gly  Glu  Asp  Val  Tyr  Ile
1175                1180                1185 gtt  cag  tca  agg  cca  caa  cct  ctg  tag                                  3591
Val  Gln  Ser  Arg  Pro  Gln  Pro  Leu
1190                1195

<210> SEQ ID NO 2
<211> LENGTH: 1196
<212> TYPE: PRT
<213> ORGANISM: Arabidopsis thaliana

<400> SEQUENCE: 2

Met  Glu  Ser  Ile  Gly  Ser  His  Cys  Cys  Ser  Ser  Pro  Phe  Thr  Phe  Ile
1                   5                   10                  15

Thr  Arg  Asn  Ser  Ser  Ser  Ser  Leu  Pro  Arg  Leu  Val  Asn  Ile  Thr  His
              20                  25                  30

Arg  Val  Asn  Leu  Ser  His  Gln  Ser  His  Arg  Leu  Arg  Asn  Ser  Asn  Ser
         35                  40                  45

Arg  Leu  Thr  Cys  Thr  Ala  Thr  Ser  Ser  Ser  Thr  Ile  Glu  Glu  Gln  Arg
50                  55                  60

Lys  Lys  Lys  Asp  Gly  Ser  Gly  Thr  Lys  Val  Arg  Leu  Asn  Val  Arg  Leu
65                  70                  75                  80

Asp  His  Gln  Val  Asn  Phe  Gly  Asp  His  Val  Ala  Met  Phe  Gly  Ser  Ala
              85                  90                  95

Lys  Glu  Ile  Gly  Ser  Trp  Lys  Lys  Ser  Pro  Leu  Asn  Trp  Ser  Glu
         100                 105                 110

Asn  Gly  Trp  Val  Cys  Glu  Leu  Glu  Leu  Asp  Gly  Gly  Gln  Val  Leu  Glu
         115                 120                 125

Tyr  Lys  Phe  Val  Ile  Val  Lys  Asn  Asp  Gly  Ser  Leu  Ser  Trp  Glu  Ser
         130                 135                 140

Gly  Asp  Asn  Arg  Val  Leu  Lys  Val  Pro  Asn  Ser  Gly  Asn  Phe  Ser  Val
145                 150                 155                 160

Val  Cys  His  Trp  Asp  Ala  Thr  Arg  Glu  Thr  Leu  Asp  Leu  Pro  Gln  Glu
                   165                 170                 175

Val  Gly  Asn  Asp  Asp  Val  Gly  Asp  Gly  His  Glu  Arg  Asp  Asn
              180                 185                 190

His  Asp  Val  Gly  Asp  Asp  Arg  Val  Val  Gly  Ser  Glu  Asn  Gly  Ala  Gln
```

```
                195                 200                 205
Leu Gln Lys Ser Thr Leu Gly Gly Gln Trp Gln Gly Lys Asp Ala Ser
    210                 215                 220
Phe Met Arg Ser Asn Asp His Gly Asn Arg Glu Val Gly Arg Asn Trp
225                 230                 235                 240
Asp Thr Ser Gly Leu Glu Gly Thr Ala Leu Lys Met Val Glu Gly Asp
                245                 250                 255
Arg Asn Ser Lys Asn Trp Trp Arg Lys Leu Glu Met Val Arg Glu Val
                260                 265                 270
Ile Val Gly Ser Val Glu Arg Glu Arg Leu Lys Ala Leu Ile Tyr
                275                 280                 285
Ser Ala Ile Tyr Leu Lys Trp Ile Asn Thr Gly Gln Ile Pro Cys Phe
    290                 295                 300
Glu Asp Gly Gly His His Arg Pro Asn Arg His Ala Glu Ile Ser Arg
305                 310                 315                 320
Leu Ile Phe Arg Glu Leu Glu His Ile Cys Ser Lys Lys Asp Ala Thr
                325                 330                 335
Pro Glu Glu Val Leu Val Ala Arg Lys Ile His Pro Cys Leu Pro Ser
                340                 345                 350
Phe Lys Ala Glu Phe Thr Ala Ala Val Pro Leu Thr Arg Ile Arg Asp
    355                 360                 365
Ile Ala His Arg Asn Asp Ile Pro His Asp Leu Lys Gln Glu Ile Lys
370                 375                 380
His Thr Ile Gln Asn Lys Leu His Arg Asn Ala Gly Pro Glu Asp Leu
385                 390                 395                 400
Ile Ala Thr Glu Ala Met Leu Gln Arg Ile Thr Glu Thr Pro Gly Lys
                405                 410                 415
Tyr Ser Gly Asp Phe Val Glu Gln Phe Lys Ile Phe His Asn Glu Leu
                420                 425                 430
Lys Asp Phe Phe Asn Ala Gly Ser Leu Thr Glu Gln Leu Asp Ser Met
    435                 440                 445
Lys Ile Ser Met Asp Asp Arg Gly Leu Ser Ala Leu Asn Leu Phe Phe
450                 455                 460
Glu Cys Lys Lys Arg Leu Asp Thr Ser Gly Glu Ser Ser Asn Val Leu
465                 470                 475                 480
Glu Leu Ile Lys Thr Met His Ser Leu Ala Ser Leu Arg Glu Thr Ile
                485                 490                 495
Ile Lys Glu Leu Asn Ser Gly Leu Arg Asn Asp Ala Pro Asp Thr Ala
                500                 505                 510
Ile Ala Met Arg Gln Lys Trp Arg Leu Cys Glu Ile Gly Leu Glu Asp
                515                 520                 525
Tyr Phe Phe Val Leu Leu Ser Arg Phe Leu Asn Ala Leu Glu Thr Met
    530                 535                 540
Gly Gly Ala Asp Gln Leu Ala Lys Asp Val Gly Ser Arg Asn Val Ala
545                 550                 555                 560
Ser Trp Asn Asp Pro Leu Asp Ala Leu Val Leu Gly Val His Gln Val
                565                 570                 575
Gly Leu Ser Gly Trp Lys Gln Glu Glu Cys Leu Ala Ile Gly Asn Glu
                580                 585                 590
Leu Leu Ala Trp Arg Glu Arg Asp Leu Leu Glu Lys Glu Gly Glu Glu
    595                 600                 605
Asp Gly Lys Thr Ile Trp Ala Met Arg Leu Lys Ala Thr Leu Asp Arg
610                 615                 620
```

-continued

```
Ala Arg Arg Leu Thr Ala Glu Tyr Ser Asp Leu Leu Gln Ile Phe
625                 630                 635                 640

Pro Pro Asn Val Glu Ile Leu Gly Lys Ala Leu Gly Ile Pro Glu Asn
            645                 650                 655

Ser Val Lys Thr Tyr Thr Glu Ala Glu Ile Arg Ala Gly Ile Ile Phe
                660                 665                 670

Gln Ile Ser Lys Leu Cys Thr Val Leu Leu Lys Ala Val Arg Asn Ser
            675                 680                 685

Leu Gly Ser Glu Gly Trp Asp Val Val Pro Gly Ser Thr Ser Gly
    690                 695                 700

Thr Leu Val Gln Val Glu Ser Ile Val Pro Gly Ser Leu Pro Ala Thr
705                 710                 715                 720

Ser Gly Gly Pro Ile Ile Leu Val Asn Lys Ala Asp Gly Asp Glu
                725                 730                 735

Glu Val Ser Ala Ala Asn Gly Asn Ile Ala Gly Val Met Leu Leu Gln
            740                 745                 750

Glu Leu Pro His Leu Ser His Leu Gly Val Arg Ala Arg Gln Glu Lys
            755                 760                 765

Ile Val Phe Val Thr Cys Asp Asp Asp Lys Val Ala Asp Ile Arg
770                 775                 780

Arg Leu Val Gly Lys Phe Val Arg Leu Glu Ala Ser Pro Ser His Val
785                 790                 795                 800

Asn Leu Ile Leu Ser Thr Glu Gly Arg Ser Arg Thr Ser Lys Ser Ser
                805                 810                 815

Ala Thr Lys Lys Thr Asp Lys Asn Ser Leu Ser Lys Lys Thr Asp
            820                 825                 830

Lys Lys Ser Leu Ser Ile Asp Asp Glu Glu Ser Lys Pro Gly Ser Ser
            835                 840                 845

Ser Ser Asn Ser Leu Leu Tyr Ser Ser Lys Ile Pro Ser Gly Gly
            850                 855                 860

Ile Ile Ala Leu Ala Asp Ala Asp Val Pro Thr Ser Gly Ser Lys Ser
865                 870                 875                 880

Ala Ala Cys Gly Leu Leu Ala Ser Leu Ala Glu Ala Ser Ser Lys Val
                885                 890                 895

His Ser Glu His Gly Val Pro Ala Ser Phe Lys Val Pro Thr Gly Val
            900                 905                 910

Val Ile Pro Phe Gly Ser Met Glu Leu Ala Leu Lys Gln Asn Asn Ser
            915                 920                 925

Glu Glu Lys Phe Ala Ser Leu Leu Glu Lys Leu Glu Thr Ala Arg Pro
            930                 935                 940

Glu Gly Gly Glu Leu Asp Asp Ile Cys Asp Gln Ile His Glu Val Met
945                 950                 955                 960

Lys Thr Leu Gln Val Pro Lys Glu Thr Ile Asn Ser Ile Ser Lys Ala
                965                 970                 975

Phe Leu Lys Asp Ala Arg Leu Ile Val Arg Ser Ser Ala Asn Val Glu
            980                 985                 990

Asp Leu Ala Gly Met Ser Ala Ala  Gly Leu Tyr Glu Ser  Ile Pro Asn
            995                 1000                1005

Val Ser  Pro Ser Asp Pro Leu  Val Phe Ser Asp Ser  Val Cys Gln
    1010                1015                1020

Val Trp  Ala Ser Leu Tyr Thr  Arg Arg Ala Val Leu  Ser Arg Arg
    1025                1030                1035

Ala Ala  Gly Val Ser Gln Arg  Glu Ala Ser Met Ala  Val Leu Val
    1040                1045                1050
```

```
Gln Glu Met Leu Ser Pro Asp Leu Ser Phe Val Leu His Thr Val
    1055                1060                1065

Ser Pro Ala Asp Pro Asp Ser Asn Leu Val Glu Ala Glu Ile Ala
    1070                1075                1080

Pro Gly Leu Gly Glu Thr Leu Ala Ser Gly Thr Arg Gly Thr Pro
    1085                1090                1095

Trp Arg Leu Ala Ser Gly Lys Leu Asp Gly Ile Val Gln Thr Leu
    1100                1105                1110

Ala Phe Ala Asn Phe Ser Glu Glu Leu Leu Val Ser Gly Thr Gly
    1115                1120                1125

Pro Ala Asp Gly Lys Tyr Val Arg Leu Thr Val Asp Tyr Ser Lys
    1130                1135                1140

Lys Arg Leu Thr Val Asp Ser Val Phe Arg Gln Gln Leu Gly Gln
    1145                1150                1155

Arg Leu Gly Ser Val Gly Phe Phe Leu Glu Arg Asn Phe Gly Cys
    1160                1165                1170

Ala Gln Asp Val Glu Gly Cys Leu Val Gly Glu Asp Val Tyr Ile
    1175                1180                1185

Val Gln Ser Arg Pro Gln Pro Leu
    1190                1195

<210> SEQ ID NO 3
<211> LENGTH: 3644
<212> TYPE: DNA
<213> ORGANISM: Oryza sativa
<220> FEATURE:
<221> NAME/KEY: CDS
<222> LOCATION: (13)..(3633)
<223> OTHER INFORMATION:

<400> SEQUENCE: 3
cgaggaggat ca atg acg tcg ctg cgg ccc ctc gaa acc tcg ctc tcc ata      51
              Met Thr Ser Leu Arg Pro Leu Glu Thr Ser Leu Ser Ile
                1               5                   10 ggc ggc agg ccg cgc cgt ggt ctc gtc ctc ccg ccg ccc gga gtc ggt        99
Gly Gly Arg Pro Arg Arg Gly Leu Val Leu Pro Pro Pro Gly Val Gly
 15                  20                  25 gcg ggt gtg ctg ctc cgc cgg gga gcg atg gcg ctc cct ggg cgg cgc       147
Ala Gly Val Leu Leu Arg Arg Gly Ala Met Ala Leu Pro Gly Arg Arg
 30                  35                  40                  45 ggc ttc gcg tgc cgc ggg aga tcc gcg gcc tcg gcg gca gag aga aca       195
Gly Phe Ala Cys Arg Gly Arg Ser Ala Ala Ser Ala Ala Glu Arg Thr
                 50                  55                  60 aag gag aaa aag aga aga gat tct tca aag cag cca ttg gtg cat ctc       243
Lys Glu Lys Lys Arg Arg Asp Ser Ser Lys Gln Pro Leu Val His Leu
             65                  70                  75 cag gtt tgt cta gag cac cag gtt aag ttt ggt gag cat gta ggc att       291
Gln Val Cys Leu Glu His Gln Val Lys Phe Gly Glu His Val Gly Ile
         80                  85                  90 atc ggt tcc aca aag gag ctt ggt tca tgg gag gag cag gtt gaa ctg       339
Ile Gly Ser Thr Lys Glu Leu Gly Ser Trp Glu Glu Gln Val Glu Leu
     95                 100                 105 gaa tgg act aca aat ggt tgg gtc tgc cag ctt aag ctc cct gga gaa       387
Glu Trp Thr Thr Asn Gly Trp Val Cys Gln Leu Lys Leu Pro Gly Glu
110                 115                 120                 125 aca ctt gtg gag ttt aaa ttt gtt ata ttt ttg gtg gga gga aaa gat       435
Thr Leu Val Glu Phe Lys Phe Val Ile Phe Leu Val Gly Gly Lys Asp
                130                 135                 140 aaa ata tgg gaa gat ggt aat aac cgt gtt gtt gag ctg ccg aag gat       483
```

```
                Lys Ile Trp Glu Asp Gly Asn Asn Arg Val Val Glu Leu Pro Lys Asp
                                145                 150                 155 ggt aag ttt gat ata gta tgc cac tgg aat aga aca gaa gag cca tta              531
Gly Lys Phe Asp Ile Val Cys His Trp Asn Arg Thr Glu Glu Pro Leu
160                 165                 170 gaa ctt tta gga aca cca aag ttt gag ttg gtc gga gaa gct gaa aag              579
Glu Leu Leu Gly Thr Pro Lys Phe Glu Leu Val Gly Glu Ala Glu Lys
    175                 180                 185 aat act ggc gag gat gct tca gca tct gta act ttt gca cct gaa aaa              627
Asn Thr Gly Glu Asp Ala Ser Ala Ser Val Thr Phe Ala Pro Glu Lys
190                 195                 200                 205 gtt caa gat att tca gtt gtt gag aat ggt gat cca gca cca gag gcc              675
Val Gln Asp Ile Ser Val Val Glu Asn Gly Asp Pro Ala Pro Glu Ala
                210                 215                 220 gag tca agc aaa ttt ggt ggg caa tgg caa gga agt aaa act gtt ttc              723
Glu Ser Ser Lys Phe Gly Gly Gln Trp Gln Gly Ser Lys Thr Val Phe
            225                 230                 235 atg aga tca aat gag cat ctg aat aag gag gct gat agg atg tgg gat              771
Met Arg Ser Asn Glu His Leu Asn Lys Glu Ala Asp Arg Met Trp Asp
        240                 245                 250 aca act ggg ctt gat gga ata gca ctg aaa ctg gtg gag ggc gat aaa              819
Thr Thr Gly Leu Asp Gly Ile Ala Leu Lys Leu Val Glu Gly Asp Lys
    255                 260                 265 gca tcc agg aac tgg tgg cgg aag tta gag gtt gtt cgc ggg ata ttg              867
Ala Ser Arg Asn Trp Trp Arg Lys Leu Glu Val Val Arg Gly Ile Leu
270                 275                 280                 285 tca gaa tct ttt gat gac cag agt cgt ctg ggg gcc ctt gta tac tca              915
Ser Glu Ser Phe Asp Asp Gln Ser Arg Leu Gly Ala Leu Val Tyr Ser
                290                 295                 300 gct att tat ctg aag tgg att tat aca ggt cag ata tcg tgc ttt gaa              963
Ala Ile Tyr Leu Lys Trp Ile Tyr Thr Gly Gln Ile Ser Cys Phe Glu
            305                 310                 315 gat ggt ggc cac cat cgg cct aac aaa cat gct gag ata tcg agg caa             1011
Asp Gly Gly His His Arg Pro Asn Lys His Ala Glu Ile Ser Arg Gln
        320                 325                 330 ata ttc cgt gaa ctt gaa atg atg tat tat ggg aaa acc aca tca gcc             1059
Ile Phe Arg Glu Leu Glu Met Met Tyr Tyr Gly Lys Thr Thr Ser Ala
    335                 340                 345 aag gat gtt ctc gtg att cgc aaa att cat ccc ttt tta cct tca ttt             1107
Lys Asp Val Leu Val Ile Arg Lys Ile His Pro Phe Leu Pro Ser Phe
350                 355                 360                 365 aag tca gag ttt aca gcc tct gtc cct cta aca cga att cgt gat att             1155
Lys Ser Glu Phe Thr Ala Ser Val Pro Leu Thr Arg Ile Arg Asp Ile
                370                 375                 380 gct cac cgg aat gac atc cca cat gat ctc aag caa gaa atc aag cat             1203
Ala His Arg Asn Asp Ile Pro His Asp Leu Lys Gln Glu Ile Lys His
            385                 390                 395 act ata caa aac aaa ctt cat cgt aat gct gga cct gag gat ctt att             1251
Thr Ile Gln Asn Lys Leu His Arg Asn Ala Gly Pro Glu Asp Leu Ile
        400                 405                 410 gct aca gaa gtc atg ctt gct agg att act aag acc cct gga gaa tac             1299
Ala Thr Glu Val Met Leu Ala Arg Ile Thr Lys Thr Pro Gly Glu Tyr
    415                 420                 425 agt gaa aca ttt gtt gaa caa ttc acg ata ttt tat agc gaa cta aaa             1347
Ser Glu Thr Phe Val Glu Gln Phe Thr Ile Phe Tyr Ser Glu Leu Lys
430                 435                 440                 445 gat ttc ttc aat gct ggc agc cta ttt gag caa ctg gag tcc atc aag             1395
Asp Phe Phe Asn Ala Gly Ser Leu Phe Glu Gln Leu Glu Ser Ile Lys
                450                 455                 460 gaa tct ctg aac gag tca ggc tta gaa gtt ctc tca tcc ttt gtg gaa             1443
```

```
                Glu Ser Leu Asn Glu Ser Gly Leu Glu Val Leu Ser Ser Phe Val Glu
                            465                 470                 475 acc aaa agg agt ttg gac caa gtg gat cat gca gaa gat ttg gat aaa                 1491
Thr Lys Arg Ser Leu Asp Gln Val Asp His Ala Glu Asp Leu Asp Lys
            480                 485                 490 aat gat acc att caa att ttg atg act acc ttg caa tca tta tct tct                 1539
Asn Asp Thr Ile Gln Ile Leu Met Thr Thr Leu Gln Ser Leu Ser Ser
495                 500                 505 cta aga tcg gtt cta atg aag ggc ctt gaa agt ggc ctt aga aat gat                 1587
Leu Arg Ser Val Leu Met Lys Gly Leu Glu Ser Gly Leu Arg Asn Asp
510                 515                 520                 525 gcg cct gat aat gct ata gca atg cga caa aag tgg cgc ctt tgt gaa                 1635
Ala Pro Asp Asn Ala Ile Ala Met Arg Gln Lys Trp Arg Leu Cys Glu
            530                 535                 540 att agt ctt gag gat tat tca ttt gtt ctg tta agc aga ttc atc aat                 1683
Ile Ser Leu Glu Asp Tyr Ser Phe Val Leu Leu Ser Arg Phe Ile Asn
            545                 550                 555 act ctt gaa gcc tta ggt gga tca gct tca ctt gca aag gat gta gct                 1731
Thr Leu Glu Ala Leu Gly Gly Ser Ala Ser Leu Ala Lys Asp Val Ala
            560                 565                 570 aga aat act act cta tgg gat act act ctt gat gcc ctt gtc att ggc                 1779
Arg Asn Thr Thr Leu Trp Asp Thr Thr Leu Asp Ala Leu Val Ile Gly
            575                 580                 585 atc aat caa gtt agc ttt tca ggt tgg aaa aca gat gaa tgt att gcc                 1827
Ile Asn Gln Val Ser Phe Ser Gly Trp Lys Thr Asp Glu Cys Ile Ala
590                 595                 600                 605 ata ggg aat gag att ctt tcc tgg aag caa aaa ggt cta tct gaa agt                 1875
Ile Gly Asn Glu Ile Leu Ser Trp Lys Gln Lys Gly Leu Ser Glu Ser
            610                 615                 620 gaa ggt tgt gaa gat ggg aaa tat att tgg tca cta aga ctt aaa gct                 1923
Glu Gly Cys Glu Asp Gly Lys Tyr Ile Trp Ser Leu Arg Leu Lys Ala
            625                 630                 635 aca ctg gac aga gca cgg aga tta acg gaa gag tac tct gaa gca ctt                 1971
Thr Leu Asp Arg Ala Arg Arg Leu Thr Glu Glu Tyr Ser Glu Ala Leu
            640                 645                 650 ctt tct ata ttc cct gaa aaa gta atg gtt att ggg aaa gcc ctt gga                 2019
Leu Ser Ile Phe Pro Glu Lys Val Met Val Ile Gly Lys Ala Leu Gly
            655                 660                 665 ata cca gat aac agt gtg aga act tac aca gag gca gaa att cgt gct                 2067
Ile Pro Asp Asn Ser Val Arg Thr Tyr Thr Glu Ala Glu Ile Arg Ala
670                 675                 680                 685 ggc att gtt ttt cag gta tct aaa cta tgc aca gta ctt cag aaa gca                 2115
Gly Ile Val Phe Gln Val Ser Lys Leu Cys Thr Val Leu Gln Lys Ala
            690                 695                 700 att cga gaa gta ctt gga tca act ggc tgg gat gtt ctt gtt cct gga                 2163
Ile Arg Glu Val Leu Gly Ser Thr Gly Trp Asp Val Leu Val Pro Gly
            705                 710                 715 gtg gcc cat gga act ctg atg cgg gtg gaa aga att ctt cct gga tca                 2211
Val Ala His Gly Thr Leu Met Arg Val Glu Arg Ile Leu Pro Gly Ser
            720                 725                 730 tta cct tca tct gtc aaa gaa cct gtg gtt cta att gta gat aag gct                 2259
Leu Pro Ser Ser Val Lys Glu Pro Val Val Leu Ile Val Asp Lys Ala
            735                 740                 745 gat gga gat gaa gag gtc aaa gct gct ggg gat aat ata gtt ggt gtt                 2307
Asp Gly Asp Glu Glu Val Lys Ala Ala Gly Asp Asn Ile Val Gly Val
750                 755                 760                 765 att ctt ctt cag gaa cta cct cac ctt tca cat ctt ggt gtt aga gct                 2355
Ile Leu Leu Gln Glu Leu Pro His Leu Ser His Leu Gly Val Arg Ala
            770                 775                 780 cgt caa gag aat gtt gta ttt gta act tgt gaa tat gat gac aca gtt                 2403
```

```
                   Arg Gln Glu Asn Val Val Phe Val Thr Cys Glu Tyr Asp Asp Thr Val
                                       785                 790                 795 aca gat gtg tat ttg ctt gag gga aaa tat atc aga tta gaa gca tca              2451
Thr Asp Val Tyr Leu Leu Glu Gly Lys Tyr Ile Arg Leu Glu Ala Ser
            800                 805                 810 tcc atc aat gtc aat ctc tca ata gtt tca gaa aaa aat gac aat gct              2499
Ser Ile Asn Val Asn Leu Ser Ile Val Ser Glu Lys Asn Asp Asn Ala
815                 820                 825 gtc tct aca gaa cca aat agt aca ggg aat cca ttt caa cag aaa ctc              2547
Val Ser Thr Glu Pro Asn Ser Thr Gly Asn Pro Phe Gln Gln Lys Leu
    830                 835                 840                 845 caa aat gaa ttc tct cta cca tcg gat atc gag atg cca ctg caa atg              2595
Gln Asn Glu Phe Ser Leu Pro Ser Asp Ile Glu Met Pro Leu Gln Met
                850                 855                 860 tct aag caa aaa agc aaa tca gga gtg aat ggt agt ttt gct gct ctt              2643
Ser Lys Gln Lys Ser Lys Ser Gly Val Asn Gly Ser Phe Ala Ala Leu
            865                 870                 875 gag ctt tca gaa gct tca gtg gaa tca gct ggt gca aaa gct gct gca              2691
Glu Leu Ser Glu Ala Ser Val Glu Ser Ala Gly Ala Lys Ala Ala Ala
880                 885                 890 tgc aga act ctt tct gtt ctt gct tca ttg tct aat aaa gtc tat agt              2739
Cys Arg Thr Leu Ser Val Leu Ala Ser Leu Ser Asn Lys Val Tyr Ser
    895                 900                 905 gat caa gga gtt cca gca gcc ttt aga gtc cct tct ggt gct gtg ata              2787
Asp Gln Gly Val Pro Ala Ala Phe Arg Val Pro Ser Gly Ala Val Ile
910                 915                 920                 925 cca ttt gga tca atg gag gat gcg ctc aag aaa agt gga tca ctg gaa              2835
Pro Phe Gly Ser Met Glu Asp Ala Leu Lys Lys Ser Gly Ser Leu Glu
                930                 935                 940 tcc ttt aca agc ctt cta gaa aag att gaa aca gcc aaa gtc gaa aat              2883
Ser Phe Thr Ser Leu Leu Glu Lys Ile Glu Thr Ala Lys Val Glu Asn
            945                 950                 955 ggt gaa gtt gat agc ctg gcg ttg gag cta caa gca ata att tca cat              2931
Gly Glu Val Asp Ser Leu Ala Leu Glu Leu Gln Ala Ile Ile Ser His
960                 965                 970 ctt tcc cca ccg gag gag act att ata ttt ctc aaa aga atc ttc cca              2979
Leu Ser Pro Pro Glu Glu Thr Ile Ile Phe Leu Lys Arg Ile Phe Pro
    975                 980                 985 cag gat gtc cgg ttg att gtt aga tct agt gct aat gtg gag gat ttg              3027
Gln Asp Val Arg Leu Ile Val Arg Ser Ser Ala Asn Val Glu Asp Leu
990                 995                 1000                1005 gct ggt atg tca gct gct ggt ctc tat gat tca att ccc aat gtc                  3072
Ala Gly Met Ser Ala Ala Gly Leu Tyr Asp Ser Ile Pro Asn Val
                1010                1015                1020 agt ctc atg gac cca tgt gcc ttt gga gct gcg gtt ggg aag gtt                  3117
Ser Leu Met Asp Pro Cys Ala Phe Gly Ala Ala Val Gly Lys Val
            1025                1030                1035 tgg gct tct tta tac aca agg aga gcc atc cta agc cgt cga gcc                  3162
Trp Ala Ser Leu Tyr Thr Arg Arg Ala Ile Leu Ser Arg Arg Ala
        1040                1045                1050 gct ggt gtt tat cag aga gac gcg aca atg gct gtt ctt gtc caa                  3207
Ala Gly Val Tyr Gln Arg Asp Ala Thr Met Ala Val Leu Val Gln
        1055                1060                1065 gaa ata ctg cag cca gat ctc tcc ttc gtg ctt cat act gtt tgc                  3252
Glu Ile Leu Gln Pro Asp Leu Ser Phe Val Leu His Thr Val Cys
        1070                1075                1080 ccc gct gac cat gac ccc aag gtt gtc cag gct gag gtc gcc cct                  3297
Pro Ala Asp His Asp Pro Lys Val Val Gln Ala Glu Val Ala Pro
        1085                1090                1095 ggg ctg ggt gaa acg ctt gct tca gga acc cgt ggc acc ccg tgg                  3342
```

```
                                              -continued

Gly Leu Gly Glu Thr Leu Ala Ser Gly Thr Arg Gly Thr Pro Trp
            1100                1105                1110 agg ctg tca tgt aac aaa ttc gat gga aaa gtt gcc act ctt gcc    3387
Arg Leu Ser Cys Asn Lys Phe Asp Gly Lys Val Ala Thr Leu Ala
            1115                1120                1125 ttt tca aat ttc agt gag gag atg gtg gtg cac aac tct ggt cct    3432
Phe Ser Asn Phe Ser Glu Glu Met Val Val His Asn Ser Gly Pro
            1130                1135                1140 gcc aat gga gaa gta att cgt ctt act gtt gat tac agc aag aag    3477
Ala Asn Gly Glu Val Ile Arg Leu Thr Val Asp Tyr Ser Lys Lys
            1145                1150                1155 cca ttg tcg gtt gat aca acc ttt agg aag cag ttt ggt cag cga    3522
Pro Leu Ser Val Asp Thr Thr Phe Arg Lys Gln Phe Gly Gln Arg
            1160                1165                1170 ctg gct gcg att ggc cag tat ctg gag cag aag ttc ggg agt gca    3567
Leu Ala Ala Ile Gly Gln Tyr Leu Glu Gln Lys Phe Gly Ser Ala
            1175                1180                1185 cag gat gtg gaa ggt tgc ctg gtt ggg aaa gat att ttt ata gtg    3612
Gln Asp Val Glu Gly Cys Leu Val Gly Lys Asp Ile Phe Ile Val
            1190                1195                1200 caa agc agg cca cag cca tag aagccgaatt c                       3644
Gln Ser Arg Pro Gln Pro
            1205

<210> SEQ ID NO 4
<211> LENGTH: 1206
<212> TYPE: PRT
<213> ORGANISM: Oryza sativa

<400> SEQUENCE: 4

Met Thr Ser Leu Arg Pro Leu Glu Thr Ser Leu Ser Ile Gly Gly Arg
1               5                   10                  15

Pro Arg Arg Gly Leu Val Leu Pro Pro Gly Val Gly Ala Gly Val
            20                  25                  30

Leu Leu Arg Arg Gly Ala Met Ala Leu Pro Gly Arg Arg Gly Phe Ala
        35                  40                  45

Cys Arg Gly Arg Ser Ala Ala Ser Ala Ala Glu Arg Thr Lys Glu Lys
50                  55                  60

Lys Arg Arg Asp Ser Ser Lys Gln Pro Leu Val His Leu Gln Val Cys
65                  70                  75                  80

Leu Glu His Gln Val Lys Phe Gly Glu His Val Gly Ile Ile Gly Ser
                85                  90                  95

Thr Lys Glu Leu Gly Ser Trp Glu Glu Gln Val Glu Leu Glu Trp Thr
            100                 105                 110

Thr Asn Gly Trp Val Cys Gln Leu Lys Leu Pro Gly Glu Thr Leu Val
        115                 120                 125

Glu Phe Lys Phe Val Ile Phe Leu Val Gly Gly Lys Asp Lys Ile Trp
    130                 135                 140

Glu Asp Gly Asn Asn Arg Val Val Glu Leu Pro Lys Asp Gly Lys Phe
145                 150                 155                 160

Asp Ile Val Cys His Trp Asn Arg Thr Glu Pro Leu Glu Leu Leu
                165                 170                 175

Gly Thr Pro Lys Phe Glu Leu Val Gly Glu Ala Glu Lys Asn Thr Gly
            180                 185                 190

Glu Asp Ala Ser Ala Ser Val Thr Phe Ala Pro Glu Lys Val Gln Asp
        195                 200                 205

Ile Ser Val Val Glu Asn Gly Asp Pro Ala Pro Glu Ala Glu Ser Ser
    210                 215                 220
```

```
Lys Phe Gly Gly Gln Trp Gln Gly Ser Lys Thr Val Phe Met Arg Ser
225                 230                 235                 240

Asn Glu His Leu Asn Lys Glu Ala Asp Arg Met Trp Asp Thr Thr Gly
                245                 250                 255

Leu Asp Gly Ile Ala Leu Lys Leu Val Glu Gly Asp Lys Ala Ser Arg
            260                 265                 270

Asn Trp Trp Arg Lys Leu Glu Val Val Arg Gly Ile Leu Ser Glu Ser
        275                 280                 285

Phe Asp Asp Gln Ser Arg Leu Gly Ala Leu Val Tyr Ser Ala Ile Tyr
290                 295                 300

Leu Lys Trp Ile Tyr Thr Gly Gln Ile Ser Cys Phe Glu Asp Gly Gly
305                 310                 315                 320

His His Arg Pro Asn Lys His Ala Glu Ile Ser Arg Gln Ile Phe Arg
                325                 330                 335

Glu Leu Glu Met Met Tyr Tyr Gly Lys Thr Thr Ser Ala Lys Asp Val
            340                 345                 350

Leu Val Ile Arg Lys Ile His Pro Phe Leu Pro Ser Phe Lys Ser Glu
        355                 360                 365

Phe Thr Ala Ser Val Pro Leu Thr Arg Ile Arg Asp Ile Ala His Arg
370                 375                 380

Asn Asp Ile Pro His Asp Leu Lys Gln Glu Ile Lys His Thr Ile Gln
385                 390                 395                 400

Asn Lys Leu His Arg Asn Ala Gly Pro Glu Asp Leu Ile Ala Thr Glu
                405                 410                 415

Val Met Leu Ala Arg Ile Thr Lys Thr Pro Gly Glu Tyr Ser Glu Thr
            420                 425                 430

Phe Val Glu Gln Phe Thr Ile Phe Tyr Ser Leu Lys Asp Phe Phe
        435                 440                 445

Asn Ala Gly Ser Leu Phe Glu Gln Leu Glu Ser Ile Lys Glu Ser Leu
450                 455                 460

Asn Glu Ser Gly Leu Glu Val Leu Ser Ser Phe Val Glu Thr Lys Arg
465                 470                 475                 480

Ser Leu Asp Gln Val Asp His Ala Glu Asp Leu Asp Lys Asn Asp Thr
                485                 490                 495

Ile Gln Ile Leu Met Thr Thr Leu Gln Ser Leu Ser Ser Leu Arg Ser
            500                 505                 510

Val Leu Met Lys Gly Leu Glu Ser Gly Leu Arg Asn Asp Ala Pro Asp
        515                 520                 525

Asn Ala Ile Ala Met Arg Gln Lys Trp Arg Leu Cys Glu Ile Ser Leu
530                 535                 540

Glu Asp Tyr Ser Phe Val Leu Leu Ser Arg Phe Ile Asn Thr Leu Glu
545                 550                 555                 560

Ala Leu Gly Gly Ser Ala Ser Leu Ala Lys Asp Val Ala Arg Asn Thr
                565                 570                 575

Thr Leu Trp Asp Thr Thr Leu Asp Ala Leu Val Ile Gly Ile Asn Gln
            580                 585                 590

Val Ser Phe Ser Gly Trp Lys Thr Asp Glu Cys Ile Ala Ile Gly Asn
        595                 600                 605

Glu Ile Leu Ser Trp Lys Gln Lys Gly Leu Ser Glu Ser Glu Gly Cys
610                 615                 620

Glu Asp Gly Lys Tyr Ile Trp Ser Leu Arg Leu Lys Ala Thr Leu Asp
625                 630                 635                 640

Arg Ala Arg Arg Leu Thr Glu Glu Tyr Ser Glu Ala Leu Leu Ser Ile
```

```
                645                 650                 655
Phe Pro Glu Lys Val Met Val Ile Gly Lys Ala Leu Gly Ile Pro Asp
                660                 665                 670
Asn Ser Val Arg Thr Tyr Thr Glu Ala Glu Ile Arg Ala Gly Ile Val
                675                 680                 685
Phe Gln Val Ser Lys Leu Cys Thr Val Leu Gln Lys Ala Ile Arg Glu
                690                 695                 700
Val Leu Gly Ser Thr Gly Trp Asp Val Leu Pro Gly Val Ala His
705                 710                 715                 720
Gly Thr Leu Met Arg Val Glu Arg Ile Leu Pro Gly Ser Leu Pro Ser
                725                 730                 735
Ser Val Lys Glu Pro Val Val Leu Ile Val Asp Lys Ala Asp Gly Asp
                740                 745                 750
Glu Glu Val Lys Ala Ala Gly Asp Asn Ile Val Gly Val Ile Leu Leu
                755                 760                 765
Gln Glu Leu Pro His Leu Ser His Leu Gly Val Arg Ala Arg Gln Glu
                770                 775                 780
Asn Val Val Phe Val Thr Cys Glu Tyr Asp Asp Thr Val Thr Asp Val
785                 790                 795                 800
Tyr Leu Leu Glu Gly Lys Tyr Ile Arg Leu Glu Ala Ser Ser Ile Asn
                805                 810                 815
Val Asn Leu Ser Ile Val Ser Glu Lys Asn Asp Asn Ala Val Ser Thr
                820                 825                 830
Glu Pro Asn Ser Thr Gly Asn Pro Phe Gln Gln Lys Leu Gln Asn Glu
                835                 840                 845
Phe Ser Leu Pro Ser Asp Ile Glu Met Pro Leu Gln Met Ser Lys Gln
                850                 855                 860
Lys Ser Lys Ser Gly Val Asn Gly Ser Phe Ala Ala Leu Glu Leu Ser
865                 870                 875                 880
Glu Ala Ser Val Glu Ser Ala Gly Ala Lys Ala Ala Cys Arg Thr
                885                 890                 895
Leu Ser Val Leu Ala Ser Leu Ser Asn Lys Val Tyr Ser Asp Gln Gly
                900                 905                 910
Val Pro Ala Ala Phe Arg Val Pro Ser Gly Ala Val Ile Pro Phe Gly
                915                 920                 925
Ser Met Glu Asp Ala Leu Lys Lys Ser Gly Ser Leu Glu Ser Phe Thr
                930                 935                 940
Ser Leu Leu Glu Lys Ile Glu Thr Ala Lys Val Glu Asn Gly Glu Val
945                 950                 955                 960
Asp Ser Leu Ala Leu Glu Leu Gln Ala Ile Ile Ser His Leu Ser Pro
                965                 970                 975
Pro Glu Glu Thr Ile Ile Phe Leu Lys Arg Ile Phe Pro Gln Asp Val
                980                 985                 990
Arg Leu Ile Val Arg Ser Ser Ala Asn Val Glu Asp Leu Ala Gly Met
                995                1000                1005
Ser Ala Ala Gly Leu Tyr Asp Ser Ile Pro Asn Val Ser Leu Met
                1010                1015                1020
Asp Pro Cys Ala Phe Gly Ala Ala Val Gly Lys Val Trp Ala Ser
                1025                1030                1035
Leu Tyr Thr Arg Arg Ala Ile Leu Ser Arg Arg Ala Ala Gly Val
                1040                1045                1050
Tyr Gln Arg Asp Ala Thr Met Ala Val Leu Val Gln Glu Ile Leu
                1055                1060                1065
```

```
Gln Pro Asp Leu Ser Phe Val Leu His Thr Val Cys Pro Ala Asp
    1070                1075                1080

His Asp Pro Lys Val Val Gln Ala Glu Val Ala Pro Gly Leu Gly
    1085                1090                1095

Glu Thr Leu Ala Ser Gly Arg Gly Thr Pro Trp Arg Leu Ser
    1100                1105                1110

Cys Asn Lys Phe Asp Gly Lys Val Ala Thr Leu Ala Phe Ser Asn
    1115                1120                1125

Phe Ser Glu Glu Met Val Val His Asn Ser Gly Pro Ala Asn Gly
    1130                1135                1140

Glu Val Ile Arg Leu Thr Val Asp Tyr Ser Lys Lys Pro Leu Ser
    1145                1150                1155

Val Asp Thr Thr Phe Arg Lys Gln Phe Gly Gln Arg Leu Ala Ala
    1160                1165                1170

Ile Gly Gln Tyr Leu Glu Gln Lys Phe Gly Ser Ala Gln Asp Val
    1175                1180                1185

Glu Gly Cys Leu Val Gly Lys Asp Ile Phe Ile Val Gln Ser Arg
    1190                1195                1200

Pro Gln Pro
    1205

<210> SEQ ID NO 5
<211> LENGTH: 12
<212> TYPE: PRT
<213> ORGANISM: Oryza sativa, Arabidopsis thaliana

<400> SEQUENCE: 5

Leu Pro His Leu Ser His Leu Gly Val Arg Ala Arg
1               5                   10

<210> SEQ ID NO 6
<211> LENGTH: 9
<212> TYPE: PRT
<213> ORGANISM: Solanum tuberosum

<400> SEQUENCE: 6

Pro Glu Glu Cys Lys Ala Val Gly Asn
1               5

<210> SEQ ID NO 7
<211> LENGTH: 7
<212> TYPE: PRT
<213> ORGANISM: Solanum tuberosum

<400> SEQUENCE: 7

Thr Glu Glu Tyr Ser Glu Thr
1               5

<210> SEQ ID NO 8
<211> LENGTH: 7
<212> TYPE: PRT
<213> ORGANISM: Solanum tuberosum

<400> SEQUENCE: 8

Arg Phe Val Asn Ala Val Glu
1               5

<210> SEQ ID NO 9
<211> LENGTH: 7
<212> TYPE: PRT
<213> ORGANISM: Solanum tuberosum
```

<400> SEQUENCE: 9

Glu Gly Ser Glu Asp Gly Lys
1               5

<210> SEQ ID NO 10
<211> LENGTH: 403
<212> TYPE: DNA
<213> ORGANISM: Solanum tuberosum
<220> FEATURE:
<221> NAME/KEY: CDS
<222> LOCATION: (1)..(402)
<223> OTHER INFORMATION:

<400> SEQUENCE: 10

```
gcg gat gct tca ata gct atg cgt cag aag tgg cgt ctc tgc gaa atc    48
Ala Asp Ala Ser Ile Ala Met Arg Gln Lys Trp Arg Leu Cys Glu Ile
1               5                   10                  15 ggg ctt gaa gac tat gca ttt gtt ctt ttg agc agg ttt gtg aat gca    96
Gly Leu Glu Asp Tyr Ala Phe Val Leu Leu Ser Arg Phe Val Asn Ala
            20                  25                  30 gtt gaa gct cta ggc gga gct gat tgg ctt gca gag aat gta aca gtg   144
Val Glu Ala Leu Gly Gly Ala Asp Trp Leu Ala Glu Asn Val Thr Val
        35                  40                  45 aaa aac att agt tct tgg aat gat cca att gga gca ctt aca gtt gga   192
Lys Asn Ile Ser Ser Trp Asn Asp Pro Ile Gly Ala Leu Thr Val Gly
50                  55                  60 atc caa cag cta ggt ata tct ggt tgg aag ccc gag gaa tgc aaa gct   240
Ile Gln Gln Leu Gly Ile Ser Gly Trp Lys Pro Glu Glu Cys Lys Ala
65                  70                  75                  80 gtt gga aat gaa ctt ttg tca tgg aaa gaa agg ggt att tca gaa att   288
Val Gly Asn Glu Leu Leu Ser Trp Lys Glu Arg Gly Ile Ser Glu Ile
                85                  90                  95 gaa ggc agc gaa gat ggt aag act ata tgg gca tta aga cta aaa gcg   336
Glu Gly Ser Glu Asp Gly Lys Thr Ile Trp Ala Leu Arg Leu Lys Ala
            100                 105                 110 act ctt gat aga agt cga agg tta act gag gag tat tcc gag aca ctt   384
Thr Leu Asp Arg Ser Arg Arg Leu Thr Glu Glu Tyr Ser Glu Thr Leu
        115                 120                 125 ctc caa ata ttc cct gaa a                                         403
Leu Gln Ile Phe Pro Glu
    130
```

<210> SEQ ID NO 11
<211> LENGTH: 134
<212> TYPE: PRT
<213> ORGANISM: Solanum tuberosum

<400> SEQUENCE: 11

Ala Asp Ala Ser Ile Ala Met Arg Gln Lys Trp Arg Leu Cys Glu Ile
1               5                   10                  15

Gly Leu Glu Asp Tyr Ala Phe Val Leu Leu Ser Arg Phe Val Asn Ala
            20                  25                  30

Val Glu Ala Leu Gly Gly Ala Asp Trp Leu Ala Glu Asn Val Thr Val
        35                  40                  45

Lys Asn Ile Ser Ser Trp Asn Asp Pro Ile Gly Ala Leu Thr Val Gly
    50                  55                  60

Ile Gln Gln Leu Gly Ile Ser Gly Trp Lys Pro Glu Glu Cys Lys Ala
65                  70                  75                  80

Val Gly Asn Glu Leu Leu Ser Trp Lys Glu Arg Gly Ile Ser Glu Ile
                85                  90                  95

Glu Gly Ser Glu Asp Gly Lys Thr Ile Trp Ala Leu Arg Leu Lys Ala

```
                    100                 105                 110
Thr Leu Asp Arg Ser Arg Arg Leu Thr Glu Glu Tyr Ser Glu Thr Leu
        115                 120                 125

Leu Gln Ile Phe Pro Glu
    130

<210> SEQ ID NO 12
<211> LENGTH: 27
<212> TYPE: DNA
<213> ORGANISM: Synthetic

<400> SEQUENCE: 12
gactcaacca cataacacac aaagatc                                          27

<210> SEQ ID NO 13
<211> LENGTH: 21
<212> TYPE: DNA
<213> ORGANISM: Synthetic

<400> SEQUENCE: 13
tggtaacgag gcaaatgcag a                                                21

<210> SEQ ID NO 14
<211> LENGTH: 25
<212> TYPE: DNA
<213> ORGANISM: Synthetic

<400> SEQUENCE: 14
atctcttatc acaccacctc caatg                                            25

<210> SEQ ID NO 15
<211> LENGTH: 24
<212> TYPE: DNA
<213> ORGANISM: Synthetic

<400> SEQUENCE: 15
ggaaccgata atgcctacat gctc                                             24

<210> SEQ ID NO 16
<211> LENGTH: 39
<212> TYPE: DNA
<213> ORGANISM: Synthetic

<400> SEQUENCE: 16
aaaactcgag gaggatcaat gacgtcgctg cggcccctc                             39

<210> SEQ ID NO 17
<211> LENGTH: 21
<212> TYPE: DNA
<213> ORGANISM: Synthetic

<400> SEQUENCE: 17
ccaggttaag tttggtgagc a                                                21

<210> SEQ ID NO 18
<211> LENGTH: 22
<212> TYPE: DNA
<213> ORGANISM: Synthetic

<400> SEQUENCE: 18
caaagcacga tatctgacct gt                                               22

<210> SEQ ID NO 19
```

```
<211> LENGTH: 22
<212> TYPE: DNA
<213> ORGANISM: Synthetic

<400> SEQUENCE: 19
ttgttcgcgg gatattgtca ga                                              22

<210> SEQ ID NO 20
<211> LENGTH: 24
<212> TYPE: DNA
<213> ORGANISM: Synthetic

<400> SEQUENCE: 20
gacaagggca tcaagagtag tatc                                            24

<210> SEQ ID NO 21
<211> LENGTH: 20
<212> TYPE: DNA
<213> ORGANISM: Synthetic

<400> SEQUENCE: 21
atgatgcgcc tgataatgct                                                 20

<210> SEQ ID NO 22
<211> LENGTH: 21
<212> TYPE: DNA
<213> ORGANISM: Synthetic

<400> SEQUENCE: 22
ggcaaacagt atgaagcacg a                                               21

<210> SEQ ID NO 23
<211> LENGTH: 21
<212> TYPE: DNA
<213> ORGANISM: Synthetic

<400> SEQUENCE: 23
catttggatc aatggaggat g                                               21

<210> SEQ ID NO 24
<211> LENGTH: 23
<212> TYPE: DNA
<213> ORGANISM: Synthetic

<400> SEQUENCE: 24
ctatggctgt ggcctgcttt gca                                             23

<210> SEQ ID NO 25
<211> LENGTH: 33
<212> TYPE: DNA
<213> ORGANISM: Synthetic

<400> SEQUENCE: 25
aaaactcgag ctatggctgt ggcctgcttt gca                                  33

<210> SEQ ID NO 26
<211> LENGTH: 28
<212> TYPE: DNA
<213> ORGANISM: Synthetic

<400> SEQUENCE: 26
aaaacaattg gcgcctggag ggaggaga                                        28

<210> SEQ ID NO 27
```

```
<211> LENGTH: 35
<212> TYPE: DNA
<213> ORGANISM: Synthetic

<400> SEQUENCE: 27
aaaacaattg atgatcaatc agacaatcac tagaa                          35

<210> SEQ ID NO 28
<211> LENGTH: 28
<212> TYPE: DNA
<213> ORGANISM: Synthetic

<400> SEQUENCE: 28
ttttctcgag gtccgccttg tttctcct                                  28

<210> SEQ ID NO 29
<211> LENGTH: 26
<212> TYPE: DNA
<213> ORGANISM: Synthetic

<400> SEQUENCE: 29
ttttctcgag ctgcacgggt ccagga                                    26

<210> SEQ ID NO 30
<211> LENGTH: 63
<212> TYPE: DNA
<213> ORGANISM: Synthetic

<400> SEQUENCE: 30
tgcaggctgc agagctccta ggctcgagtt aacactagta agcttaatta agatatcatt    60
tac                                                             63

<210> SEQ ID NO 31
<211> LENGTH: 67
<212> TYPE: DNA
<213> ORGANISM: Synthetic

<400> SEQUENCE: 31
aattgtaaat gatatcttaa ttaagcttac tagtgttaac tcgagcctag gagctctgca    60
gcctgca                                                         67
```

PLANTS WITH REDUCED ACTIVITY OF A STARCH PHOSPHORYLATING ENZYME

CROSS-REFERENCE TO RELATED APPLICATIONS

This application is a divisional application of U.S. application Ser. No. 10/591,540, filed Sep. 1, 2006, which is the U.S. national stage application of International Application No. PCT/EP2005/002450, filed Mar. 4, 2005, which claims the benefit of European Application No. EP04090088.8, filed Mar. 5, 2004, U.S. Provisional Application No. 60/550,022, filed Mar. 5, 2004, European Application No. EP04090121.7, filed Mar. 29, 2004, European Application No. EP04090203.3, filed May 21, 2004, and European Application No. EP04090484.9, filed Dec. 9, 2004, the disclosures of each of which are herein incorporated by reference in their entireties.

The present invention relates to plant cells and plants, which are genetically modified, wherein the genetic modification leads to the reduction of the activity of a starch phosphorylating OK1 protein in comparison with corresponding wild type plant cells or wild type plants that have not been genetically modified. Furthermore, the present invention relates to means and methods for the manufacture of such plant cells and plants. Plant cells and plants of this type synthesise a modified starch. The present invention therefore also relates to the starch synthesised by the plant cells and plants according to the invention, methods for the manufacture of this starch, and the manufacture of starch derivatives of this modified starch, as well as flours containing starches according to the invention.

Furthermore, the present invention relates to nucleic acid molecules, which are suitable for manufacturing plants according to the invention.

With regard to the increasing importance currently attributed to plant constituents as renewable raw material sources, one of the tasks of biotechnological research is to endeavour to adapt these plant raw materials to suit the requirements of the processing industry. Furthermore, in order to enable regenerating raw materials to be used in as many areas of application as possible, it is necessary to achieve a large variety of materials.

Polysaccharide starch is made up of chemically uniform base components, the glucose molecules, but constitutes a complex mixture of different molecule forms, which exhibit differences with regard to the degree of polymerisation and branching, and therefore differ strongly from one another in their physical-chemical characteristics. Discrimination is made between amylose starch, an essentially unbranched polymer made from alpha-1,4-glycosidically linked glucose units, and the amylopectin starch, a branched polymer, in which the branches come about by the occurrence of additional alpha-1,6-glycosidic links. A further essential difference between amylose and amylopectin lies in the molecular weight. While amylose, depending on the origin of the starch, has a molecular weight of $5 \times 10^5$-$10^6$ Da, that of the amylopectin lies between $10^7$ and $10^8$ Da. The two macromolecules can be differentiated by their molecular weight and their different physical-chemical characteristics, which can most easily be made visible by their different iodine bonding characteristics.

Amylose has long been looked upon as a linear polymer, consisting of alpha-1,4-glycosidically linked alpha-D-glucose monomers. In more recent studies, however, the presence of alpha-1,6-glycosidic branching points (ca. 0.1%) has been shown (Hizukuri and Takagi, Carbohydr. Res. 134, (1984), 1-10; Takeda et al., Carbohydr. Res. 132, (1984), 83-92).

The functional characteristics of starches, such as for example the solubility, the retrogradation behaviour, the water binding capacity, the film-forming characteristics, the viscosity, the gelatinisation characteristics, the freezing-thawing stability, the acid stability, the gel strength and the size of the starch granule, are affected amongst other things by the amylose/amylopectin ratio, the molecular weight, the pattern of the side chain distribution, the ion concentration, the lipid and protein content, the average granule size of the starch, the granule morphology of the starch etc. The functional characteristics of starch are also affected by the phosphate content, a non-carbon component of starch. Here, differentiation is made between phosphate, which is bonded covalently in the form of monoesters to the glucose molecules of the starch (described in the following as starch phosphate), and phosphate in the form of phospholipids associated with the starch.

The starch phosphate content varies depending on the type of plant. Therefore, certain maize mutants, for example, synthesise a starch with increased starch phosphate content (waxy maize 0.002% and high-amylose maize 0.013%), while conventional types of maize only have traces of starch phosphate. Similarly small amounts of starch phosphate are found in wheat (0.001%), while no evidence of starch phosphate has been found in oats and sorghum. Likewise, less starch phosphate has been found in rice mutants (waxy rice 0.003%) than in conventional types of rice (0.013%). Significant amounts of starch phosphate have been shown in plants, which synthesise tubers or root storage starch, such as tapioca (0.008%), sweet potato (0.011%), arrowroot (0.021%) or potato (0.089%) for example. The percentage values for the starch phosphate content quoted above refer to the dry weight of starch in each case, and have been determined by Jane et al. (1996, Cereal Foods World 41 (11), 827-832).

Starch phosphate can be present in the form of monoesters at the C-2, C-3 or C-6 position of polymerised glucose monomers (Takeda and Hizukuri, 1971, Starch/Stärke 23, 267-272). The phosphate distribution of the phosphate in starch synthesised by plants is generally distinguished by the fact that about 30% to 40% of the phosphate residues are bonded covalently in the C-3 position and about 60% to 70% of the phosphate residues are bonded covalently in the C-6 position of the glucose molecules (Blennow et al., 2000, Int. J. of Biological Macromolecules 27, 211-218). Blennow et al. (2000, Carbohydrate Polymers 41, 163-174) have determined a starch phosphate content, which is bonded in the C-6 position of the glucose molecules, for different starches such as, for example, potato starch (between 7.8 and 33.5 nMol per mg of starch, depending on the type), starch from different *Curcuma* species (between 1.8 and 63 nMol per mg), tapioca starch (2.5 nMol per mg of starch), rice starch (1.0 nMol per mg of starch), mung bean starch (3.5 nMol per mg of starch) and sorghum starch (0.9 nMol per mg of starch). These authors have been unable to show any starch phosphate bonded at the C-6 position in barley starch and starches from different waxy mutants of maize. Up to now, it has not been possible to establish a connection between the genotype of a plant and the starch phosphate content (Jane et al., 1996, Cereal Foods World 41 (11), 827-832). It is therefore currently only possible to affect the starch phosphate content in plants by means of breeding measures.

Previously, only one protein has been described, which facilitates the introduction of covalent bonds of phosphate residues to the glucose molecules of starch. This protein has the enzymatic activity of an alpha-glucan-water dikinase (GWD, E.C.: 2.7.9.4) (Ritte et al., 2002, PNAS 99, 7166-7171), is frequently described in the literature as R1, and is bonded to the starch granules of the storage starch in potato tubers (Lorberth et al., 1998, Nature Biotechnology 16, 473-477). In the reaction catalysed by R1, the educts alpha-1,4-glucan (starch), adenosintriphosphate (ATP) and water are converted to the products glucan-phosphate (starch phosphate), monophosphate and adenosine monophosphate. In doing so, the residual gamma phosphate of the ATP is transferred to water, and the residual beta phosphate of the ATP is transferred to the glucan (starch). R1 transfers the residual beta phosphate of ATP to the C-6 and the C-3 position of the glucose molecules of alpha-1,4-glucans in vitro. The ratio of C-6 phosphate to C-3 phosphate, which is obtained in the in vitro reaction, is the same as the ratio, which is present in starch isolated from plants (Ritte et al., 2002, PNAS 99, 7166-7171). As about 70% of the starch phosphate present in potato starch is bonded to the glucose monomers of the starch in the C-6 position and about 30% in the C-3 position, this means that R1 preferably phosphorylates the C-6 position of the glucose molecules. Furthermore, it has been shown that by the use of amylopectin from maize, amongst other things, R1 can phosphorylate alpha-1,4-glucans, which do not yet contain covalently bonded phosphate (Ritte et al., 2002, PNAS 99, 7166-7171), i.e. R1 is able to introduce phosphate de novo into alpha-1,4-glucans.

Nucleic acid sequences, and the amino acid sequences corresponding to them, coding an R1 protein, are described from different species, such as, for example, potato (WO 97 11188, GenBank Acc.: AY027522, Y09533), wheat (WO 00 77229, U.S. Pat. No. 6,462,256, GenBank Acc.: AAN93923, GenBank Acc.: AR236165), rice (GenBank Acc.: AAR61445, GenBank Acc.: AR400814), maize (GenBank Acc.: AAR61444, GenBank Acc.: AR400813), soya bean (GenBank Acc.: AAR61446, GenBank Acc.: AR400815), citrus (GenBank Acc.: AY094062) and *Arabidopsis* (GenBank Acc.: AF312027).

Plants, which exhibit a reduced activity of an R1 protein, are described, for example, by Lorberth et al. (1998, Nature Biotechnology 16, 473-477) and in WO 97 11188. Starches, which have been isolated from these plants, which exhibit a reduced activity of an R1 protein, have significantly reduced amounts of starch phosphate.

Further proteins, which catalyse a reaction, which introduce covalently bonded phosphate groups into the starch, have not previously been described. Enzymes, which preferably introduce phosphate groups in the C-3 position and/or the C-2 position of the glucose molecules of starch, are also unknown. Apart from the reduction of the starch phosphate content in plants, there are therefore also no available ways of specifically influencing the phosphorylation of starch in plants, of modifying the phosphate distribution within the starch synthesised by plants and/or of further reducing the starch phosphate content.

The object of the present invention is therefore based on providing modified starches with reduced phosphate content and/or modified phosphate distribution, as well as plant cells and/or plants, which synthesise such a modified starch, as well as means and methods for producing said plants and/or plant cells.

The present invention therefore relates to genetically modified plant cells and genetically modified plants, characterised in that they have a reduced activity of at least one OK1 protein in comparison with corresponding wild type plant cells or wild type plants that have not been genetically modified.

At the same time, the genetic modification can be any genetic modification, which leads to a reduction of the activity of at least one OK1 protein in comparison with corresponding wild type plant cells or wild type plants that have not been genetically modified.

Plants, which have a reduced activity of an OK1 protein, have a high starch (starch excess) phenotype. Furthermore, plants, which have a reduced activity of an OK1 protein, exhibit normal growth in comparison with wild type plants, i.e. the plants are not restricted in their growth by the reduced activity of an OK1 protein. Plants, which have a reduced activity of an OK1 protein, are therefore suitable for cultivation in agriculture, as they contain more starch and therefore more carbohydrate and, at the same time, do not exhibit a restricted growth rate.

The present invention therefore also relates to plant cells and plants according to the invention, which have a high starch phenotype. At the end of the dark phase, plant cells according to the invention and plants according to the invention have at least two times, preferably at least four times, particularly preferably at least six times and especially preferably at least eight times more starch in their leaves than corresponding wild type plant cells or wild type plants respectively.

At the end of the light phase, plant cells according to the invention and plants according to the invention have at least 1.2 times, preferably at least 1.5 times, particularly preferably at least 1.8 times and especially preferably at least two times more starch in their leaves than corresponding wild type plant cells or wild type plants respectively.

Furthermore, plants, which have a reduced activity of an OK1 protein, have a modified ratio of C-6 phosphate to C-3 phosphate, which is bonded to the starch. Surprisingly, it has been found that plants, which have a reduced activity of an OK1 protein, have approximately just as much C-3 phosphate in their leaf starch bonded to the starch as corresponding wild type plants that have not been genetically modified. However, starch isolated from plants, which have a reduced activity of an OK1 protein, in absolute terms contains more phosphate bonded in the C-6 position of the starch than starch isolated from wild type plants that have not been genetically modified.

A further subject of the present invention therefore relates to plant cells according to the invention and plants according to the invention, which have a modified ratio of C-6 phosphate to C-3 phosphate bonded to the starch in comparison with starch isolated from wild type plant cells or wild type plants respectively that have not been genetically modified. Preferably, the ratio of C-6 phosphate to C-3 phosphate bonded to the starch is increased. The increase of the ratio of C-6 phosphate to C-3 phosphate bonded to starch is preferably at least 5%, more preferably at least 10%, particularly preferably at least 20% and especially preferably at least 30%.

In conjunction with the present invention, the term "wild type plant cell" means that the plant cells concerned were used as starting material for the manufacture of the plant cells according to the invention, i.e. their genetic information, apart from the introduced genetic modification, corresponds to that of a plant cell according to the invention.

In conjunction with the present invention, the term "wild type plant" means that the plants concerned were used as starting material for the manufacture of the plants according to the invention, i.e. their genetic information, apart from the introduced genetic modification, corresponds to that of a plant according to the invention.

In conjunction with the present invention, the term "corresponding" means that, in the comparison of several objects, the objects concerned that are compared with one another have been kept under the same conditions. In conjunction with the present invention, the term "corresponding" in conjunction with wild type plant cell or wild type plant means that the plant cells or plants, which are compared with one another, have been raised under the same cultivation conditions and that they have the same (cultivation) age.

In an embodiment of the present invention, the genetic modification of the plant cells according to the invention or the plants according to the invention is brought about by mutagenesis of one or more genes. The type of mutation is not important, as long as it leads to a reduction in the activity of an OK1 protein.

In conjunction with the present invention, the term "mutagenesis" is to be understood to mean any type of introduced mutation, such as deletions, point mutations (nucleotide exchanges), insertions, inversions, gene conversions or chromosome translocations, for example.

Here, the mutation, which leads to the reduction of the activity of at least one endogenous OK1 protein, can be produced by the use of chemical substances or energy-rich radiation (e.g. x-rays, neutron radiation, gamma radiation or UV radiation).

Chemical substances, which can be used to produce chemically induced mutations, and the mutations resulting from the effect of the corresponding mutagens are, for example described in Ehrenberg and Husain, 1981, (Mutation Research 86, 1-113), Müller, 1972 (Biologisches Zentralblatt 91 (1), 31-48). The production of rice mutants using gamma radiation, ethyl methane sulphonate (EMS), N-methyl-N-nitrosurea or sodium azide ($NaN_3$) is described, for example, in Jauhar and Siddiq (1999, Indian Journal of Genetics, 59 (1), 23-28), in Rao (1977, Cytologica 42, 443-450), Gupta and Sharma (1990, *Oryza* 27, 217-219) and Satoh and Omura (1981, Japanese Journal of Breeding 31 (3), 316-326). The production of wheat mutants using $NaN_3$ or maleic hydrazide is described in Arora et al. (1992, Annals of Biology 8 (1), 65-69). An overview of the production of wheat mutants using different types of energy-rich radiation and chemical substances is presented in Scarascia-Mugnozza et al. (1993, Mutation Breeding Review 10, 1-28). Svec et al. (1998, Cereal Research Communications 26 (4), 391-396) describes the use of N-ethyl-N-nitrosurea for producing mutations in triticals. The use of MMS (methyl methane sulphonic acid) and gamma radiation for the production of millet mutants is described in Shashidhara et al. (1990, Journal of Maharashtra Agricultural Universities 15 (1), 20-23).

The manufacture of mutants in plant species, which mainly propagate vegetatively, has been described, for example, for potatoes, which produce a modified starch (Hovenkamp-Hermelink et al. (1987, Theoretical and Applied Genetics 75, 217-221) and for mint with increased oil yield or modified oil quality (Dwivedi et al., 2000, Journal of Medicinal and Aromatic Plant Sciences 22, 460-463).

All these methods are basically suitable for manufacturing the plant cells according to the invention and the plants according to the invention.

Mutations in the appropriate genes, in particular in genes coding an OK1 protein, can be found with the help of methods known to the person skilled in the art. In particular, analyses based on hybridisations with probes (Southern Blot), amplification by means of polymerase chain reaction (PCR), sequencing of related genomic sequences and the search for individual nucleotide exchanges can be used for this purpose. A method of identifying mutations based on hybridisation patterns is, for example, the search for restriction fragment length differences (Restriction Fragment Length Polymorphism, RFLP) (Nam et al., 1989, The Plant Cell 1, 699-705; Leister and Dean, 1993, The Plant Journal 4 (4), 745-750). A method based on PCR is, for example, the analysis of amplified fragment length differences (Amplified Fragment Length Polymorphism, AFLP) (Castiglioni et al., 1998, Genetics 149, 2039-2056; Meksem et al., 2001, Molecular Genetics and Genomics 265, 207-214; Meyer et al., 1998, Molecular and General Genetics 259, 150-160). The use of amplified fragments excised with restriction endonucleases (Cleaved Amplified Polymorphic Sequences, CAPS) can also be used upon for the identification of mutations (Konieczny and Ausubel, 1993, The Plant Journal 4, 403-410; Jarvis et al., 1994, Plant Molecular Biology 24, 685-687; Bachem et al., 1996, The Plant Journal 9 (5), 745-753). Methods for the determination of SNPs have been described by Qi et al. (2001, Nucleic Acids Research 29 (22), e116) Drenkard et al. (2000, Plant Physiology 124, 1483-1492) and Cho et al. (1999, Nature Genetics 23, 203-207) amongst others. Methods, which allow several plants to be investigated for mutations in certain genes in a short time, are particularly suitable. Such a method, so-called TILLING (Targetting Induced Local Lesions IN Genomes), has been described by McCallum et al. (2000, Plant Physiology 123, 439-442).

These methods are basically suitable for identifying plant cells according to the invention and plants according to the invention.

Hoogkamp et al. (2000, Potato Research 43, 179-189) have manufactured stable monoploid mutants starting from a potato mutant (amf), which was manufactured by means of chemical mutagens. These plants do not synthesise any more active enzyme for a starch synthesis connected to the starch granule (GBSS I) and therefore produce an amylose-free starch. The monoploid potato plants obtained can be used as starting material for further mutageneses in order to identify plants, which synthesise a starch with modified characteristics. The plant cells according to the invention and plants according to the invention, which produce a starch according to the invention, can be identified and isolated by appropriate methods.

The plant cells according to the invention and the plants according to the invention have a reduction of the activity of at least one OK1 protein in comparison with corresponding wild type plant cells and wild type plants respectively that have not been genetically modified.

Here, within the framework of the present invention, the term "reduction of activity" means a reduction in the expression of endogenous genes, which code OK1 proteins, and/or a reduction in the quantity of OK1 protein in the plant cells and/or a reduction in the enzymatic activity of OK1 protein in the plant cells.

The reduction in the expression can, for example, be determined by measuring the quantity of transcripts coding OK1 protein, e.g. using Northern blot analysis or RT-PCR. Here, a reduction preferably means a reduction in the amount of transcripts in comparison with corresponding plant cells that have not been genetically modified by at least 50%, in particular by at least 70%, preferably by at least 85% and particularly preferably by at least 95%.

The reduction in the amount of OK1 protein, which results in a reduced activity of this protein in the plant cells concerned, can, for example, be determined by immunological methods such as Western blot analysis, ELISA (Enzyme Linked Immuno Sorbent Assay) or RIA (Radio Immune Assay). Here, a reduction preferably means a reduction in the amount of OK1 protein in comparison with corresponding plant cells that have not been genetically modified by at least 50%, in particular by at least 70%, preferably by at least 85% and particularly preferably by at least 95%.

Methods for manufacturing antibodies, which react specifically with a certain protein, i.e., which bond specifically to said protein, are known to the person skilled in the art (see, for example, Lottspeich and Zorbas (Eds.), 1998, Bioanalytik, Spektrum akad, Verlag, Heidelberg, Berlin, ISBN 3-8274-0041-4). The manufacture of such antibodies is offered by some companies (e.g. Eurogentec, Belgium) as a contract service. A possible way of manufacturing antibodies, which specifically react with an OK1 protein, is described below (see Example 10).

Within the framework of the present invention, the term "OK1 protein" is to be understood to mean a protein, which transfers a phosphate residue of ATP onto already phosphorylated starch (P-starch). Starches isolated from leaves of an *Arabisopsis thaliana* sex1-3 mutant have no detectable amounts of covalently bonded phosphate residues and are not phosphorylated by an OK1 protein, i.e. an OK1 protein according to the invention requires already phosphorylated starch as a substrate for transferring further phosphate residues.

Preferably, the residual beta phosphate of the ATP is transferred from an OK1 protein to the starch, and the residual gamma phosphate of the ATP is transferred to water. A further reaction product produced by a phosphorylating reaction of P-starch carried out using an OK1 protein is AMP (adenosine monophosphate). An OK1 protein is therefore described as [phosphorylated-alpha-1,4-glucan]-water-dikinase ([P-alpha-1,4-glucan]-water-dikinase) or as [phosphorylated-starch]-water-dikinase.

Preferably, an additional phosphate monoester bond is produced in the C-6 position and/or in the C-3 position of a glucose molecule of the P-starch, which is phosphorylated by an OK1 protein. In the phosphorylation of P-starch catalysed by an OK1 protein, it is particularly preferred if more additional phosphate monoester bonds are produced in the C-3 position in comparison with phosphate monoester bonds in the C-6 position of the glucose molecules of the P-starch concerned.

Amino acid sequences, which code OK1 proteins, contain a phosphohistidine domain. Phosphohistidine domains are described, for example, by Tien-Shin Yu et al. (2001, Plant Cell 13, 1907-1918). Preferably, phosphohistidine domains of amino acids coding OK1 proteins contain two histidines.

In the catalysis of a phosphorylating reaction of a P-starch by means of an OK1 protein, a phosphorylated OK1 protein is produced as an intermediate product, in which a phosphate residue of ATP is covalently bonded to an amino acid of the OK1 protein. The intermediate product is produced by autophosphorylation of the OK1 protein, i.e. the OK1 protein itself catalyses the reaction, which leads to the intermediate product. Preferably, a histidine residue of the amino acid sequence coding an OK1 protein is phosphorylated as a result of the autophosphorylation process, particularly preferably a histidine residue, which is part of a phosphohistidine domain.

Furthermore, OK1 proteins according to the invention have an increased bonding activity to P-starch in comparison with non-phosphorylated starches.

As no enzymes have previously been described, which require P-starch as a substrate in order to phosphorylate them further, and which preferably phosphorylate the C-3 position of the glucose molecules of starch, it has also previously not been possible to influence the distribution of starch phosphate in starch. The clarification of the function of an OK1 protein, and thus the provision of an OK1 protein, leads to the fact that plants can now be genetically modified in such a way that they synthesise a starch with modified characteristics. The modification of the phosphate distribution in starch synthesised by plants was previously not possible due to the lack of available means. Due to the provision by the present invention of proteins and nucleic acids according to the invention, it is now also possible to modify the phosphate ratio in native starch.

In conjunction with the present invention, the term "increased bonding activity" is to be understood to mean an increased affinity of a protein to a first substrate in comparison with a second substrate. That is to say, the amount of protein, which, under the same incubation conditions, bonds to a first substrate to a greater extent in comparison with a second substrate, exhibits increased bonding activity to the first substrate.

In conjunction with the present invention, the term "starch phosphate" is to be understood to mean phosphate groups covalently bonded to the glucose molecules of starch.

In conjunction with the present invention, the term "non-phosphorylated starch" is to be understood to mean a starch, which does not contain any detectable amounts of starch phosphate. Different methods of determining the amount of starch phosphate are described. Preferably, the method of determining the amount of starch phosphate described by Ritte et al. (2000, Starch/Stärke 52, 179-185) can be used. Particularly preferably, the determination of the amount of starch phosphate by means of $^{31}$P-NMR is carried out according to the method described by Kasemusuwan and Jane (1996, Cereal Chemistry 73, 702-707).

In conjunction with the present invention, the term "phosphorylated starch" or "P-starch" is to be understood to mean a starch, which contains starch phosphate.

The activity of an OK1 protein can be demonstrated, for example, by in vitro incubation of an OK1 protein using ATP, which contains a labelled phosphate residue in the beta position (labeled ATP). ATP is to be preferred, in which the phosphate residue is specifically labeled in the beta position, i.e. in which only the phosphate residue in the beta position carries a label. Preferably radioactively labeled ATP, particularly preferably ATP, in which the phosphate residue is specifically radioactively labeled in the beta position, and especially preferably ATP, in which the phosphate residue is specifically labeled with $^{33}$P in the beta position, is used. If an OK1 protein is incubated with labeled ATP and starches, which are not phosphorylated, no phosphate is transferred to the starch due to OK1. Preferably, leaf starch of *Arabidopsis thaliana* mutant sex1-3 (Tien-Shin Yu et al., 2001, Plant Cell 13, 1907-1918) is used.

If, on the other hand, an OK1 protein with P-starch is incubated in the presence of labeled ATP, then labeled phosphate covalently bonded to the P-starch can subsequently be shown. Preferably, starch from leaves of *Arabidopsis thaliana*, particularly preferably starch from *Arabidopsis thaliana* sex1-3 mutants enzymatically phosphorylated by means of an R1 protein (Ritte et al., 2002, PNAS 99, 7166-7171) is used.

Labeled phosphate residues, which have been incorporated in P-starch due to an OK1 protein, e.g. by separating the labeled P-starch (e.g. by precipitation with ethanol, filtration, chromatographic methods etc.) from the rest of the reaction mixture and subsequently detecting the labeled phosphate residue in the P-starch fraction, can be shown. At the same time, the labeled phosphate residues bonded in the P-starch fraction can be demonstrated, for example, by determining the amount of radioactivity present in the P-starch fraction (e.g. by means of scintillation counters). Possible methods for demonstrating a protein, which requires P-starch as a substrate for a phosphorylating reaction, are described below under General Methods, Item 11 and in Example 6.

Which positions of the carbon atoms (C-2, C-3 or C-6) of the glucose monomers in P-starch are preferably phosphorylated by an OK1 protein can be determined, for example, by analysing the P-starches phosphorylated by a protein, as described by Ritte et al. (2002, PNAS 99, 7166-7171). For this purpose, a P-starch phosphorylated by a protein is hydrolysed using an acid, and subsequently analysed by means of anion exchange chromatography.

Preferably, the P-starch phosphorylated by an OK1 protein is analysed by means of NMR in order to establish which positions of the carbon atoms (C-2, C-3 or C-6) of the glucose monomers in the P-starch are phosphorylated. A particularly preferred method for identifying the C-atom positions of a glucose molecule of a starch, which are phosphorylated by a reaction catalysed by an OK1 protein, is described below under General Methods, Item 13.

A phosphorylated protein, which is produced as an intermediate product in the phosphorylation of P-starch facilitated by an OK1 protein, can be demonstrated as described, for example, by Ritte et al. (2002, PNAS 99, 7166-7171) for an R1 protein.

To demonstrate the presence of an autophosphorylated intermediate product, an OK1 protein is first incubated in the absence of starch with labeled ATP, preferably with ATP specifically labeled in the beta phosphate position, particularly preferably with ATP specifically labeled with $^{33}$P in the beta phosphate position. In parallel with this, a reaction preparation 2, which instead of labeled ATP contains corresponding amounts of non-labeled ATP however, is incubated under otherwise identical conditions. Subsequently, non-labeled ATP is added to the reaction mixture 1 in the supernatant, and a mixture of non-labeled ATP and labeled ATP (the same amount of labeled ATP as used previously in reaction mixture 1 and the same amount of non-labeled ATP as added to reaction mixture 1 in the supernatant) is added to reaction mixture 2 and further incubated before P-starch is added to a Part A of reaction mixture 1 (Part 1A) or to a part A of reaction mixture 2 (Part 2A) respectively. The reaction in the remaining Part 1B and Part 2B of the reaction mixture is stopped by denaturing the protein. Part B of the reaction mixture can be stopped by the methods known to the person skilled in the art, which lead to the denaturing of proteins, preferably by adding sodium lauryl sulphate (SDS). Part 1A & Part 2A of the reaction mixture are incubated for at least a further 10 minutes before these reactions are also stopped. The starch present in Part A and Part B of the respective reaction mixture is separated from the remainder of the reaction mixture. If the respective starch is separated by centrifugation, for example, then, on completion of centrifugation, the starch of the respective Part A or Part B of the reaction mixture is to be found in the sedimented pellet, and the proteins in the respective reaction mixture are to be found in the supernatant of the respective centrifugation. The supernatant of Part 1A or 2A respectively and Part 1B or 2B respectively of the reaction mixture can subsequently be analysed by denaturating acrylamide gel electrophoresis, for example, followed by autoradiography of the acrylamide gel obtained. To quantify the amount of radioactively labeled proteins, which have been separated by means of acrylamide gel electrophoresis, the so-called "phospho-imaging" method, for example, known to the person skilled in the art, can be used. If the autoradiography or the analysis by means of the "phospho-imager" of proteins in the centrifugation supernatant of Part B of reaction mixture 1 shows a significantly increased signal compared with the centrifugation supernatant of Part A of reaction mixture 1, then this shows that a protein facilitating a phosphorylation of starch occurs as an autophosphorylated intermediate product. Parts A and B of reaction mixture 2 serve as a control and should therefore not exhibit a significantly increased signal in the centrifugation supernatant in the autoradiography or in the analysis by means of the "phospho-imager".

In addition, the starch of the respective Part A of reaction mixture 1 and 2 remaining in the respective sedimented pellet can be investigated, if necessary after subsequent washing of the respective starches, for the presence of starch phosphate, which has a label corresponding to the labeled ATP used. If the starches of Part A of reaction mixture 1 contain labeled phosphate residues, and if the autoradiography of the centrifugation supernatant of Part B of reaction mixture 1 shows a significantly increased signal in the autoradiography compared with the centrifugation supernatant of Part A of reaction mixture 1, then this shows that a phosphorylation of starch-facilitating protein is present as an autophosphorylated intermediate product. Parts A and B of reaction mixture 2 serve as a control and should therefore not exhibit a significantly increased signal for alpha-1,4-glucans labeled with $^{33}$P in the sedimented pellet containing alpha-1,4-glucans. Possible methods for demonstrating a phosphorylated OK1 protein intermediate product are described below under General Methods, Item 12 and in Example 7.

That an OK1 protein has an increased bonding activity to a P-starch compared with non-phosphorylated starch can be demonstrated by incubating the OK1 protein with P-starch and non-phosphorylated starch in separate preparations.

All non-phosphorylated starches are basically suitable for incubating OK1 proteins with non-phosphorylated starch. Preferably, a non-phosphorylated plant starch, particularly preferably wheat starch, and especially preferably granular leaf starch of an *Arabidopsis thaliana* mutant sex1-3 is used.

Methods for isolating starch from plants, for example, are known to the person skilled in the art. All methods known to the person skilled in the art are basically suitable for isolating non-phosphorylated starch from appropriate plant species. Preferably, the methods for isolating non-phosphorylated alpha-1,4-glucans described below are used (see General Methods Item 2).

All starches, which contain starch phosphate, are basically suitable for incubating OK1 proteins with P-starch. Chemically phosphorylated starches can also be used for this purpose. Preferably, P-starches are used for the incubation with OK1 proteins, particularly preferably a retrospectively enzymatically phosphorylated plant starch, especially preferably a retrospectively enzymatically phosphorylated plant starch, which has been isolated from a sex-1 mutant of *Arabidopsis thaliana*.

To demonstrate an increased bonding activity of OK1 proteins to P-starch compared with non-phosphorylated starch, OK1 proteins are incubated in separate preparations with P-starch (Preparation A) and with non-phosphorylated starch (Preparation B). On completion of the incubation, the proteins, which are not bonded to the respective starches of Preparations A and B, are separated from the starches and from the proteins bonded to them. The bond between the proteins and the P-starch in Preparation A and the bond between the proteins and non-phosphorylated starch in Preparation B are subsequently removed, i.e. the respective proteins are dissolved. The dissolved proteins of Preparation A and Preparation B can then be separated from the starches concerned, which are present in the respective preparations. Following this, the isolated P-starch bonding proteins of Preparation A and the isolated non-phosphorylated starch bonding proteins of Preparation B can be separated with the help of methods known to the person skilled in the art such as, for example, gel filtration, chromatographic methods, electrophoresis, SDS acrylamide gel electrophoresis etc. By comparing the amounts of separated proteins of Preparation A with the amounts of corresponding separated proteins of Preparation B, it can be determined whether a protein has an increased bonding activity with respect to P-starch compared with non-phosphorylated starch. Methods, which can be used to demonstrate a preferred bonding of proteins to P-starch compared with non-phosphorylated starch, are described below in Example 6.

The amino acid sequence shown in SEQ ID NO 2 codes an OK1 protein from *Arabidopsis thaliana* and the amino acid sequence shown under SEQ ID NO 4 codes an OK1 protein from *Oryza sativa*.

In a further embodiment of the present invention, amino acid sequences coding an OK1 protein have an identity of at least 60% with the sequence specified in SEQ ID NO 2 or SEQ ID NO 4, in particular of at least 70%, preferably of at least 80% and particularly preferably of at least 90% and especially preferably of at least 95%.

In a further embodiment of the present invention, the OK1 protein has a phosphohistidine domain (Tien-Shin Yu et al., 2001, Plant Cell 13, 1907-1918). Amino acid sequences coding OK1 proteins contain a phosphohistidine domain, which has an identity of at least 50% with the amino acid sequence of the phosphohistidine domain of the OK1 protein from *Arabidopsis thaliana* and *Oryza sativa* specified under SEQ ID NO 5, in particular of at least 60%, preferably of at least 70% and particularly preferably of at least 80% and especially preferably of at least 90%.

In a further embodiment the present invention relates to an OK1 protein, which has a phosphohistidine domain. The phosphohistidine domain preferably contains two histidine residues.

A further embodiment of the present invention relates to a genetically modified plant cell according to the invention or a genetically modified plant according to the invention, wherein the genetic modification consists in the introduction of at least one foreign nucleic acid molecule into the genome of the plant.

In this context, the term "genetic modification" means the introduction of homologous and/or heterologous foreign nucleic acid molecules into the genome of a plant cell or into the genome of a plant, wherein said introduction of these molecules leads to a reduction of the activity of an OK1 protein.

The plant cells according to the invention or plants according to the invention are modified with regard to their genetic information by the introduction of a foreign nucleic acid molecule. The presence or the expression of the foreign nucleic acid molecule leads to a phenotypic change. Here, "phenotypic change" means preferably a measurable change of one or more functions of the cells. For example, the genetically modified plant cells according to the invention and the genetically modified plants according to the invention exhibit a reduction of the activity of an OK1 protein due to the presence or on the expression of the introduced nucleic acid molecule.

In conjunction with the present invention, the term "foreign nucleic acid molecule" is understood to mean such a molecule that either does not occur naturally in the corresponding wild type plant cells, or that does not occur naturally in the concrete spatial arrangement in wild type plant cells, or that is localised at a place in the genome of the wild type plant cell at which it does not occur naturally. Preferably, the foreign nucleic acid molecule is a recombinant molecule, which consists of different elements, the combination or specific spatial arrangement of which does not occur naturally in plant cells.

In principle, the foreign nucleic acid molecule can be any nucleic acid molecule, which effects an increase in the activity of an OK1 protein in the plant cell or plant.

In conjunction with the present invention, the term "genome" is to be understood to mean the totality of the genetic material present in a plant cell. It is known to the person skilled in the art that, as well as the cell nucleus, other compartments (e.g. plastids, mitochondrions) also contain genetic material.

In a further embodiment, the plant cells according to the invention and the plants according to the invention are characterised in that the foreign nucleic acid molecule codes an OK1 protein, preferably an OK1 protein from *Arabidopsis thaliana* or an OK1 protein from *Oryza sativa*.

In a further embodiment, the foreign nucleic acid molecule codes an OK1 protein with the amino acid sequence specified in SEQ ID NO 2 or SEQ ID NO 4.

A large number of techniques are available for the introduction of DNA into a plant host cell. These techniques include the transformation of plant cells with T-DNA using *Agrobacterium tumefaciens* or *Agrobacterium rhizogenes* as the transformation medium, the fusion of protoplasts, injection, the electroporation of DNA, the introduction of DNA by means of the biolistic approach as well as other possibilities.

The use of *agrobacteria*-mediated transformation of plant cells has been intensively investigated and adequately described in EP 120516; Hoekema, Ind.: The Binary Plant Vector System Offsetdrukkerij Kanters B. V., Alblasserdam (1985), Chapter V; Fraley et al., Crit. Rev. Plant Sci. 4, 1-46 and by An et al. EMBO J. 4, (1985), 277-287. For the transformation of potato, see Rocha-Sosa et al., EMBO J. 8, (1989), 29-33, for example.

The transformation of monocotyledonous plants by means of vectors based on *Agrobacterium* transformation has also been described (Chan et al., Plant Mol. Biol. 22, (1993), 491-506; Hiei et al., Plant J. 6, (1994) 271-282; Deng et al, Science in China 33, (1990), 28-34; Wilmink et al., Plant Cell Reports 11, (1992), 76-80; May et al., Bio/Technology 13, (1995), 486-492; Conner and Domisse, Int. J. Plant Sci. 153 (1992), 550-555; Ritchie et al, Transgenic Res. 2, (1993), 252-265). An alternative system to the transformation of monocotyledonous plants is transformation by means of the biolistic approach (Wan and Lemaux, Plant Physiol. 104, (1994), 37-48; Vasil et al., Bio/Technology 11 (1993), 1553-1558; Ritala et al., Plant Mol. Biol. 24, (1994), 317-325; Spencer et al., Theor. Appl. Genet. 79, (1990), 625-631), protoplast transformation, electroporation of partially permeabilised cells and the introduction of DNA by means of glass fibres. In particular, the transformation of maize has been described in the literature many times (cf. e.g. WO95/06128, EP0513849, EP0465875, EP0292435; Fromm et al., Biotechnology 8, (1990), 833-844; Gordon-Kamm et al., Plant Cell 2, (1990), 603-618; Koziel et al., Biotechnology 11 (1993), 194-200; Moroc et al., Theor. Appl. Genet. 80, (1990), 721-726).

The successful transformation of other types of cereal has also already been described, for example for barley (Wan and Lemaux, see above; Ritala et al., see above; Krens et al., Nature 296, (1982), 72-74) and for wheat (Nehra et al., Plant J. 5, (1994), 285-297; Becker et al., 1994, Plant Journal 5, 299-307). All the above methods are suitable within the framework of the present invention.

Amongst other things, plant cells and plants, which have been genetically modified by the introduction of an OK1 protein, can be differentiated from wild type plant cells and wild type plants respectively in that they contain a foreign nucleic acid molecule, which does not occur naturally in wild type plant cells or wild type plants, or in that such a molecule is present integrated at a place in the genome of the plant cell according to the invention or in the genome of the plant according to the invention at which it does not occur in wild type plant cells or wild type plants, i.e. in a different genomic environment. Furthermore, plant cells according to the invention and plants according to the invention of this type differ from wild type plant cells and wild type plants respectively in that they contain at least one copy of the foreign nucleic acid molecule stably integrated within their genome, possibly in addition to naturally occurring copies of such a molecule in the wild type plant cells or wild type plants. If the foreign nucleic acid molecule(s) introduced into the plant cells according to the invention or into the plants according to the invention is (are) additional copies of molecules already occurring naturally in the wild type plant cells or wild type plants respectively, then the plant cells according to the invention and the plants according to the invention can be differentiated from wild type plant cells or wild type plants respectively in particular in that this additional copy or these additional copies is (are) localised at places in the genome at which it does not occur (or they do not occur) in wild type plant cells or wild type plants. This can be verified, for example, with the help of a Southern blot analysis.

Furthermore, the plant cells according to the invention and the plants according to the invention can preferably be differentiated from wild type plant cells or wild type plants respectively by at least one of the following characteristics: If the foreign nucleic acid molecule that has been introduced is heterologous with respect to the plant cell or plant, then the plant cells according to the invention or plants according to the invention have transcripts of the introduced nucleic acid molecules. These can be verified, for example, by Northern blot analysis or by RT-PCR (Reverse Transcription Polymerase Chain Reaction). Plant cells according to the invention and plants according to the invention, which express an antisense and/or an RNAi transcript, can be verified, for example, with the help of specific nucleic acid probes, which are complimentary to the RNA (occurring naturally in the plant cell), which is coding for the protein. Preferably, the plant cells according to the invention and the plants according to the invention contain a protein, which is coded by an introduced nucleic acid molecule. This can be demonstrated by immunological methods, for example, in particular by a Western blot analysis.

If the foreign nucleic acid molecule that has been introduced is homologous with respect to the plant cell or plant, the plant cells according to the invention or plants according to the invention can be differentiated from wild type plant cells or wild type plants respectively due to the additional expression of the introduced foreign nucleic acid molecule, for example. The plant cells according to the invention and the plants according to the invention preferably contain transcripts of the foreign nucleic acid molecules. This can be demonstrated by Northern blot analysis, for example, or with the help of so-called quantitative PCR.

In a further embodiment, the plant cells according to the invention and the plants according to the invention are transgenic plant cells or transgenic plants respectively.

In a further embodiment, the plant cells according to the invention and the plants according to the invention are characterised in that at least one foreign nucleic acid molecule codes amino acid sequences, which are included in an amino acid sequence, which codes an OK1 protein.

In a further embodiment, the present invention relates to plant cells according to the invention and plants according to the invention wherein the foreign nucleic acid molecule is chosen from the group consisting of
a) Nucleic acid molecules, which code a protein with the amino acid sequence given under SEQ ID NO 2 or SEQ ID NO 4;
b) Nucleic acid molecules, which code a protein, which includes the amino acid sequence, which is coded by the insertion in plasmid A.t.-OK1-pGEM or the insertion in plasmid pMI50;
c) Nucleic acid molecules, which code a protein, the sequence of which has an identity of at least 60% with the amino acid sequence given under SEQ ID NO 2 or SEQ ID NO 4;
d) Nucleic acid molecules, which code a protein, the sequence of which has an identity of at least 60% with the amino acid sequence, which is coded by the coding region of the insertion in plasmid A.t.-OK1-pGEM or by the coding region of the insertion in plasmid pMI50;
e) Nucleic acid molecules, which include the nucleotide sequence shown under SEQ ID NO 1 or SEQ ID NO 3 or a complimentary sequence;
f) Nucleic acid molecules, which include the nucleotide sequence of the insertion contained in plasmid A.t.-OK1-pGEM or plasmid pMI50;
g) Nucleic acid molecules, which have an identity of at least 70% with the nucleic acid sequences described under a), b), d) or e);
h) Nucleic acid molecules, which hybridise with at least one strand of the nucleic acid molecules described under a), b), e) or f) under stringent conditions;
i) Nucleic acid molecules, the nucleotide sequence of which deviates from the sequence of the nucleic acid molecules identified under a), b), e) or f) due to the degeneration of the genetic code; and
j) Nucleic acid molecules, which represent fragments, allelic variants and/or derivatives of the nucleic acid molecules identified under a), b), c), d), e), f), g), h) or i).

The amino acid sequence shown in SEQ ID NO 2 codes an OK1 protein from *Arabidopsis thaliana* and the amino acid sequence shown in SEQ ID NO 4 codes an OK1 protein from *Oryza sativa*.

The proteins coded from the different varieties of nucleic acid molecules according to the invention have certain common characteristics. These can include, for example, biological activity, molecular weight, immunological reactivity, conformation etc, as well as physical characteristics such as, for example, the running behaviour in gel electrophoresis, chromatographic behaviour, sedimentation coefficients, solubility, spectroscopic characteristics, stability; optimum pH, optimum temperature etc.

The molecular weight of the OK1 protein from *Arabidopsis thaliana* derived from the amino acid sequence shown under SEQ ID NO 2 is ca. 131 kDa and the molecular weight of the OK1 protein from *Oryza sativa* derived from the amino acid sequence shown under SEQ ID NO 4 is ca. 132 kDa. The derived molecular weight of a protein according to the invention therefore preferably lies in the range from 120 kDa to 145 kDa, preferably in the range from 120 kDa to 140 kDa, particularly preferably from 125 kDa to 140 kDa and especially preferably from 130 kDa to 135 kDa.

The amino acid sequences shown under SEQ ID NO 2 and SEQ ID NO 4 coding OK1 proteins from *Arabidopsis thaliana* and *Oryza sativa* respectively each contain a phosphohistidine domain. Preferably, an OK1 protein according to the invention therefore contains a phosphohistidine domain, which has an identity of at least 50%, preferably of at least 60%, particularly preferably of at least 80% and especially preferably of 90% with the phosphohistidine domain shown under SEQ ID NO 5.

The present invention relates to nucleic acid molecules, which code a protein with the enzymatic activity according to the invention of an OK1 protein, wherein the coded OK1 protein has an identity of at least 70%, preferably of at least 80%, particularly preferably of at least 90% and especially preferably of 95% with the amino acid sequence specified under SEQ ID NO 2 or SEQ ID NO 4.

The plasmid A.t.-OK1-pGEM containing a cDNA, which codes an OK1 protein from *Arabidopsis thaliana*, was deposited with the Deutsche Sammlung von Mikroorganismen and Zellkulturen GmbH, Mascheroder Weg 1b, 38124 Braunschweig, Germany, on 8 Mar. 2004 under the number DSM16264, and the plasmid pMI50, containing a cDNA, which codes an OK1 protein from *Oryza sativa*, was deposited on 24 Mar. 2004 under the number DSM16302, in accordance with the Budapest Treaty. The amino acid sequence shown in SEQ ID NO 2 can be derived from the coding region of the cDNA sequence integrated in plasmid A.t.-OK1-pGEM and codes for an OK1 protein from *Arabidopsis thaliana*. The amino acid sequence shown in SEQ ID NO 4 can be derived from the coding region of the cDNA sequence integrated in plasmid pMI50 and codes for an OK1 protein from *Oryza sativa*. The present invention therefore also relates to nucleic acid molecules, which code a protein with the enzymatic activity of an OK1 protein, which includes the amino acid sequence, which is coded by the insertion in plasmid A.t.-OK1-pGEM or by the insertion in plasmid pMI50, wherein the coded protein has an identity of at least 70%, preferably of at least 80%, particularly preferably of at least 90% and especially preferably of 95% with the amino acid sequence, which can be derived from the insertion in A.t.-OK1-pGEM or pMI50.

The nucleic acid sequence shown in SEQ ID NO 1 is a cDNA sequence, which includes the coding region for an OK1 protein from *Arabidopsis thaliana* and the nucleic acid sequence shown in SEQ ID NO 3 is a cDNA sequence, which includes the coding region for an OK1 protein from *Oryza sativa*.

The present invention therefore also relates to nucleic acid molecules, which code an OK1 protein and the coding region of the nucleotide sequences shown under SEQ ID NO 1 or SEQ ID NO 3 or sequences, which are complimentary thereto, nucleic acid molecules, which include the coding region of the nucleotide sequence of the insertion contained in plasmid A.t.-OK1-pGEM or in plasmid pMI50 and nucleic acid molecules, which have an identity of at least 70%, preferably of at least 80%, particularly preferably of at least 90% and especially preferably of at least 95% with the said nucleic acid molecules.

With the help of the sequence information of nucleic acid molecules according to the invention or with the help of a nucleic acid molecule according to the invention, it is possible for the person skilled in the art to isolate homologous sequences from other plant species, preferably from starch-storing plants, preferably from plant species of the genus *Oryza*, in particular *Oryza sativa* or from *Arabidopsis thaliana*. This can be carried out, for example, with the help of conventional methods such as the examination of cDNA or genomic banks with suitable hybridisation samples. The person skilled in the art knows that homologous sequences can also be isolated with the help of (degenerated) oligonucleotides and the use of PCR-based methods.

The examination of databases, such as are made available, for example, by EMBL (http://www.ebi.ac.uk/Tools/index.htm) or NCBI (National Center for Biotechnology Information, http://www.ncbi.nlm.nih.gov/), can also be used for identifying homologous sequences, which code for OK1 protein. In this case, one or more sequences are specified as a so-called query. This query sequence is then compared by means of statistical computer programs with sequences, which are contained in the selected databases. Such database queries (e.g. blast or fasta searches) are known to the person skilled in the art and can be carried out by various providers.

If such a database query is carried out, e.g. at the NCBI (National Center for Biotechnology Information, http://www.ncbi.nlm.nih.gov/), then the standard settings, which are specified for the particular comparison inquiry, should be used. For protein sequence comparisons (blastp), these are the following settings: Limit entrez=not activated; Filter=low complexity activated; Expect value=10; word size=3; Matrix=BLOSUM62; Gap costs: Existence=11, Extension=1.

For nucleic acid sequence comparisons (blastn), the following parameters could be set: Limit entrez=not activated; Filter=low complexity activated; Expect value=10; word size=11.

With such a database search, the sequences described in the present invention can be used as a query sequence in order to identify further nucleic acid molecules and/or proteins, which code an OK1 protein.

With the help of the described methods, it is also possible to identify and/or isolate nucleic acid molecules according to the invention, which hybridise with the sequence specified under SEQ ID NO 1 or under SEQ ID NO 3 and which code an OK1 protein.

Within the framework of the present invention, the term "hybridising" means hybridisation under conventional hybridisation conditions, preferably under stringent conditions such as, for example, are described in Sambrock et al., Molecular Cloning, A Laboratory Manual, 3rd edition (2001) Cold Spring Harbor Laboratory Press, Cold Spring Harbor, N.Y. ISBN: 0879695773, Ausubel et al., Short Protocols in Molecular Biology, John Wiley & Sons; 5th edition (2002), ISBN: 0471250929). Particularly preferably, "hybridising" means hybridisation under the following conditions:

Hybridisation Buffer:
    2×SSC; 10×Denhardt solution (Ficoll 400+PEG+BSA; Ratio 1:1:1); 0.1% SDS; 5 mM EDTA; 50 mM Na2HPO4; 250 µg/ml herring sperm DNA; 50 µg/ml tRNA;
or
    25 M sodium phosphate buffer pH 7.2; 1 mM EDTA; 7% SDS Hybridisation Temperature:
    T=65 to 68° C.
    Wash buffer: 0.1×SSC; 0.1% SDS
    Wash temperature: T=65 to 68° C.

In principle, nucleic acid molecules, which hybridise with the nucleic acid molecules according to the invention, can originate from any plant species, which codes an appropriate protein, preferably they originate from starch-storing plants, preferably from species of the (systematic) family Poacea, particularly preferably from *Oryza sativa*. Nucleic acid molecules, which hybridise with the molecules according to the invention, can, for example, be isolated from genomic or from cDNA libraries. The identification and isolation of nucleic acid molecules of this type can be carried out using the nucleic acid molecules according to the invention or parts of these molecules or the reverse complements of these molecules, e.g. by means of hybridisation according to standard methods (see, for example, Sambrook et al., Molecular Cloning, A Laboratory Manual, 3rd edition (2001) Cold Spring Harbor Laboratory Press, Cold Spring Harbor, N.Y. ISBN: 0879695773, Ausubel et al., Short Protocols in Molecular Biology, John Wiley & Sons; 5th edition (2002), ISBN: 0471250929) or by amplification using PCR.

Nucleic acid molecules, which exactly or essentially have the nucleotide sequence specified under SEQ ID NO 1 or SEQ ID NO 3 or parts of these sequences, can be used as hybridisation samples. The fragments used as hybridisation samples can also be synthetic fragments or oligonucleotides, which have been manufactured using established synthesising techniques and the sequence of which corresponds essentially with that of a nucleic acid molecule according to the invention. If genes have been identified and isolated, which hybridise with the nucleic acid sequences according to the invention, then a determination of this sequence and an analysis of the characteristics of the proteins coded by this sequence should be carried out in order to establish whether an OK1 protein is involved. Homology comparisons on the level of the nucleic acid or amino acid sequence and a determination of the enzymatic activity are particularly suitable for this purpose. The activity of an OK1 protein can take place, for example, as described above under General Methods item 11. A preferred bonding affinity to P-starch in comparison with non-phosphorylated starch, and autophosphorylation of an OK1 protein can be demonstrated using the methods already described above and under General Methods Items 8 and 12.

The molecules hybridising with the nucleic acid molecules according to the invention particularly include fragments, derivatives and allelic variants of the nucleic acid molecules according to the invention, which code an OK1 protein from plants, preferably from starch-storing plants, preferably from plant species of the genus *Oryza*, particularly preferably from *Oryza sativa* or *Arabidopsis thaliana*. In conjunction with the present invention, the term "derivative" means that the sequences of these molecules differ at one or more positions from the sequences of the nucleic acid molecules described above and have a high degree of identity with these sequences. Here, the deviation from the nucleic acid molecules described above can have come about, for example, due to deletion, addition, substitution, insertion or recombination.

In conjunction with the present invention, the term "identity" means a sequence identity over the whole length of the coding region of at least 60%, in particular an identity of at least 80%, preferably greater than 80%, particularly preferably greater than 90% and especially of at least 95%. In conjunction with the present invention, the term "identity" is to be understood to mean the number of amino acids/nucleotides (identity) corresponding with other proteins/nucleic acids, expressed as a percentage. Identity is preferably determined by comparing SEQ ID NO 2 or SEQ ID NO 4 for amino acids or SEQ. ID NO 1 or SEQ ID NO 3 for nucleic acids with other proteins/nucleic acids with the help of computer programs. If sequences that are compared with one another have different lengths, the identity is to be determined in such a way that the number of amino acids, which have the shorter sequence in common with the longer sequence, determines the percentage quotient of the identity. Preferably, identity is determined by means of the computer program ClustalW, which is well known and available to the public (Thompson et al., Nucleic Acids Research 22 (1994), 4673-4680). ClustalW is made publicly available by Julie Thompson (Thompson@EMBL-Heidelberg.DE) and Toby Gibson (Gibson@EMBL-Heidelberg.DE), European Molecular Biology Laboratory, Meyerhofstrasse 1, D 69117 Heidelberg, Germany. ClustalW can also be downloaded from different Internet sites, including the IGBMC (Institut de Génétique et de Biologie Moléculaire et Cellulaire, B.P.163, 67404 Illkirch Cedex, France; ftp://ftp-igbmc.u-strasbg.fr/pub/) and the EBI (ftp://ftp.ebi.ac.uk/pub/software/) as well as from all mirrored Internet sites of the EBI (European Bioinformatics Institute, Wellcome Trust Genome Campus, Hinxton, Cambridge CB10 1SD, UK).

Preferably, Version 1.8 of the ClustalW computer program is used to determine the identity between proteins according to the invention and other proteins. In doing so, the following parameters must be set: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOPGAP.

Preferably, Version 1.8 of the ClustalW computer program is used to determine the identity between the nucleotide sequence of the nucleic acid molecules according to the invention, for example, and the nucleotide sequence of other nucleic acid molecules. In doing so, the following parameters must be set:

KTUPLE=2, TOPDIAGS=4, PAIRGAP=5, DNAMATRIX: IUB, GAPOPEN=10, GAPEXT=5, MAXDIV=40, TRANSITIONS: unweighted.

Furthermore, identity means that functional and/or structural equivalence exists between the nucleic acid molecules concerned or the proteins coded by them. The nucleic acid molecules, which are homologous to the molecules described above and constitute derivatives of these molecules, are generally variations of these molecules, which constitute modifications, which execute the same biological function. At the same time, the variations can occur naturally, for example they can be sequences from other plant species, or they can be mutations, wherein these mutations may have occurred in a natural manner or have been introduced by objective mutagenesis. The variations can also be synthetically manufactured sequences. The allelic variants can be both naturally occurring variants and also synthetically manufactured variants or variants produced by recombinant DNA techniques. Nucleic acid molecules, which deviate from nucleic acid molecules according to the invention due to degeneration of the genetic code, constitute a special form of derivatives.

The proteins coded from the different derivatives of nucleic acid molecules according to the invention have certain common characteristics. These can include, for example, biological activity, substrate specificity, molecular weight, immunological reactivity, conformation etc, as well as physical characteristics such as, for example, the running behaviour in gel electrophoresis, chromatographic behaviour, sedimentation coefficients, solubility, spectroscopic characteristics, stability; optimum pH, optimum temperature etc. Preferred characteristics of an OK1 protein have already been described in detail above and are to be applied here accordingly.

The nucleic acid molecules according to the invention can be any nucleic acid molecules, in particular DNA or RNA molecules, for example cDNA, genomic DNA, mRNA etc. They can be naturally occurring molecules or molecules manufactured by genetic or chemical synthesis methods. They can be single-stranded molecules, which either contain the coding or the non-coding strand, or double-stranded molecules.

A further embodiment of the present invention relates to plant cells according to the invention and plants according to the invention wherein the foreign nucleic acid molecule is chosen from the group consisting of
a) DNA molecules, which code at least one antisense RNA, which effects a reduction in the expression of at least one endogenous gene, which codes an OK1 protein;
b) DNA molecules, which by means of a co-suppression effect lead to the reduction in the expression of at least one endogenous gene, which codes an OK1 protein;
c) DNA molecules, which code at least one ribozyme, which splits specific transcripts of at least one endogenous gene, which codes an OK1 protein;
d) DNA molecules, which simultaneously code at least one antisense RNA and at least one sense RNA, wherein the said antisense RNA and the said sense RNA form a double-stranded RNA molecule, which effects a reduction in the expression of at least one endogenous gene, which codes an OK1 protein (RNAi technology);
e) Nucleic acid molecules introduced by means of in vivo mutagenesis, which lead to a mutation or an insertion of a heterologous sequence in at least one endogenous gene coding an OK1 protein, wherein the mutation or insertion effects a reduction in the expression of a gene coding an OK1 protein or results in the synthesis of inactive OK1 proteins;
f) Nucleic acid molecules, which code an antibody, wherein the antibody results in a reduction in the activity of an OK1 protein due to the bonding to an OK1 protein,
g) DNA molecules, which contain transposons, wherein the integration of these transposons leads to a mutation or an insertion in at least one endogenous gene coding an OK1 protein, which effects a reduction in the expression of at least one gene coding an OK1 protein, or results in the synthesis of inactive OK1 proteins; and/or
h) T-DNA molecules, which, due to insertion in at least one endogenous gene coding an OK1 protein, effect a reduction in the expression of at least one gene coding an OK1 protein, or result in the synthesis of inactive OK1 protein.

The plant cells according to the invention and plants according to the invention can be manufactured by different methods known to the person skilled in the art. These include, for example, the expression of a corresponding antisense RNA or of a double-stranded RNA construct, the provision of molecules or vectors, which impart a cosuppression effect, the expression of a correspondingly constructed ribozyme that splits specific transcripts, which code an OK1 protein, or so-called "in vivo mutagenesis". Furthermore, the reduction of the OK1 protein activity in plant cells and plants can also be brought about by the simultaneous expression of sense and antisense RNA molecules of the respective target gene to be repressed, preferably of the OK1 gene.

In addition to this, it is known that in planta the formation of double-stranded RNA molecules of promoter sequences can lead in trans to methylation and transcriptional inactivation of homologous copies of this promoter (Mette et al., EMBO J. 19, (2000), 5194-5201).

A further possible way in which to reduce the enzymatic activity of proteins in plant cells or plants is the so-called immunomodulation method. It is known that an in planta expression of antibodies, which specifically recognise a plant protein, results in a reduction of the activity of the proteins concerned in appropriate plant cells due to the formation of a protein antibody complex (Conrad and Manteufel, Trends in Plant Science 6, (2001), 399-402; De Jaeger et al., Plant Molecular Biology 43, (2000), 419-428; Jobling et al., Nature Biotechnology 21, (2003), 77-80).

All these methods are based on the introduction of a foreign or of several foreign nucleic acid molecules into the genome of plant cells or plants and are therefore basically suitable for manufacturing plant cells according to the invention and plants according to the invention.

For inhibiting the expression of genes by means of antisense or cosuppression technology, a DNA molecule can be used, for example, which includes the whole coding sequence for an OK1 protein, including any existing flanking sequences, as well as DNA molecules, which include only parts of the coding sequence, whereby these parts must be long enough to produce an antisense effect or a cosuppression effect respectively in the cells. In general, sequences up to a minimum length of 21 bp, preferably a minimum length of at least 100 bp, particularly preferably of at least 500 bp are suitable. For example, the DNA molecules have a length of 21-100 bp, preferably of 100-500 bp, particularly preferably over 500 bp.

The use of DNA sequences, which have a high degree of identity with the endogenous sequences occurring in the plant cell and which code OK1 proteins, is also suitable for antisense or cosuppression preparations. The minimum identity should be greater than ca. 65%, preferably greater than 80%. The use of sequences with identities of at least 90%, in particular between 95% and 100%, is to be preferred. The meaning of the term "identity" is defined elsewhere.

Furthermore, the use of introns, i.e. of non-coding areas of genes, which code for OK1 proteins, is also conceivable for achieving an antisense or a cosuppression effect.

The use of intron sequences for inhibiting the gene expression of genes, which code for starch biosynthesis proteins, has been described in the international patent applications WO97/04112, WO97/04113, WO98/37213, WO98/37214.

The person skilled in the art knows how to achieve an antisense and a cosuppression effect. For example, the method of cosuppression inhibition has been described in Jorgensen (Trends Biotechnol. 8 (1990), 340-344), Niebel et al., (Curr. Top. Microbiol. Immunol. 197 (1995), 91-103), Flavell et al. (Curr. Top. Microbiol. Immunol. 197 (1995), 43-46), Palaqui and Vaucheret (Plant. Mol. Biol. 29 (1995), 149-159), Vaucheret et al., (Mol. Gen. Genet. 248 (1995), 311-317), de Borne et al. (Mol. Gen. Genet. 243 (1994), 613-621).

The expression of ribozymes for reducing the activity of particular enzymes in cells is also known to the person skilled in the art, and is described, for example, in EP-B1 0321201. The expression of ribozymes in plant cells has been described, for example, in Feyter et al. (Mol. Gen. Genet. 250, (1996), 329-338).

The reduction of the activity of an OK1 protein in plant cells according to the invention and plants according to the invention can also be brought about by the simultaneous expression of sense and antisense RNA molecules (RNAi technology) of the respective target gene to be repressed, preferably of the OK1 protein gene.

This can be achieved, for example, by the use of chimeric constructs, which contain "inverted repeats" of the respective target gene or parts of the target gene. In this case, the generic constructs code for sense and antisense RNA molecules of the respective target gene. Sense and antisense RNA are synthesised simultaneously in planta as an RNA molecule, wherein sense and antisense RNA are separated from one another by a spacer, and are able to form a double-stranded RNA molecule.

It has been shown that the introduction of inverted repeat DNA constructs into the genome of plant cells or plants is a very effective method of repressing the genes corresponding to the inverted repeat DNA constructs (Waterhouse et al., Proc. Natl. Acad. Sci. USA 95, (1998), 13959-13964; Wang and Waterhouse, Plant Mol. Biol. 43, (2000), 67-82; Singh et al., Biochemical Society Transactions Vol. 28 part 6 (2000), 925-927; Liu et al., Biochemical Society Transactions Vol. 28 part 6 (2000), 927-929); Smith et al., (Nature 407, (2000), 319-320; international patent application WO99/53050 A1). Sense and antisense sequences of the target gene or of the target genes can also be expressed separately from one another by means of similar or different promoters (Nap, J-P et al, 6$^{th}$ International Congress of Plant Molecular Biology, Quebec, 18-24 Jun., 2000; Poster S7-27, Presentation Session S7).

The reduction of the activity of an OK1 protein in plant cells according to the invention or plants according to the invention can therefore also be achieved by producing double-stranded RNA molecules. In this regard, "inverted repeats" of DNA molecules of OK1 genes or cDNAs are preferably introduced into the genome of plants, wherein the DNA molecules (OK1 gene or cDNA or fragments of these genes or cDNAs) to be transcribed are under the control of a promoter, which controls the expression of said DNA molecules.

In addition to this, it is known that the formation of double-stranded RNA molecules from promoter DNA molecules in plants in trans can lead to methylation and transcriptional inactivation of homologous copies of these promoters, which are to be referred to in the following as target promoters (Mette et al., EMBO J. 19, (2000), 5194-5201).

It is therefore possible to reduce the gene expression of a particular target gene (e.g. OK1 gene), which is naturally under the control of this target promoter, by deactivating the target promoter.

This means that, in this case, the DNA molecules, which include the target promoters of the genes to be repressed (target genes), in contrast to the original function of promoters in plants, are not used as control elements for the expression of genes or cDNAs, but are themselves used as transcribable DNA molecules.

For the production of double-stranded target promoter RNA molecules in planta, which can occur there as RNA hairpin molecules, constructs are preferably used, which contain the "inverted repeats" of the target promoter DNA molecules, wherein the target promoter DNA molecules are under the control of a promoter, which controls the gene expression of said target promoter DNA molecules. These constructs are subsequently introduced into the genome of plants. The expression of the "inverted repeats" of said target promoter DNA molecules in planta leads to the formation of double-stranded target promoter RNA molecules (Mette et al., EMBO J. 19, (2000), 5194-5201). The target promoter can be inactivated by this means.

The reduction of the activity of an OK1 protein in plant cells according to the invention and plants according to the invention can therefore also be achieved by the production of double-stranded RNA molecules of promoter sequences of OK1 genes. In this regard, "inverted repeats" of promoter DNA molecules of OK1 genes are preferably introduced into the genome of plants, wherein the target promoter DNA molecules (promoter of an OK1 gene) to be transcribed are under the control of a promoter, which controls the expression of said target promoter DNA molecules.

For inhibiting the expression of genes by means of the simultaneous expression of sense and antisense RNA molecules (RNAi technology), a DNA molecule can be used, for example, which includes the whole coding sequence for an OK1 protein, including any existing flanking sequences, as well as DNA molecules, which include only parts of the coding sequence, whereby these parts must be long enough to produce a so-called RNAi effect in the cells. In general, sequences with a minimum length of 40 bp, preferably a minimum length of at least 100 bp, particularly preferably of at least 500 bp are suitable. For example, the DNA molecules have a length of 21-100 bp, preferably of 100-500 bp, particularly preferably greater then 500 bp.

The use of DNA sequences, which have a high degree of identity with the endogenous sequences occurring in the plant cells and which code an OK1 protein, is also suitable for the simultaneous expression of sense and antisense RNA molecules (RNAi technology). The minimum identity should be greater than ca. 65%, preferably greater than 80%. The use of sequences with identities of at least 90%, in particular between 95% and 100%, is to be particularly preferred. Sequences, which contain nucleic acid sequences, which code the phosphohistidine domains specified under SEQ ID NO 5, are particularly suitable for inhibiting OK1 genes by means of RNAi technology.

Furthermore, the reduction of the activity of an OK1 protein in plant cells according to the invention and plants according to the invention can also be achieved by so-called "in vivo mutagenesis", in which a hybrid RNA-DNA oligonucleotide ("Chimeroplast") is introduced into plant cells (Kipp, P. B. et al., Poster Session at the "5$^{th}$ International Congress of Plant Molecular Biology, 21-27 Sep. 1997, Singapore; R. A. Dixon and C. J. Arntzen, meeting report on "Metabolic Engineering in Transgenic Plants", Keystone Symposia, Copper Mountain, Colo., USA, TIBTECH 15, (1997), 441-447; international patent application WO 9515972; Kren et al., Hepatology 25, (1997), 1462-1468; Cole-Strauss et al., Science 273, (1996), 1386-1389; Beetham et al., 1999, PNAS 96, 8774-8778).

A part of the DNA components of the RNA-DNA oligonucleotide is homologous to a nucleic acid sequence of an endogenous OK1 gene, but, in comparison with the nucleic acid sequence of an endogenous OK1 gene, it has a mutation or contains a heterologous region, which is surrounded by the homologous regions.

By base pairing of the homologous regions of the RNA-DNA oligonucleotide and the endogenous nucleic acid molecule followed by homologous recombination, the mutation or heterologous region contained in the DNA components of the RNA-DNA oligonucleotide can be transferred into the genome of a plant cell. This leads to a reduction of the activity of one or more OK1 proteins.

The person skilled in the art knows that he can achieve a reduction of the activity of OK1 proteins by the expression of non-functional derivatives, in particular transdominant mutations, of such proteins, and/or by the expression of antagonists/inhibitors of such proteins.

Antagonist/inhibitors of such proteins include, for example, antibodies, antibody fragments or molecules with similar bonding characteristics. For example, a cytoplasmatic scFv antibody has been used to modulate the activity of the phytochrome A protein in genetically modified tobacco plants (Owen, Bio/Technology 10 (1992), 790-4; Review: Franken, E, Teuschel, U. and Hain, R., Current Opinion in Biotechnology 8, (1997), 411-416; Whitelam, Trends Plant Sci. 1 (1996), 268-272; Conrad and Manteufel, Trends in Plant Science 6, (2001), 399-402; De Jaeger et al., Plant Molecular Biology 43, (2000), 419-428). The reduction of the activity of a branching enzyme in potato plants by expressing a specific antibody has been described by Jobling et al. (Nature Biotechnology 21, (2003), 77-80). Here, the antibody was provided with a plastidiary target sequence so that the inhibition of proteins localised in plastids was guaranteed.

In conjunction with the present invention, plant cells and plants according to the invention can also be manufactured by the use of so-called insertion mutagenesis (overview article: Thorneycroft et al., 2001, Journal of experimental Botany 52 (361), 1593-1601). Insertion mutagenesis is to be understood to mean particularly the insertion of transposons or so-called transfer DNA (T-DNA) into a gene coding for an OK1 protein, whereby, as a result of which, the activity of an OK1 protein in the cell concerned is reduced.

The transposons can be both those that occur naturally in the cell (endogenous transposons) and also those that do not occur naturally in said cell but are introduced into the cell (heterologous transposons) by means of genetic engineering methods, such as transformation of the cell, for example. Changing the expression of genes by means of transposons is known to the person skilled in the art. An overview of the use of endogenous and heterologous transposons as tools in plant biotechnology is presented in Ramachandran and Sundaresan (2001, Plant Physiology and Biochemistry 39, 234-252). The possibility of identifying mutations in which specific genes have been inactivated by transposon insertion mutagenesis is presented in an overview by Maes et al. (1999, Trends in Plant Science 4 (3), 90-96). The production of rice mutants with the help of endogenous transposons is described by Hirochika (2001, Current Opinion in Plant Biology 4, 118-122). The identification of maize genes with the help of endogenous retrotransposons is presented, for example, by Hanley et al. (2000, The Plant Journal 22 (4), 557-566). The possibility of manufacturing mutants with the help of retrotransposons and methods of identifying mutants are described by Kumar and Hirochika (2001, Trends in Plant Science 6 (3), 127-134). The activity of technological transposons in different species has been described both for dicotyledonous and for monocotyledonous plants: e.g. for rice (Greco et al., 2001, Plant Physiology 125, 1175-1177; Liu et al., 1999, Molecular and General Genetics 262, 413-420; Hiroyuki et al., 1999, The Plant Journal 19 (5), 605-613; Jeon und Gynheung, 2001, Plant Science 161, 211-219), barley (2000, Koprek et al., The Plant Journal 24 (2), 253-263) *Arabidopsis thaliana* (Aarts et al., 1993, Nature 363, 715-717, Schmidt und Willmitzer, 1989, Molecular and General Genetics 220, 17-24; Altmann et al., 1992, Theoretical and Applied Genetics 84, 371-383; Tissier et al., 1999, The Plant Cell 11, 1841-1852), tomato (Belzile und Yoder, 1992, The Plant Journal 2 (2), 173-179) and potato (Frey et al., 1989, Molecular and General Genetics 217, 172-177; Knapp et al., 1988, Molecular and General Genetics 213, 285-290).

Basically, the plant cells according to the invention and the plants according to the invention can be manufactured both with the help of homologous and heterologous transposons, whereby the use of homologous transposons is also to be understood to mean those, which are naturally present in the corresponding wild type plant genome.

T-DNA insertion mutagenesis is based on the fact that certain sections (T-DNA) of Ti plasmids from *Agrobacterium* can integrate into the genome of plant cells. The place of integration in the plant chromosome is not defined, but can take place at any point. If the T-DNA integrates into a part of the chromosome, which constitutes a gene function, then this can lead to a change in the gene expression and thus also to a change in the activity of a protein coded by the gene concerned. In particular, the integration of a T-DNA into the coded area of a protein often leads to the corresponding protein no longer being able to be synthesised at all, or no longer synthesised in active form, by the cell concerned. The use of T-DNA insertions for producing mutants is described, for example, for *Arabidopsis thaliana* (Krysan et al., 1999, The Plant Cell 11, 2283-2290; Atipiroz-Leehan and Feldmann, 1997, Trends in genetics 13 (4), 152-156; Parinov and Sundaresan, 2000, Current Opinion in Biotechnology 11, 157-161) and rice (Jeon and An, 2001, Plant Science 161, 211-219; Jeon et al., 2000, The Plant Journal 22 (6), 561-570). Methods for identifying mutants, which have been produced with the help of T-DNA insertion mutagenesis, are described, amongst others, by Young et al., (2001, Plant Physiology 125, 513-518), Parinov et al. (1999, The Plant cell 11, 2263-2270), Thorneycroft et al. (2001, Journal of Experimental Botany 52, 1593-1601), and McKinney et al. (1995, The Plant Journal 8 (4), 613-622).

T-DNA mutagenesis is basically suitable for the production of the plant cells and plants according to the invention, which have a reduced activity of an OK1 protein.

T-DNA insertion mutants have been produced in great numbers for *Arabidopsis thaliana*, for example, and are made available by different culture collections ("Stock centre", e.g. Salk Institute Genomic Analysis Laboratory, 10010 N. Torrey Pines Road, La Jolla, Calif. 92037, http://signal.salk.edu/). The *Arabidopsis* mutant with the Acc. No.: SALK_110814 (alias N610814) contains a T-DNA insertion, which leads to a reduced activity of an OK1 protein in the mutant. With regard to growth and the speed of growth, these mutants behave like wild type plants but, in contrast to wild type plants, have a high starch phenotype.

Genetically modified *Arabidopsis thaliana* plants, transformed with an RNAi construct containing "inverted repeats" of the coding region of the OK1 protein from *Arabidopsis thaliana* (SEQ ID NO 1), showed a significantly reduced amount of OK1 protein in the Western blot analysis. These plants also showed a high starch phenotype and a normal growth in comparison with corresponding wild type plant cells.

The present invention therefore also relates to plant cells according to the invention and plants according to the invention, which have a high starch (starch excess) phenotype.

It was possible to demonstrate plant cells or plants, which have a high starch phenotype, by determining the amount of starch in individual plant parts (e.g. leaves) with the help of the methods known to the person skilled in the art. Thus, the starch content, for example, can be found with the help of enzymatically coupled photometric determination.

A further simple method of demonstrating a high starch phenotype is based on the colouring of plant parts with Lugol's solution. To do this, plant parts, preferably leaves, of mutants or genetically modified plants are incubated with Lugol's solution. In comparison with these, identical plant parts of wild type plants, which had grown up under the same conditions as the mutants or genetically modified plants concerned, were also incubated with Lugol's solution. Starch turns brownish to black with Lugol's solution. The stronger the coloration with Lugol's solution, the more starch is contained by the plant parts concerned. In order to be able to detect a clear difference between the wild type plants and the mutants or genetically modified plants, the plants concerned are first subjected to a dark phase before individual plant parts are stained with Lugol's solution, i.e. they are not exposed to light.

In conjunction with the present invention, the term "high starch phenotype" is to be understood to mean a mutant or a genetically modified plant, which has more starch in individual plant parts (e.g. leaves) than corresponding wild type plants. Preferably, mutants or genetically modified plants contain more starch in individual plant parts at the end of a dark phase than corresponding wild type plants. The dark phase can be 2 to 20 hours, preferably 4 to 16 hours, particularly preferably 6 to 14 and especially preferably 10 to 12 hours.

Surprisingly, it has been found that plant cells according to the invention and plants according to the invention synthesise a modified starch in comparison with starch of corresponding wild type plant cells or wild type plants that have not been genetically modified.

As no enzymes have previously been described, which exclusively phosphorylate P-starch, it has also previously not been possible to modify the distribution of starch phosphate in starch synthesised by plants. Due to the provision by the present invention of plants according to the invention, it is now also possible to modify the phosphate ratio in native starches.

The plant cells according to the invention and plants according to the invention synthesise a modified starch, which in its physical-chemical characteristics, in particular the amylose content or the amylose/amylopectin ratio, the phosphate ratio, the phosphate content, the viscosity behaviour, the gelling strength, the starch granule size and/or the starch granule morphology, is changed in comparison with the synthesised starch in wild type plant cells or plants, so that this is better suited for special applications.

The present invention therefore also includes plant cells according to the invention and plants according to the invention, which synthesise a modified starch.

Furthermore, genetically modified plants, which contain the plant cells according to the invention, are also the subject matter of the invention. Plants of this type can be produced from plant cells according to the invention by regeneration.

In principle, the plants according to the invention can be plants of any plant species, i.e. both monocotyledonous and dicotyledonous plants. Preferably they are useful plants, i.e. plants, which are cultivated by people for the purposes of food or for technical, in particular industrial purposes.

In a further embodiment, the plant according to the invention is a starch-storing plant.

In a further preferred embodiment, the present invention relates to a starch-storing plant according to the invention, which is a maize or wheat plant.

In conjunction with the present invention, the term "starch-storing plants" means all plants with plant parts, which contain a storage starch, such as, for example, maize, rice, wheat, rye, oats, barley, cassaya, potato, sago, mung bean, pea or sorghum.

In conjunction with the present invention, the term "wheat plant" means plant species of the genus *Triticum* or plants resulting from crosses with plants of the genus *Triticum*, particularly plant species of the genus *Triticum* or plants resulting from crosses with plants of the genus *Triticum*, which are used in agriculture for commercial purposes, particularly preferably *Triticum aestivum*.

In conjunction with the present invention, the term "maize plant" means plant species of the genus *Zea*, particularly plant species of the genus *Zea*, which are used in agriculture for commercial purposes, particularly preferably *Zea mais*.

The present invention also relates to propagation material of plants according to the invention containing a plant cell according to the invention.

Here, the term "propagation material" includes those constituents of the plant that are suitable for producing offspring by vegetative or sexual means. Cuttings, callus cultures, rhizomes or tubers, for example, are suitable for vegetative propagation. Other propagation material includes, for example, fruits, seeds, seedlings, protoplasts, cell cultures, etc. Preferably, the propagation material is tubers and particularly preferably granules, which contain endosperms.

In a further embodiment, the present invention relates to harvestable plant parts of plants according to the invention such as fruits, storage roots, roots, blooms, buds, shoots or stems, preferably seeds, grains or tubers, wherein these harvestable parts contain plant cells according to the invention.

Furthermore, the present invention also relates to a method for the manufacture of a genetically modified plant according to the invention, wherein a) a plant cell is genetically modified, whereby the genetic modification leads to the reduction of the activity of an OK1 protein in comparison with corresponding wild type plant cells that have not been genetically modified;
b) a plant is regenerated from plant cells from Step a); and
c) if necessary, further plants are produced with the help of the plants according to Step b).

The genetic modification introduced into the plant cell according to Step a) can basically be any type of genetic modification, which leads to the reduction of the activity of an OK1 protein.

The regeneration of the plants according to Step (b) can be carried out using methods known to the person skilled in the art (e.g. described in "Plant Cell Culture Protocols", 1999, edt. by R. D. Hall, Humana Press, ISBN 0-89603-549-2).

The production of further plants according to Step (c) of the method according to the invention can be carried out, for example, by vegetative propagation (for example using cuttings, tubers or by means of callus culture and regeneration of whole plants) or by sexual propagation. Here, sexual propagation preferably takes place under controlled conditions, i.e. selected plants with particular characteristics are crossed and propagated with one another. In this case, the selection is preferably carried out in such a way that further plants, which are obtained in accordance with Step c), exhibit the genetic modification, which was introduced in Step a).

In a further embodiment of the method according to the invention, the genetic modification consists in the introduction of a foreign nucleic acid molecule into the genome of the plant cell, wherein the presence or the expression of said foreign nucleic acid molecule leads to a reduced activity of an OK1 protein in the cell.

In a further embodiment of the method according to the invention, the genetic modification consists in the introduction of a foreign nucleic acid molecule, wherein the foreign nucleic acid molecule codes amino acid sequences, which are included in an amino acid sequence, which code an OK1 protein.

In a further embodiment, the method according to the invention is used for manufacturing a genetically modified plant according to the invention for producing starch-storing plants.

In a further embodiment, the method according to the invention is used for producing maize or wheat plants according to the invention.

In a further embodiment of the method according to the invention, the genetic modification consists in the introduction of a foreign nucleic acid molecule, wherein the foreign nucleic acid molecule is chosen from the group consisting of a) Nucleic acid molecules, which code a protein with the amino acid sequence specified under SEQ ID NO 2 or SEQ ID NO 4;
b) Nucleic acid molecules, which code a protein, the amino acid sequence of which has an identity of at least 60% with the amino acid sequence specified under SEQ ID NO 2 or SEQ ID NO 4;

c) Nucleic acid molecules, which include the nucleotide sequence shown under SEQ ID NO 1 or SEQ ID NO 3 or a complimentary sequence;
d) Nucleic acid molecules, the nucleic acid sequence of which has an identity of at least 60% with the nucleic acid sequences described under a) or c);
e) Nucleic acid molecules, which hybridise with at least one strand of the nucleic acid molecules described under a) or c) under stringent conditions;
f) Nucleic acid molecules, the nucleotide sequence of which deviates from the sequence of the nucleic acid molecules identified under a), b), c), d), e) or f) due to the degeneration of the genetic code; and
g) Nucleic acid molecules, which represent fragments, allelic variants and/or derivatives of the nucleic acid molecules identified under a), b), c), d), e) or f).

In a further embodiment of the method according to the invention, the genetic modification consists in the introduction of a foreign nucleic acid molecule, wherein the foreign nucleic acid molecule is chosen from the group consisting of
a) DNA molecules, which code at least one antisense RNA, which effects a reduction in the expression of at least one endogenous gene, which codes an OK1 protein;
b) DNA molecules, which by means of a co-suppression effect lead to the reduction in the expression of at least one endogenous gene, which codes an OK1 protein;
c) DNA molecules, which code at least one ribozyme, which splits specific transcripts of at least one endogenous gene, which codes an OK1 protein;
d) DNA molecules, which simultaneously code at least one antisense RNA and at least one sense RNA, wherein the said antisense RNA and the said sense RNA form a double-stranded RNA molecule, which effects a reduction in the expression of at least one endogenous gene, which codes an OK1 protein (RNAi technology);
e) Nucleic acid molecules introduced by means of in vivo mutagenesis, which lead to a mutation or an insertion of a heterologous sequence in at least one endogenous gene coding an OK1 protein, wherein the mutation or insertion effects a reduction in the expression of a gene coding an OK1 protein or results in the synthesis of inactive OK1 protein;
f) Nucleic acid molecules, which code an antibody, wherein the antibody results in a reduction in the activity of an OK1 protein due to the bonding to an OK1 protein,
g) DNA molecules, which contain transposons, wherein the integration of these transposons leads to a mutation or an insertion in at least one endogenous gene coding an OK1 protein, which effects a reduction in the expression of at least one gene coding an OK1 protein, or results in the synthesis of inactive OK1 proteins; and/or
h) T-DNA molecules, which, due to insertion in at least one endogenous gene coding an OK1 protein, effect a reduction in the expression of at least one gene coding an OK1 protein, or result in the synthesis of inactive OK1 protein.

In a further embodiment, the present invention relates to a method according to the invention, wherein the genetically modified plant synthesises a modified starch in comparison with starch from wild type plants that have not been genetically modified.

In a further embodiment of the method according to the invention, the plants according to the invention synthesise a modified starch, which has a lower starch phosphate content and/or a modified phosphate distribution in comparison with starch isolated from corresponding wild type plants.

In a further embodiment of the method according to the invention, the plants according to the invention synthesise a modified starch, which has a modified ratio of C-3 phosphate to C-6 phosphate in comparison with starch from wild type plants that have not been genetically modified. Particularly preferred here are starches, which have a reduced proportion of starch phosphate bonded in the C-3 position compared with starch phosphate bonded in the C-6 position in comparison with starches from wild type plants that have not been genetically modified.

The present invention also relates to the plants obtainable by the method according to the invention.

It is also an object of the present invention to provide means such as DNA molecules, for example, for the production of plant cells according to the invention and plants according to the invention, which synthesise a modified starch in comparison with modified wild type plant cells or wild type plants that have not been genetically modified.

The present invention therefore also relates to recombinant nucleic acid molecules containing a promoter, which initiates transcription in plant cells, and at least one nucleic acid sequence chosen from the group consisting of
a) Nucleic acid sequences, which code at least one antisense RNA, which effects a reduction in the expression of at least one endogenous gene, which codes an OK1 protein;
b) Nucleic acid sequences, which by means of a co-suppression effect lead to the reduction in the expression of at least one endogenous gene, which codes an OK1 protein;
c) Nucleic acid sequences, which code at least one ribozyme, which splits specific transcripts of at least one endogenous gene, which codes an OK1 protein, and
d) Nucleic acid sequences, which simultaneously code at least one antisense RNA and at least one sense RNA, wherein the said antisense RNA and the said sense RNA form a double-stranded RNA molecule, which effects a reduction in the expression of at least one endogenous gene, which codes an OK1 protein (RNAi technology).

In conjunction with the present invention, the term "recombinant nucleic acid molecule" is to be understood to mean a nucleic acid molecule, which as well as nucleic acid molecules according to the invention contains additional sequences, which do not occur naturally in a combination such as occurs in recombinant nucleic acids according to the invention. At the same time, the said additional sequences can be any sequences, preferably regulatory sequences (promoters, termination signals, enhancers), particularly preferably regulatory sequences, which are active in plant tissue, particularly preferably regulatory sequences, which are active in plant tissue in which storage starch is synthesised. Methods for producing recombinant nucleic acid molecules according to the invention are known to the person skilled in the art and include genetic engineering methods such as, for example, the linking of nucleic acid molecules by ligation, genetic recombination or the resynthesis of nucleic acid molecules (see, for example, Sambrook et al., Molecular Cloning, A Laboratory Manual, 3rd edition (2001) Cold Spring Harbour Laboratory Press, Cold Spring Harbour, N.Y. ISBN: 0879695773, Ausubel et al., Short Protocols in Molecular Biology, John Wiley & Sons; 5th edition (2002), ISBN: 0471250929).

Regulatory sequences for expression in prokaryotic organisms (promoters), e.g. *E. coli*, and in eukaryotic organisms are adequately described in the literature, in particular those for expression in yeast such as *Saccharomyces cerevisiae*, for example. An overview of different expression systems for proteins in different host organisms can be found, for example, in Methods in Enzymology 153 (1987), 383-516 and in Bitter et al. (Methods in Enzymology 153 (1987), 516-544).

For expressing nucleic acid molecules according to the invention, these are preferably linked with regulatory DNA sequences, which initiate transcription in plant cells (promoters). At the same time, the promoter can be chosen so that expression takes place constitutively or only in a certain tissue, at a certain stage of the plant development or at a time determined by external influences. The promoter can be homologous or heterologous both with respect to the plant and with respect to the nucleic acid molecule.

Suitable promoters are, for example, the promoter of the 35S RNA of the cauliflower mosaic virus and the ubiquitin promoter from maize for constitutive expression, the patatin promoter B33 (Rocha-Sosa et al., EMBO J. 8 (1989), 23-29) for tuber-specific expression in potatoes or a promoter, which only ensures expression in photosynthetically active tissues, e.g. the ST-LS1 promoter (Stockhaus et al., Proc. Natl. Acad. Sci. USA 84 (1987), 7943-7947; Stockhaus et al., EMBO J. 8 (1989), 2445-2451) or, for endosperm-specific expression of the HMG promoter from wheat, the USP promoter, the phaseolin promoter, promoters of zein genes from maize (Pedersen et al., Cell 29 (1982), 1015-1026; Quatroccio et al., Plant Mol. Biol. 15 (1990), 81-93), glutelin promoter (Leisy et al., Plant Mol. Biol. 14 (1990), 41-50; Zheng et al., Plant J. 4 (1993), 357-366; Yoshihara et al., FEBS Lett. 383 (1996), 213-218) or shrunken-1 promoter (Werr et al., EMBO J. 4 (1985), 1373-1380). However, promoters can also be used, which are only activated at a time determined by external influences (see for example WO 9307279). Promoters of heat-shock proteins, which allow simple induction, can be of particular interest here. Furthermore, seed-specific promoters can be used, such as the USP promoter from *Vicia faba*, which guarantees seed-specific expression in *Vicia faba* and other plants (Fiedler et al., Plant Mol. Biol. 22 (1993), 669-679; Bäumlein et al., Mol. Gen. Genet. 225 (1991), 459-467).

The recombinant nucleic acid molecule can also contain a termination sequence (polyadenylation signal), which is used for adding a poly-A tail to the transcript. A function in the stabilisation of the transcripts is ascribed to the poly-A tail. Elements of this type are described in the literature (cf. Gielen et al., EMBO J. 8 (1989), 23-29) and can be exchanged at will.

Intron sequences can also be present between the promoter and the coding region. Such intron sequences can lead to stability of expression and to increased expression in plants (Callis et al., 1987, Genes Devel. 1, 1183-1200; Luehrsen, and Walbot, 1991, Mol. Gen. Genet. 225, 81-93; Rethmeier, et al., 1997; Plant Journal. 12(4): 895-899; Rose and Beliakoff, 2000, Plant Physiol. 122 (2), 535-542; Vasil et al., 1989, Plant Physiol. 91, 1575-1579; XU et al., 2003, Science in China Series C Vol. 46 No. 6, 561-569). Suitable intron sequences are, for example, the first intron of the sh1 gene from maize, the first intron of the polyubiquitin gene 1 from maize, the first intron of the EPSPS gene from rice or one of the two first introns of the PAT1 gene from *Arabidopsis*.

A further embodiment of the present invention of recombinant nucleic acid molecules according to the invention comprises vectors, in particular plasmids, cosmids, viruses, bacteriophages and other common vectors in genetic engineering, which contain the nucleic acid molecules according to the invention described above.

A further subject of the present invention is a host cell, in particular a prokaryotic or eukaryotic cell, which is genetically modified with a recombinant nucleic acid molecule according to the invention and/or with a vector according to the invention, as well as cells, which originate from host cells of this type and which contain the genetic modification according to the invention.

In a further embodiment, the invention relates to host cells, in particular prokaryotic or eukaryotic cells, which have been transformed using a recombinant nucleic acid molecule according to the invention or a vector according to the invention, as well as host cells, which originate from host cells of this type and which contain the described nucleic acid molecules or vectors according to the invention.

It is preferred if the host cells according to the invention are plant cells. In principle, these can be plant cells from any plant species, i.e. both monocotyledonous and dicotyledonous plants. Preferably, these will be plant cells from useful agricultural plants, i.e. from plants, which are cultivated by people for the purposes of food or for technical, in particular industrial purposes. The invention relates preferably to plant cells and plants from starch-storing plants, preferably plant cells from the (systematic) family Poacea, especially particularly preferred are plant cells from maize or wheat plants.

Compositions containing a recombinant nucleic acid molecule according to the invention or a vector according to the invention are also the subject matter of the present invention. Compositions containing a recombinant nucleic acid molecule according to the invention and a host cell are preferred. It is particularly preferred if the host cell is a plant cell, and especially preferred if it is a cell of a maize or wheat plant.

A further aspect of compositions according to the invention relates to compositions, which can be used for producing host cells according to the invention, preferably for producing plant cells according to the invention. Preferably this concerns a compositions containing a recombinant nucleic acid molecule according to the invention or a vector according to the invention and a biolistic carrier, which is suitable for introducing a nucleic acid molecule according to the invention into a host cell. Preferred biolistic carriers are particles of tungsten, gold or synthetic materials.

A further embodiment of compositions according to the invention relates to compositions containing a recombinant nucleic acid molecule according to the invention or a vector according to the invention and a plant cell and a synthetic cultivation medium. Preferably, as well as nucleic acid molecules according to the invention, such compositions contain plant cells and synthetic cultivation medium comprising polyethylene glycol (PEG). With these compositions, the recombinant nucleic acid molecule exists outside the plant cell, i.e. it is situated outside the cell interior of the plant cell, which is enclosed by a cytoplasmic membrane.

Synthetic cultivation media, which are suitable for the cultivation and/or transformation of plant cells, are known to the person skilled in the art and are adequately described in the literature, for example. Many different synthetic cultivation media are also available for purchase in the specialised trade (e.g. DUCHEFA Biochemie B.V., Belgium).

Surprisingly, it has been found that starch isolated from plant cells according to the invention and plants according to the invention, which have a reduced activity of an OK1 protein, synthesise a modified starch.

In particular, the modified phosphate distribution accords the starches modified functional characteristics, which are of great interest in the paper industry, the cosmetics industry, the foodstuffs industry and the pharmaceutical industry.

The present invention also relates to modified starches obtainable from plant cells according to the invention or plants according to the invention, from propagation material according to the invention or from harvestable plant parts according to the invention.

In a further embodiment, the present invention relates to modified starch according to the invention from starch-storing plants, preferably from starch-storing plants of the (systematic) family Poaceae, particularly preferably from maize or wheat plants.

A further subject of the present invention relates to modified starch according to the invention, which has a modified ratio of C-6 phosphate to C-3 phosphate bonded to the starch in comparison with starch isolated from wild type plant cells or wild type plants respectively that have not been genetically modified. Preferably, the ratio of C-6 phosphate to C-3 phosphate bonded to the modified starch is increased. The increase of the ratio of C-6 phosphate to C-3 phosphate bonded to starch is preferably at least 5%, preferably at least 10%, particularly preferably at least 20% and especially preferably at least 30%.

Furthermore the present invention relates to a method for the manufacture of a modified starch including the step of extracting the starch from a plant cell according to the invention or from a plant according to the invention, from propagation material according to the invention of such a plant and/or from harvestable plant parts according to the invention of such a plant, preferably from starch-storing parts according to the invention of such a plant. Preferably, such a method also includes the step of harvesting the cultivated plants or plant parts and/or the propagation material of these plants before the extraction of the starch and, further, particularly preferably the step of cultivating plants according to the invention before harvesting.

Methods according to the invention for manufacturing modified starch for manufacturing a modified starch according to the invention are likewise subject matter of the present invention.

Methods for extracting starches from plants or from starch-storing parts of plants are known to the person skilled in the art. Furthermore, methods for extracting starch from different starch-storing plants are described, e.g. in Starch: Chemistry and Technology (Publisher: Whistler, BeMiller and Paschall (1994), 2nd Edition, Academic Press Inc. London Ltd; ISBN 0-12-746270-8; see e.g. Chapter XII, Page 412-468: Maize and *Sorghum* Starches: Manufacture; by Watson; Chapter XIII, Page 469-479: Tapioca, Arrowroot and Sago Starches: Manufacture; by Corbishley and Miller; Chapter XIV, Page 479-490: Potato starch: Manufacture and Uses; by Mitch; Chapter XV, Page 491 to 506: Wheat starch: Manufacture, Modification and Uses; by Knight and Oson; and Chapter XVI, Page 507 to 528: Rice starch: Manufacture and Uses; by Rohmer and Klem; Maize starch: Eckhoff et al., Cereal Chem. 73 (1996), 54-57, the extraction of maize starch on an industrial scale is generally achieved by so-called "wet milling".). Devices, which are in common use in methods for extracting starch from plant material, are separators, decanters, hydrocyclones, spray dryers and fluid bed dryers.

In conjunction with the present invention, the term "starch-storing parts" is to be understood to mean such parts of a plant in which, in contrast to transitory leaf starch, starch is stored as a deposit for surviving for longer periods. Preferred starch-storing plant parts are, for example, tubers, storage roots and grains, particularly preferred are grains containing an endosperm, especially particularly preferred are grains containing an endosperm of maize or wheat plants.

Modified starch obtainable by a method according to the invention for manufacturing modified starch is also the subject matter of the present invention.

In a further embodiment of the present invention, the modified starch according to the invention is native starch.

In conjunction with the present invention, the term "native starch" means that the starch is isolated from plants according to the invention, harvestable plant parts according to the invention, starch-storing parts according to the invention or propagation material of plants according to the invention by methods known to the person skilled in the art.

Furthermore, the use of plant cells according to the invention or plants according to the invention for manufacturing a modified starch are the subject matter of the present invention.

The person skilled in the art knows that the characteristics of starch can be changed by thermal, chemical, enzymatic or mechanical derivation, for example. Derived starches are particularly suitable for different applications in the foodstuffs and/or non-foodstuffs sector. The starches according to the invention are better suited as a starting substance for the manufacture of derived starches than conventional starches, as they have a higher proportion of reactive functional groups due to the higher starch phosphate content.

The present invention therefore also relates to the manufacture of a derived starch, wherein modified starch according to the invention is derived retrospectively.

In conjunction with the present invention, the term "derived starch" is to be understood to mean a modified starch according to the invention, the characteristics of which have been changed after isolation from plant cells with the help of chemical, enzymatic, thermal or mechanical methods.

In a further embodiment of the present invention, the derived starch according to the invention is starch that has been treated with heat and/or acid.

In a further embodiment, the derived starches are starch ethers, in particular starch alkyl ethers, O-allyl ethers, hydroxylalkyl ethers, O-carboxylmethyl ethers, nitrogen-containing starch ethers, phosphate-containing starch ethers or sulphur-containing starch ethers.

In a further embodiment, the derived starches are cross-linked starches.

In a further embodiment, the derived starches are starch graft polymers.

In a further embodiment, the derived starches are oxidised starches.

In a further embodiment, the derived starches are starch esters, in particular starch esters, which have been introduced into the starch using organic acids. Particularly preferably these are phosphate, nitrate, sulphate, xanthate, acetate or citrate starches.

The derived starches according to the invention are suitable for different applications in the pharmaceutical industry and in the foodstuffs and/or non-foodstuffs sector. Methods for manufacturing derived starches according to the invention are known to the person skilled in the art and are adequately described in the general literature. An overview on the manufacture of derived starches can be found, for example, in Orthoefer (in Corn, Chemistry and Technology, 1987, eds. Watson and Ramstad, Chapter 16, 479-499).

Derived starch obtainable by the method according to the invention for manufacturing a derived starch is also the subject matter of the present invention.

Furthermore, the use of modified starches according to the invention for manufacturing derived starch is the subject matter of the present invention.

DESCRIPTION OF SEQUENCES

SEQ ID NO 1: Nucleic acid sequence containing the coding region of the A.t.-OK1 protein from *Arabidopsis thaliana*. This sequence is inserted in the vectors OK1-pGEM and OK1-pDEST™17.

SEQ ID NO 2: Amino acid sequence coding the A.t.-OK1 protein from *Arabidopsis thaliana*. This sequence can be derived from the nucleic acid sequence shown under SEQ ID NO 1.

SEQ ID NO 3: Nucleic acid sequence containing the coding region of the O.s.-OK1 protein from *Oryza sativa*. This sequence is inserted in vector pMI50.

SEQ ID NO 4: Amino acid sequence coding the O.s.-OK1 protein from *Oryza sativa*. This sequence can be derived from the nucleic acid sequence shown under SEQ ID NO 3.

SEQ ID NO 5: Peptide sequence coding the phosphohistidine domain of the OK1 proteins from *Arabidopsis thaliana* and *Oryza sativa*.

SEQ ID NO 6: Peptide sequence containing the amino acid sequence coding an S.t.-OK1 protein from potato.

SEQ ID NO 7: Peptide sequence containing the amino acid sequence coding an S.t.-OK1 protein from potato.

SEQ ID NO 8: Peptide sequence containing the amino acid sequence coding an S.t.-OK1 protein from potato.

SEQ ID NO 9: Peptide sequence containing the amino acid sequence coding an S.t.-OK1 protein from potato.

SEQ ID NO 10: Partial nucleic acid sequence coding an S.t.-OK1 protein from potato. This nucleic acid sequence has been identified by means of the peptide sequences shown under SEQ ID NO 11, SEQ ID NO 12, SEQ ID NO 13 and SEQ ID NO 14 using the "Blast Search" facility in the TIGR database.

SEQ ID NO 11: Partial amino acid sequence coding an S.t.-OK1 protein from potato. The amino acid sequence shown can be derived from the nucleic acid sequence shown under SEQ ID NO 15.

DESCRIPTION OF FIGURES

FIG. 2 A) shows a denaturing (SDS) acrylamide gel on completion of electrophoresis stained with Coomassie Blue. FIG. 2 B) shows the autoradiography of a denaturing (SDS) acrylamide gel. The same amounts of the same samples were applied to each of the two gels. M: Standard protein molecular weight marker; R1: Sample from reaction vessel 1 according to Example 7 (after incubating an OK1 protein with ATP); R2: Sample from reaction vessel 2 according to Example 7 (after incubating an OK1 protein with ATP the protein was heated to 95° C.); R3: Sample from reaction vessel 3 according to Example 7 (after incubating an OK1 protein with ATP the protein was incubated in 0.5 M HCl); R4: Sample from reaction vessel 4 according to Example 7 (after incubating an OK1 protein with ATP the protein was incubated in 0.5 M NaOH).

FIG. 5 A) shows a Western blot. FIG. 5 B) shows the autoradiography of a denaturing (SDS) acrylamide gel. The same amounts of the same samples were applied to each of the two gels. The OK1 protein was incubated either with randomised radioactively labelled ATP or with ATP specifically radioactively labeled in the gamma position. On completion of incubation, the proteins were either heated to 30° C. or 95° C., or incubated in 0.5 M NaOH or 0.5 M HCl respectively.

GENERAL METHODS

Figure 1:
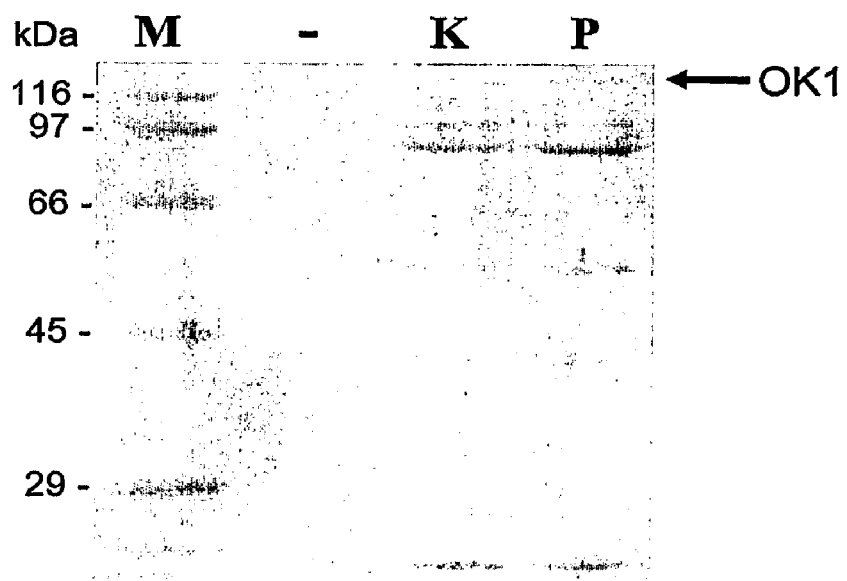
FIG. 1: Denaturing acrylamide gel for identifying proteins from *Arabidopsis thaliana*, which preferably bond to non-phosphorylated starch in comparison with phosphorylated starch. A standard protein molecular weight marker is shown in trace "M". Proteins obtained after incubation of control preparation C from Example 1d) are shown in trace "-". Protein extracts of *Arabidopsis thaliana*, obtained after incubation with non-phosphorylated starch, isolated from leaves of an *Arabidopsis thaliana* sex1-3 mutant (Preparation B, Example 1d)), are shown in trace "K". Protein extracts of *Arabidopsis thaliana*, obtained after incubation with starch, isolated from leaves of an *Arabidopsis thaliana* sex1-3 mutant, which was phosphorylated retrospectively in vitro with an R1 protein (Preparation A, Example 1 d)), are shown in trace "P". On completion of electrophoresis, the acrylamide gel was stained with Coomassie Blue.

In the following, methods are described, which can be used for carrying out the invention. These methods constitute specific embodiments of the present invention but do not restrict the present invention to these methods. The person skilled in the art knows that he can implement the invention in the same way by modifying the methods described and/or by replacing individual parts of the methods by alternative parts of the methods.

1. Manufacture of Protein Extracts from Plant Tissue a) Manufacture of Protein Extracts from Plant Tissues Leaf material is frozen in liquid nitrogen immediately after harvesting and subsequently homogenised in the mortar under liquid nitrogen. The reduced leaf material is mixed with ca. 3.5-times the volume (referred to the weight of the leaf material used) of cold (4° C.) binding buffer and broken down for 2×10 s with an Ultraturrax (maximum speed). After the first treatment with an Ultraturrax, the reduced leaf material is cooled on ice before the second treatment is carried out. The treated leaf material is then passed through a 100 μm nylon mesh and centrifuged for 20 min (50 ml centrifuge vessel, 20.000×g, 4° C.).

b) Precipitation of the Proteins Contained in the Protein Extracts

The supernatant obtained following centrifugation according to Step a) is removed and its volume determined. To precipitated proteins, ammonium sulphate is added continuously to the supernatant over a period of 30 minutes while stirring on ice down to a final concentration of 75% (weight/volume). The supernatant is subsequently incubated for a further hour on ice while stirring. The proteins precipitated from the supernatant are pelletised at 20.000×g and 4° C. for 10 min and the pellet subsequently absorbed in 5 ml of binding buffer, i.e. the proteins present in the pellet are dissolved.

c) Desalting of the Precipitated Proteins

The dissolved proteins are desalted by means of a PD10 column filled with Sephadex G25 (Amersham Bioscience, Freiburg, Prod. No. columns: 17-0851-01, Prod. No. Sephadex G25-M: 17-0033-01) at a temperature of 4° C., i.e. the ammonium sulphate used under Step b) for precipitation is also separated from the dissolved protein. The PD10 column is equilibrated with binding buffer before the proteins dissolved in accordance with Step b) are applied. For this purpose, 5 ml of binding buffer are spread over the column in each case. Subsequently, 2.5 ml of the protein solution obtained in accordance with Step b) are added to each column before proteins are eluted from the column with 3.5 ml binding buffer.

d) Determination of the Protein Concentration

The protein concentration is determined with a Bradford assay (Biorad, Munich, Prod. No. 500-0006 (Bradford, 1976, Anal. Biochem. 72, 248-254).

e) Composition of the binding buffer

| Binding buffer: 50 mM HEPES/NaOH (or KOH), pH 7.2 | |
|---|---|
| 1 mM | EDTA |
| 2 mM | Dithioerythritol (DTE) |
| 2 mM | Benzamidine |
| 2 mM | ε-aminocapronic acid |
| 0.5 mM | PMSF |
| 0.02% | Triton X-100 |

2. Isolation of Leaf Starch a) Isolation of Starch Granules from Plant Tissues Leaf material is frozen immediately after harvesting in liquid nitrogen. The leaf material is homogenised in portions in the mortar under liquid nitrogen and absorbed into a total of ca. 2.5-times the volume (weight/volume) of starch buffer. In addition, this suspension is again homogenised in the Waring blender for 20 s at maximum speed. The homogenate is passed through a nylon mesh (100 μm mesh width) and centrifuged for 5 minutes at 1.000×g. The supernatant with the soluble proteins is discarded.

b) Purification of the Starch Isolated from the Plant Tissues

After removing the green material lying on top of the starch by rinsing off the green material with starch buffer, the pellet containing the starch obtained from Step a) is absorbed in starch buffer and successively passed through nylon meshes with different mesh widths (in the order 60 μm, 30 μm, 20 μm). The filtrate is centrifuged using a 10 ml Percoll cushion (95% (v/v) Percoll (Pharmacia, Uppsala, Sweden), 5% (v/v) 0.5M HEPES-KOH pH7.2) (Correx tube, 15 min, 2.000×g). The sediment obtained after this centrifugation is resuspended once in starch buffer and centrifuged again (5 min, 1.000×g).

c) Removal of the Proteins Bonded to the Starch

Following Step b), starch granules are obtained, which contain proteins bonded to the starch. The proteins bonded to the surface of the starch granules are removed by incubating four times with 0.5% SDS (sodium lauryl sulphate) for 10-15 minutes in each case at room temperature under agitation. Each washing step is followed by a centrifugation (5 min, 5.000×g), in order to separate the starch granules from the respective wash buffer.

d) Purification of the Starch that has been Freed of Proteins

The starch obtained from Step c), which has been freed from the proteins bonded to its surface, is subsequently removed by incubating four times with wash buffer for 10-15 minutes in each case at room temperature under agitation. Each washing step is followed by a centrifugation (5 min, 1.000×g), in order to separate the starch granules from the respective wash buffer. These purification steps serve mainly to remove the SDS used in the incubations in Step c).

e) Determination of the Concentration of Isolated Starch

The amount of starch isolated in Step d) is determined photometrically. After suitable dilution, the optical density of the starch suspension is measured against a calibration curve at a wavelength of 600 nm. The linear range of the calibration curve is located between 0 and 0.3 extinction units.

To produce the calibration curves, starch, for example isolated from leaves of an *Arabidopsis thaliana* sex1-3 mutant, is dried under vacuum, weighed and suspended in a defined volume of water. The suspension so obtained is diluted with water in several steps in a ratio of 1 to 1 in each case until a suspension of ca. 5 μg starch per ml of water is obtained. The suspensions obtained by the individual dilution steps are measured in the photometer at a wavelength of 600 nm. The absorption values obtained for each suspension are plotted against the concentration of starch in the respective suspension. The calibration curve obtained should follow a linear mathematical function in the range from 0 μg starch per ml of water to 0.3 μg starch per ml of water.

f) Storage of Isolated Starch

The starch can either be used directly without further storage for further tests, or stored in aliquots in 1.5 mL Eppendorf vessels at −20° C. Both the frozen starch and the non-stored, freshly isolated starch can be used, if required, for the methods described in the present invention relating to in vitro phosphorylation and/or bonding test, for example.

g) Composition of Buffers Used

| 1x starch buffer: | 20 mM | HEPES-KOH, pH 8.0 |
|---|---|---|
|  | 0.2 mM | EDTA |
|  | 0.5% | Triton X-100 |
| Wash buffer: | 50 mM | HEPES/KOH, pH 7.2 |

3. Recombinant Expression of an Identified Starch-Phosphorylating Protein a) Manufacture of a Bacterial Expression Vector Containing a cDNA, which Codes a Starch-Phosphorylating Protein The cDNA coding a starch-phosphorylating protein can be amplified, for example, using mRNA or poly-A-plus-mRNA from plant tissues as a "template", by means of a polymerase chain reaction (PCR). For this purpose, a reverse transcriptase is first used for the manufacture of a cDNA strand, which is complementary to an mRNA, which codes a starch-phosphorylating protein, before the cDNA strand concerned is amplified by means of DNA polymerase. So-called "kits" containing substances, enzymes and instructions for carrying out PCR reactions are available for purchase (e.g. SuperScript™ One-Step RT-PCR System, Invitrogen, Prod. No.: 10928-034). The amplified cDNA coding a starch-phosphorylating protein can subsequently be cloned in a bacterial expression vector, e.g. pDEST™17 (Invitrogen). pDEST™17 contains the T7 promoter, which is used to initiate the transcription of the T7-RNA-polymerase. Furthermore, the expression vector pDEST™17 contains a Shine Dalgarno sequence in the 5'-direction of the T7 promoter followed by a start codon (ATG) and by a so-called His tag. This His tag consists of six codons directly following one another, which each code the amino acid histidine and are located in the reading frame of the said start codon. The cloning of a cDNA coding a starch-phosphorylating protein in pDEST™17 is carried out in such a way that a translational fusion occurs between the codons for the start codon, the His tag and the cDNA coding a starch-phosphorylating protein. As a result of this, following transcription initiated on the T7 promoter, and subsequent translation, a starch-phosphorylating protein is obtained, which contains additional amino acids containing the His tag on its N-terminus.

However, other vectors, which are suitable for expression in micro-organisms, can also be used for the expression of a starch-phosphorylating protein. Expression vectors and associated expression strains are known to the person skilled in the art and are also available for purchase from the appropriate dealer in suitable combinations.

b) Manufacture of Expression Clones in *Escherichia coli*

First of all, an appropriate transformation-competent *E. coli* strain, which chromosomally codes a T7-RNA polymerase, is transformed with the expression plasmid manufactured under Step a), and subsequently incubated overnight at 30° C. on culture medium solidified with agar. Suitable expression strains are, for example, BL21 strains (Invitrogen Prod. No.: C6010-03, which chromosomally code a T7-RNA polymerase under the control of an IPTG-inducible promoter (lacZ).

Bacteria colonies resulting from the transformation can be investigated using methods known to the person skilled in the art to see whether they contain the required expression plasmid containing a cDNA coding the starch-phosphorylating protein. At the same time, expression clones are obtained.

c) Expression of a Starch-Phosphorylating Protein in *Escherichia coli*

First of all, a preliminary culture is produced. To do this, an expression clone obtained in accordance with Step b) is seeded in 30 ml Terrific Broth (TB medium) containing an antibiotic for selection on the presence of the expression plasmid, and incubated overnight at 30° C. under agitation (250 rpm).

A main culture for the expression of a starch-phosphorylating protein is then produced. To do this, in each case, 1 liter Erlenmeyer flasks, each containing 300 ml of TB medium, pre-heated to 30° C., and an antibiotic for selection on the presence of the expression plasmid are each seeded with 10 ml of an appropriate pre-culture and incubated at 30° C. under agitation (250 rpm) until an optical density (measured at a wavelength of 600 nm; $OD_{600}$) of ca. 0.8 is achieved.

If, for the expression of a starch-phosphorylating protein, an expression plasmid is used, in which the expression of the starch-phosphorylating protein is initiated by means of an inducible system (e.g. the expression vector pDEST™17 in BL21 *E. coli* strains, inducible by means of IPTG), then on reaching an $OD_{600}$ of ca. 0.8, the inductor concerned (e.g. IPTG) is added to the main culture. After adding the inductor, the main culture is incubated at 30° C. under agitation (250 rpm) until an $OD_{600}$ of ca. 1.8 is achieved. The main culture is then cooled for 30 minutes on ice before the cells of the main culture are separated from the culture medium by centrifugation (10 minutes at 4.000×g and 4° C.).

4. Purification of a Starch-Phosphorylating Protein a) Breaking Down of Cells Expressing a Starch-Phosphorylating Protein The cells obtained in Step c), Item 3 General Methods are resuspended in lysis buffer. In doing so, ca. 4 ml lysis buffer are added to about 1 g of cells. The resuspended cells are then incubated for 30 minutes on ice before they are broken down with the help of an ultrasonic probe (Baudelin Sonoplus UW 2070, Baudelin electronic, Berlin, settings: Cycle 6, 70%, 1 minute) under continuous cooling by means of the ice. Care must be taken here to ensure that the cell suspension is not heated too much during the ultrasonic treatment. The suspension obtained after the ultrasonic treatment is centrifuged (12 minutes at 20.000×g, 4° C.) and the supernatant obtained after centrifugation is filtered using a filter with a pore size of 45 µm.

b) Purification of the Starch-Phosphorylating Protein

If the starch-phosphorylating protein expressed in *E. coli* cells is a fusion protein with a His tag, then purification can take place with the help of nickel ions, to which the His tag bonds with greater affinity. To do this, 25 ml of the filtrate obtained in Step d) is mixed with 1 ml Ni-agarose slurry (Qiagen, Prod. No.: 30210) and incubated for 1 hour on ice. The mixture of Ni-agarose slurry and filtrate is subsequently spread over a polystyrene column (Pierce, Prod. No.: 29920). The product, which runs through the column, is discarded. The column is next washed by adding 8 ml of lysis buffer, the liquid, which runs through the column, again being discarded. Elution of the starch-phosphorylating protein then takes place by fractionated addition to the column of 1 ml E1 buffer twice, followed by 1 ml E2 buffer once and subsequently 1 ml E3 buffer five times. The product, which runs through the column, which is produced by adding the individual fraction of the appropriate elution buffer (E1, E2, E3 buffer) to the column, is collected in separate fractions. Aliquots of these fractions are subsequently analysed by means of denaturing SDS acrylamide gel electrophoresis followed by Coomassie Blue colouring. The fractions, which contain the starch-phosphorylating protein in sufficient quantity and satisfactory purity, are purified and concentrated with the help of pressurised filtration at 4° C. Pressurised filtration can be carried out, for example, with the help of an Amicon cell (Amicon Ultrafiltration Cell, Model 8010, Prod. No.: 5121) using a Diaflo PM30 membrane (Millipore, Prod. No.: 13212) at 4° C. Other methods known to the person skilled in the art can also be used for concentration however.

c) Composition of Buffers Used

| Lysis buffer: | 50 mM | HEPES |
| --- | --- | --- |
| | 300 mM | NaCl |
| | 10 mM | Imidazol |
| | pH 8.0 (adjust with NaOH) | |
| | 1 mg/ml | Lysozyme (add immediately before using the buffer) |
| | ¼ tablet per 10 ml protease inhibitors completely EDTA free, (Roche product No.: 1873580) (add immediately before using the buffer) | |
| Elution buffer E1: | 50 mM | HEPES |
| | 300 mM | NaCl |
| | 50 mM | Imidazol |
| | pH 8.0 (adjust with NaOH) | |
| Elution buffer E2: | 50 mM | HEPES |
| | 300 mM | NaCl |
| | 75 mM | Imidazol |
| | pH 8.0 (adjust with NaOH) | |
| Elution buffer E3: | 50 mM | HEPES |
| | 300 mM | NaCl |
| | 250 mM | Imidazol |
| | pH 8.0 (adjust with NaOH) | |

5. Recombinant Expression of an R1 Protein

The recombinant expression of an R1 protein is described in the literature (Ritte et al., 2002, PNAS 99, 7166-7171; Mikkelsen et al., 2004, Biochemical Journal 377, 525-532), but can also be carried out in accordance with the methods relating to the recombinant expression of a starch-phosphorylating protein described above under Item 3. General Methods.

6. Purification of an R1 Protein

The purification of an R1 protein is described in the literature (Ritte et al., 2002, PNAS 99, 7166-7171; Mikkelsen et al., Mikkelsen et al., 2004, Biochemical Journal 377, 525-532), but can also be carried out in accordance with the methods relating to the purification of a starch-phosphorylating protein described above under Item 4. General Methods if an R1 fusion protein, which contains a His tag, is produced by expression of R1 in *E. coli* cells.

7. In Vitro Manufacture of Phosphorylated Starch Starting from Non-Phosphorylated Starch a) In Vitro Phosphorylation of Non-Phosphorylated Starch Starch, which does not contain starch phosphate (e.g. isolated from leaves of *Arabidopsis thaliana* sex1-3 mutants with the help of the methods described above under Item 2, General Methods), is mixed with R1 buffer and with purified R1 protein (ca. 0.25 μg R1 protein per mg starch) in order to produce a starch content of 25 mg per ml. This reaction preparation is incubated overnight (ca. 15 h) at room temperature under agitation. R1 bonded to the starch present in the reaction preparation is removed on completion of the reaction by washing four times with ca. 800 μl 0.5% SDS in each case. Subsequently, the SDS still present in the in vitro phosphorylated starch is removed by washing five times with 1 ml wash buffer in each case. All washing steps are carried out at room temperature for 10 to 15 minutes under agitation. Each washing step is followed by a centrifugation (2 min, 10.000× g), in order to separate the starch granules from the respective SDS buffer or wash buffer.

b) Composition of Buffers Used

| R1 buffer: | 50 mM | HEPES/KOH, pH 7.5 |
| --- | --- | --- |
| | 1 mM | EDTA |
| | 6 mM | MgCl$_2$ |
| | 0.5 mM | ATP |
| Wash buffer: | 50 mM | HEPES/KOH, pH 7.2 |

8. Bonding of Proteins to Phosphorylated Starch or Non-Phosphorylated Starch a) Isolation of P-Starch Protein Complexes or Non-Phosphorylated Starch Protein Complexes Ca. 50 mg P-starch or ca. 50 mg non-phosphorylated starch respectively are resuspended in separate preparations in ca. 800 μl protein extract in each case. The protein concentration of the protein extracts should be ca. 4 mg to 5 mg per ml in each case. The incubation of the P-starch or non-phosphorylated starch with protein extracts is carried out at room temperature for 15 minutes at 4° C. under agitation. On completion of the incubation, the reaction preparations are centrifuged using a Percoll cushion (4 ml) (15 minutes, 3500 rpm, 4° C.). After centrifugation, proteins that are not bonded to phosphorylated starch or P-starch will be found in the supernatant and can be removed with a Pasteur pipette. The supernatant is discarded. The sedimented pellet containing P-starch and non-phosphorylated starch, including the proteins bonded to the respective starches (P-starch protein complexes or non-phosphorylated starch protein complexes respectively), obtained after centrifugation is washed twice with 1 ml of wash buffer in each case (see above, General Methods under item 7.b) by incubating for 3 minutes at 4° C. in each case under agitation. The washing step is followed by a centrifugation (5 minutes, 8000 rpm, 4° C. in a table centrifuge, Hettich EBA 12R) in order to separate the P-starch or non-phosphorylated starch respectively from the wash buffer.

b) Dissolving the Proteins Bonded in the P-Starch Protein Complexes or Non-Phosphorylated Starch protein complexes respectively The P-starch protein complexes or non-phosphorylated starch protein complexes respectively obtained in Step a) are resuspended in ca. 150 μl SDS test buffer and incubated at room temperature for 15 minutes under agitation. The P-starch or non-phosphorylated starch respectively is subsequently removed from the dissolved proteins by centrifugation (1 minute, 13,000 rpm, room temperature, Eppendorf table centrifuge). The supernatant obtained after centrifugation is centrifuged again in order to remove any residues of P-starch or non-phosphorylated starch respectively (1 minute, 13,000 rpm, room temperature, Eppendorf table centrifuge) and removed. As a result, dissolved proteins, which bond to the P-starch or non-phosphorylated starch respectively, are obtained.

c) Composition of Buffers Used

| SDS test buffer: | 187.5 mM | Tris/HCl pH 6.8 |
| --- | --- | --- |
| | 6% | SDS |
| | 30% | Glycerine |
| | ~0.015% | Bromophenol blue |
| | 60 mM | Dithioerythritol (DTE, add fresh!) |
| Percoll: | Percoll is dialysed overnight against a solution consisting of 25 mM HEPES/KOH, pH 7.0 | |

9. Separation of Proteins, which Bond to P-Starch and/or Non-Phosphorylated Starch The dissolved proteins obtained in Step c) under Item 8. General Methods relating to the bonding of proteins to P-starch or non-phosphorylated starch respectively are incubated for 5 minutes at 95° C. in each case and subsequently separated with the help of denaturing polyacrylamide gel electrophoresis. In doing so, an equal volume is applied to the acrylamide gel in each case for the dissolved proteins obtained by bonding to P-starch and for those obtained by bonding to non-phosphorylated starch. The gel obtained on completion of electrophoresis is stained at least overnight with colloidal Comassie (Roth, Karlsruhe, Roti-Blue Rod. No.: A152.1) and subsequently de-stained in 30% methanol, 5% acetic acid, or in 25% methanol.

10. Identification and Isolation of Proteins, which Bond to P-Starch and/or Non-Phosphorylated Starch a) Identification of Proteins with Increased Bonding Activity with Respect to P-Starch in Comparison with Non-Phosphorylated Starch Proteins, which, after separation by means of acrylamide gel electrophoresis and subsequent visualisation by staining (see above, Item 9. General Methods), exhibit an increased signal after bonding to P-starch in comparison with a corresponding signal after bonding to non-phosphorylated starch, have increased bonding activity with respect to P-starch in comparison with non-phosphorylated starch. By this means, it is possible to identify proteins, which have increased bonding activity with respect to P-starch in comparison with non-phosphorylated starch. Proteins, which have increased bonding activity with respect to P-starch in comparison with non-phosphorylated starch, are excised from the acrylamide gel.

b) Identification of Proteins, which have Increased Bonding Activity with Respect to P-Starch in Comparison with Non-Phosphorylated Starch Proteins identified in accordance with Step a) are digested with trypsin and the peptides obtained are analysed by means of MALDI-TOF to determine the masses of the peptides obtained. Trypsin is a sequence-specific protease, i.e. trypsin only splits proteins at a specified position when the proteins concerned contain certain amino acid sequences. Trypsin always splits peptide bonds when the amino acids arginine and lysine follow one another starting from the N-terminus. In this way, it is possible to theoretically determine all peptides that would be produced following the trypsin digestion of an amino acid sequence. From the knowledge of the amino acids coding the theoretically determined peptides, the masses of the peptides, which are obtained after theoretical trypsin digestion, can also be determined. Databases (e.g. NCBInr http://prospector.ucsf.edu/ucsfhtml4.0/msfit.htm; Swissprot http://cbrg.inf.ethz.ch/Server/MassSearch.html), which contain information concerning the masses of peptides after theoretical trypsin digestion, can therefore be compared with the real masses of peptides of unknown proteins obtained with MALDI-TOF-MS. Amino acid sequences, which have the same peptide masses after theoretical and/or real trypsin digestion, are to be looked upon as being identical. The databases concerned contain both peptide masses of proteins, the function of which has already been shown, and also peptide masses of proteins, which up to now only exist hypothetically by derivation from amino acid sequences starting from nucleic acid sequences obtained in sequencing projects. The actual existence and the function of such hypothetical proteins has therefore seldom been shown and, if there is a function at all, then this is usually based only on predictions and not on an actual demonstration of the function.

Bands containing proteins obtained in accordance with Step a) are excised from the acrylamide gel; the excised acrylamide piece is reduced and destained by incubating for approximately half an hour at 37° C. in ca. 1 ml 60% 50 mM $NH_4HCO_3$, 40% acetonitrile. The decolourising solution is subsequently removed and the remaining gel dried under vacuum (e.g. Speedvac). After drying, trypsin solution is added to digest the proteins contained in the gel piece concerned. Digestion takes place overnight at 37° C. After digestion, a little acetonitrile is added (until the acrylamide gel is stained white) and the preparation dried under vacuum (e.g. Speedvac). When drying is complete, just enough 5% formic acid is added to cover the dried constituents and incubated for a few minutes at 37° C. The acetonitrile treatment followed by drying is repeated once more. The dried constituents are subsequently absorbed in 0.1% TFA (trifluoroacetic acid, 5 µl to 10 µl) and dripped onto a carrier in ca. 0.5 µl portions. Equal amounts of matrix (ε-cyano-4-hydroxy-cinnamic acid) are also applied to the carrier. After crystallising out the matrix, the masses of peptides are determined by means of MALDI-TOF-MS-MS (e.g. Burker Reflex™ II, Bruker Daltonic, Bremen). With the masses obtained, databases are searched for amino acid sequences, which give the same masses after theoretical trypsin digestion. In this way, amino acid sequences can be identified, which code proteins, which preferably bond to phosphorylated alpha-1,4-glucans and/or which need P-alpha-1,4-glucans as a substrate.

11. Method for Demonstrating Starch-Phosphorylating Activity of a Protein a) Incubation of Proteins with P-Starch and/or Non-Phosphorylated Starch In order to demonstrate whether a protein has starch-phosphorylating activity, proteins to be investigated can be incubated with starch and radioactively labeled ATP. To do this, ca. 5 mg of P-starch or ca. 5 mg of non-phosphorylated starch are incubated with the protein to be investigated (0.01 µg to 5.0 µg per mg of starch used) in 500 µl phosphorylation buffer for 10 minutes to 30 minutes at room temperature under agitation. The reaction is subsequently stopped by the addition of SDS up to a concentration of 2% (weight/volume). The starch granules in the respective reaction mixture are centrifuged (1 minute, 13.000×g), and washed once with 900 µl of a 2% SDS solution and four times each with 900 µl of a 2 mM ATP solution. Each washing step is carried out for 15 minutes at room temperature under agitation. After each washing step, the starch granules are separated from the respective wash buffer by centrifugation (1 min, 13.000×g).

In addition, when carrying out an experiment to demonstrate starch-phosphorylating activity of a protein, further reaction preparations, which do not contain protein or contain inactivated protein, but which are otherwise treated in the same way as the reaction preparations described, should be processed as so-called controls.

b) Determination of the Amount of Phosphate Residues Incorporated in the P-Starch and/or Non-Phosphorylated Starch Due to Enzymatic Activity The starch granules obtained in accordance with Step a) can be investigated for the presence of radioactively labeled phosphate residues. To do this, the respective starch is resuspended in 100 µl of water and mixed with 3 ml of scintillation cocktail in each case (e.g. Ready Safe™, BECKMANN Coulter) and subsequently analysed with the help of a scintillation counter (e.g. LS 6500 Multi-Purpose Scintillation Counter, BECKMANN COULTER™).

c) Identification of Proteins, which Preferably Use P-Starch as a Substrate

If a protein is incubated in separate preparations, once with P-starch and once with non-phosphorylated starch, in accordance with the method described under a), then, by comparing the values for the presence of starch phosphate obtained according to Step b), it can be determined whether the protein concerned has incorporated more phosphate in P-starch in comparison with non-phosphorylated starch. In this way, proteins can also be identified, which can introduce phosphate into P-starch but not into non-phosphorylated starch. That is to say, proteins can be identified, which require already phosphorylated starch as a substrate for a further phosphorylating reaction.

d) Composition of Buffers Used

| Phosphorylation buffer: | 50 mM | HEPES/KOH, pH 7.5 |
|---|---|---|
|  | 1 mM | EDTA |
|  | 6 mM | MgCl$_2$ |
|  | 0.01 to 0.5 mM | ATP |

0.2 to 2 µCi per ml randomised $^{33}$P-ATP (alternatively, ATP, which contains a phosphate residue, which is specifically labeled in the beta position, can also be used)

In conjunction with the present invention, the term "randomised ATP" is to be understood to mean ATP, which contains labeled phosphate residues both in the gamma position and in the beta position (Ritte et al. 2002, PNAS 99, 7166-7171). Randomised ATP is also described in the scientific literature as beta/gamma ATP. A method for manufacturing randomised ATP is described in the following.

i) Manufacture of Randomised ATP

The method described here for manufacturing randomised ATP with the help of enzyme catalysed reactions is based on the following reaction mechanisms:

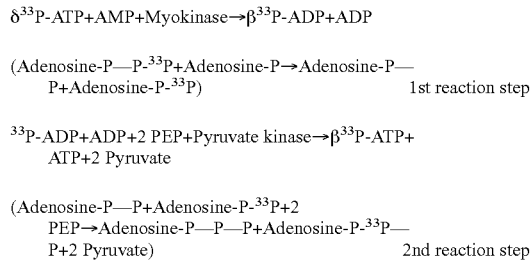

The reaction equilibria lie on the product side but, in spite of this, this reaction produces a mixture consisting mainly of β$^{33}$P-ATP and some γ$^{33}$P-ATP.

ii) Carrying Out The 1st Reaction Step

ATP (100 µCi, 3000 Ci per mmol), which contains a phosphate residue labeled with $^{33}$P in the gamma position (Hartmann Analytic, 10 µCi/µl), is incubated with 2 µl myokinase (AMP-phosphotransferase, from rabbit muscle; SIGMA, Prod. No.: M3003 3.8 mg/ml, 1,626 units/mg) in 90 µl randomising buffer for 1 hour at 37° C. The reaction is subsequently stopped by incubating for 12 minutes at 95° C. before the reaction preparation is purified up by means of centrifugal filtration using a Microcon YM 10 filter (Amicon, Millipore Prod. No. 42407) at 14.000×g for at least 10 minutes.

iii) Carrying Out The 2nd Reaction Step

2 µl pyruvate kinase (see below for how to manufacture an appropriate solution) and 3 µl 50 mM PEP (phosphoenolpyruvate) are added to the filtrate obtained in Step 11). This reaction mixture is incubated for 45 minutes at 30° C. before the reaction is stopped by incubating at 95° C. for 12 minutes. The reaction mixture is subsequently centrifuged (2 minutes, 12,000 rpm in an Eppendorf table centrifuge). The supernatant containing randomised ATP obtained after centrifugation is removed, aliquoted and can be stored at −20° C.

Manufacture of the Pyruvate Kinase Solution

15 µl pyruvate kinase (from rabbit muscle, Roche, Prod. No. 12815), 10 mg/ml, 200 units/mg at 25° C.) are centrifuged, the supernatant discarded and the pellet absorbed in 27 µl pyruvate kinase buffer.

iv) Buffers Used

| Pyruvate kinase buffer: | 50 mM | HEPES/KOH pH 7.5 |
|---|---|---|
|  | 1 mM | EDTA |
| Randomising buffer: | 100 mM | HEPES/KOH pH 7.5 |
|  | 1 mM | EDTA |
|  | 10% | Glycerol |
|  | 5 mM | MgCl$_2$ |
|  | 5 mM | KCl |
|  | 0.1 mM | ATP |
|  | 0.3 mM | AMP |

12. Demonstration of the Autophosphorylation of a Protein

In order to demonstrate whether a protein has auto-phosphorylating activity, proteins to be investigated can be incubated with radioactively labeled ATP. To do this, proteins to be investigated (50 µg to 100 µg) are incubated in 220 µl phosphorylation buffer (see above, Item 12 d), General Methods) for 30 minutes to 90 minutes at room temperature under agitation. The reaction is subsequently stopped by the addition of EDTA up to a final concentration of 0.11 M. Ca. 2 µg to 4 µg of protein are separated with the help of denaturing polyacrylamide gel electrophoresis (7.5% acrylamide gel). The gel obtained after polyacrylamide gel electrophoresis is subjected to autoradiography. Proteins, which exhibit a signal in the autoradiography, carry a radioactive phosphate residue.

13. Identification of the C-Atom Positions of the Glucose Molecules of an Alpha-1,4-Glucan, into which Phosphate Residues are Introduced by a Starch-Phosphorylating Protein Which C-atom positions of the glucose molecules of an alpha-1,4-glucan are phosphorylated by a protein can be demonstrated in a controlled manner by hydrolysis of the phosphorylated glucans obtained by means of an appropriate protein in vitro, subsequent separation of the glucose monomers obtained after hydrolysis, followed by measurement of the phosphate incorporated by an appropriate protein in certain fractions of the glucose molecules.

a) Total Hydrolysis of the Alpha-1,4-Glucans

Water suspensions containing alpha-1,4-glucan are centrifuged, the sedimented pellet subsequently resuspended in 0.7 M HCl (Baker, for analysis) and incubated for 2 hours at 95° C. under agitation. On completion of incubation, the samples are briefly cooled and centrifuged (e.g. 2 minutes 10.000×g). The supernatant obtained is transferred to a new reaction vessel and neutralised by the addition of 2 M NaOH (Baker, for analysis). If a pellet remains, it is resuspended in 100 µl of water and the quantity of labeled phosphate present therein is determined as a control.

The neutralised supernatant is subsequently centrifuged over a 10 kDa filter. By measuring an aliquot of the filtrate obtained, the quantity of labeled phosphate in the filtrate is determined with the help of a scintillation counter, for example.

b) Fractionation of the Hydrolysis Products and Determination of the Phosphorylated C-Atom Positions The neutralised filtrates of the hydrolysis products obtained by means of Step a) can be separated (when using radioactively labeled ATP about 3000 cpm) with the help of high-pressure anion exchange chromatography (HPAE), for example. The neutralised filtrate can be diluted with H$_2$O to obtain the volume required for HPAE. In addition, glucose-6-phosphate (ca. 0.15 mM) and glucose-3-phosphate (ca. 0.3 mM) are added to the appropriate filtrates in each case as an internal control. Separation by means of HPAE can be carried out, for example, with the help of a Dionex DX 600 Bio Lc system using a CarboPac PA 100 column (with appropriate pre-column) and a pulsed amperometric detector (ED 50). In doing so, before injecting the sample, the column is first rinsed for 10 minutes with 99% eluent C and 1% eluent D. A sample volume of 60 μl is then injected. The elution of the sample takes place under the following conditions:
Flow rate: 1 ml per minute
Gradient: linearly increasing from 0 minutes to 30 minutes

|  | Eluent C | Eluent D |
|---|---|---|
| 0 minutes | 99% | 1% |
| 30 minutes | 0% | 100% |
| 35 minutes | 0% | 100% |
| Run terminated | | |

The hydrolysis products eluted from the column are collected in individual fractions of 1 ml each. As, in each case, non-labeled glucose-3-phosphate (Ritte et al. 2002, PNAS 99, 7166-7171) and non-labeled glucose-6-phosphate (Sigma, Prod. No.: G7879) have been added to the injected samples of hydrolysis products as internal standards, the fractions, which contain either glucose-3-phosphate or glucose-6-phosphate, can be determined by means of pulsed amperometric detection. By measuring the amount of labeled phosphates in the individual fractions and subsequently comparing with the fractions, which contain glucose-3-phosphate or glucose-6-phosphate, this can be used to determine those fractions, in which labeled glucose-6-phosphate or labeled glucose-3-phosphate is contained. The amount of labeled phosphate in the fraction concerned is determined. From the ratios of the amounts of glucose-3-phosphate to glucose-6-phosphate measured for labeled phosphate in the individual hydrolysis products, it can now be determined which C-atom position is preferably phosphorylated by an alpha-1,4-glucan phosphorylating enzyme.

c) Buffers Used

| Eluent C: | 100 mM | NaOH |
|---|---|---|
| Eluent D: | 100 mM | NaOH |
|  | 500 mM | sodium acetate |

14. Transformation of Rice Plants

Rice plants were transformed in accordance with the methods described by Hiei et al. (1994, Plant Journal 6(2), 271-282).

15. Transformation of Potato Plants

Potato plants were transformed with the help of *agrobacterium* as described by Rocha-Sosa et al. (EMBO J. 8, (1989), 23-29).

16. Determination of the Starch Content of Leaf Material a) Sample Preparation:

Removal of Soluble Sugar by Ethanolic Extraction:

Ca. 1 g of fresh leaf material from plants is freeze-dried, weighed and subsequently homogenised to a fine powder with a ball mill. Ca. 50 mg of pulverised leaf material (double determination) are weighed, mixed with 1 ml 80% ethanol, strongly agitated and the homogenous dispersion incubated for 1 hour at 80° C. in the water bath. After cooling to ca. 40° C., the dispersion is centrifuged for 5 minutes at 3000 rpm (Minifuge RF, Heraeus). The supernatant is discarded. The leaf material is mixed two more times with 1 ml 80% ethanol in each case and in each case incubated for 20 minutes at 80° C. in the water bath. After cooling and centrifugation (see above) the supernatants are discarded in each case.

(b) Determination of the Starch in the Microtiter Plate/Spectramax at 340 nm

Determination is carried out with the help of the UV tester for analysing the amount of starch in foodstuffs, Boehringer Mannheim, Order No.: 207748 (amyloglucosidase, starch measuring buffer, glucose-6-phosphate dehydrogenase).

The sugar-free leaf material is mixed with 400 μl 0.2 N KOH and homogenised by strong agitation. The homogenate is incubated in the water bath for 1 hour at 95° C. After cooling, 75 μl 1M acetic acid are added and thoroughly mixed. Centrifugation is then carried out for 10 minutes at 4000 rpm. 25 or 50 μl of supernatant are added to 50 μl amyloglucosidase (Boehringer Mannheim) and 25 or 50 μl respectively of Millipore water, in a microtiter plate, and digested for 1 hour at 56° C. 196 μl starch measuring buffer (Boehringer Mannheim) is prepared in a further microtiter plate. 4 (to 20) μl of the cooled starch digest is added to this from a pipette. Depending on the glucose concentration, the ratio can be increased to 40 μl digest+160 μl starch measuring buffer.

Measurement: Agitate, pre-read

+2 μl glucose-6-phosphate dehydrogenase (Boehringer Mannheim)

Incubation: 30 minutes at 37° C., measure (c) The Starch Content is Calculated as Specified Below:

Measured volume (200 μl)×Extraction volume (4750 μl)×amyloglucosidase digest volume (200 μl)× ΔOD/ε×1000×Sample measured volume (4 μl ... 40 μl)×Sample digest volume (50 μl)×Initial weight (g)×d(1)=Concentration (μmol/g dry weight)

ε=6.3 l×mmol−1×cm−1 (molar extinction coefficient of NADH at 340 nm)

From the weights determined before and after freeze-drying and the molar masses of glucose (162.1 g/mol-anhydride), the concentration is calculated in mg glucose/g of fresh weight.

17. Staining of Plant Parts with Lugol's Solution

Plant parts to be investigated are removed from the plants and incubated in 80% ethanol at 50° C. until the plant parts contain no more green colouring. The plant parts are then incubated in Lugol's solution before excess Lugol's solution is rinsed from the plant parts with water. Plant parts, which contain starch, have a brownish to black coloration. The stronger the coloration, the more starch is contained by the plant parts concerned.

EXAMPLES

1. Isolation of a Protein from *Arabidopsis thaliana*, which has Increased Bonding Activity with Respect to P-Starch in Comparison with Non-Phosphorylated Starch a) Manufacture of Protein Extracts from *Arabidopsis thaliana*

Protein extracts were manufactured from approximately 7 g of leaves (fresh weight) of *Arabidopsis thaliana* (Ecotype Columbia, Col-O) in accordance with the method described under Item 1, General Methods.

b) Isolation of Starch Granules from Leaves of Sex1-3 Mutant of *Arabidopsis thaliana*

Starch granules were isolated from approximately 20 g (fresh weight) of leaves of a sex1-3 mutants of *Arabidopsis thaliana* in accordance with the method described under Item 2, General Methods.

c) In Vitro Phosphorylation of Starch Isolated from a Sex1-3 Mutant of *Arabidopsis thaliana* with Purified R1 Protein.

About 30 mg of non-phosphorylated starch isolated from a sex1-3 mutant of *Arabidopsis thaliana* was phosphorylated in accordance with the method described under Item 7, General Methods, by means of an R1 protein recombinantly expressed in *E. coli* and purified. The method described by Ritte et al. (2002, PNAS 99, 7166-7171) was used for expressing the R1 protein in *E. coli* and for subsequent purification.

d) Isolation of Proteins, which Bond to P-Starch and/or Non-Phosphorylated Starch Protein extracts of *Arabidopsis thaliana*, obtained in accordance with Step a), were incubated and washed in a Preparation A with 50 mg of the in vitro phosphorylated starch manufactured in accordance with Step c) using the method described under Item 8 a), General Methods.

In a second Preparation B, protein extracts of *Arabidopsis thaliana*, obtained in accordance with Step a), were incubated and washed with 50 mg of the non-phosphorylated starch manufactured in accordance with Step b) using the method described under Item 8 a), General Methods.

Subsequently, proteins bound to the P-starch of Preparation A and to the non-phosphorylated starch of Preparation B were dissolved in accordance with the method described under Item 8 b), General Methods.

In a third Preparation C, 50 mg of the in vitro phosphorylated starch manufactured in accordance with Step c) were incubated and washed using the method described under Item 8 a), General Methods. Preparation C contained no protein extracts however.

e) Separation of the Proteins Obtained in Accordance with Step D) by Means of Acrylamide Gel Electrophoresis The proteins of Preparations A, B and C obtained in Step d) were separated by means of a 9% acrylamide gel under denaturing conditions (SDS) using the method described under Item 9, General Methods, and subsequently strained with Coomassie Blue. The stained gel is shown in FIG. 1. It can be clearly seen that a protein, which has a molecular weight of ca. 130 kDa in denaturing acrylamide gel referred to a protein standard marker (Trace M), preferably bonds to phosphorylated starch (Trace P) in comparison with non-phosphorylated starch (K).

f) Identification of the Protein, which Preferably Bonds to P-Starch in Comparison with Non-Phosphorylated Starch The band of the protein with a molecular weight of ca. 130 kDa identified in Step e) was excised from the gel. The protein was subsequently released from the acrylamide as described under General Methods 10 b), digested with trypsin and the peptide masses obtained determined by means of MALDI-TOF-MS. The so-called "fingerprint" obtained by MALDI-TOF-MS was compared with fingerprints of theoretically digested amino acid molecules in databases (Mascot: http://vvww.matrixscience.com/search_form_select.html; ProFound: http://129.85.19.192/profound_bin/WebProFound.exe; PepSea: http://195.41.108.38/PepSeaIntro.html). As such a fingerprint is very specific to a protein, it was possible to identify an amino acid molecule. With the help of the sequence of this amino acid molecule, it was possible to isolate a nucleic acid sequence from *Arabidopsis thaliana* coding an OK1 protein. The protein identified with this method was designated A.t.-OK1. Analysis of the amino acid sequence of the OK1 protein from *Arabidopsis thaliana* showed that this deviated from the sequence that was present in the database (NP 198009, NCBI). The amino acid sequence shown in SEQ ID No 2 codes the A.t.-OK1 protein. SEQ ID No 2 contains deviations when compared with the sequence in the database (Acc.: NP 198009.1, NCBI). The amino acids 519 to 523 (WRLCE) and 762 to 766 (VRARQ) contained in SEQ ID No 2 are not in the sequence, which is present in the database (ACC.: NP 198009.1). Compared with Version 2 of the database sequence (Acc.: NP 198009.2), the amino acid sequence shown in SEQ ID NO 2 also contains the additional amino acids 519 to 523 (WRLCE).

2. Cloning of a cDNA, which Codes the Identified OK1 Protein

The A.t.-OK1 cDNA was isolated with the help of reverse PCR using mRNA isolated from leaves of *Arabidopsis thaliana*. To do this, a cDNA Strand was synthesised by means of reverse transcriptase (SuperScript™ First-Strand Synthesis System for RT PCR, Invitrogen Prod. No.: 11904-018), which was then amplified using DNA polymerase (Expand High Fidelity PCR Systems, Roche Prod. No.: 1732641). The amplified product obtained from this PCR reaction was cloned in the vector pGEM®-T (Invitrogen Prod. No.: A3600). The plasmid obtained is designated A.t.-OK1-pGEM, the cDNA sequence coding the A.t.-OK1 protein was determined and is shown under SEQ ID NO. 1.

The sequence shown under SEQ ID NO 1 is not the same as the sequence, which is contained in the database. This has already been discussed for the amino acid sequence coding an A.t.-OK1 protein.

Conditions used for the amplification of the cDNA coding the A.t.-OK1 protein

First Strand Synthesis:

The conditions and buffer specified by the manufacturer were used. In addition, the reaction preparation for the first strand synthesis contained the following substances:

```
3 µg       total RNA

5 µM       3'-Primer (OK1rev1:
           5'-GACTCAACCACATAACACACAAAGATC)

0.83 µM    dNTP mix
```

The reaction preparation was incubated for 5 minutes at 75° C. and subsequently cooled to room temperature.

The 1$^{st}$ strand buffer, RNase inhibitor and DTT were then added and incubated for 2 minutes at 42° C. before 1 µL Superscript RT DNA polymerase was added and the reaction preparation incubated for 50 minutes at 42° C.

Conditions for the amplification of the first strand by means of PCR:

```
1 µL       of the reaction preparation of the
           first strand synthesis 0.25 µM    3'Primer (OK1rev2:
           5'- TGGTAACGAGGCAAATGCAGA)

0.25 µM    5'Primer (OK1fwd2:
           5'- ATCTCTTATCACACCACCTCCAATG)
```

Reaction Conditions:

| Step 1 | 95° C. 2 min |
| --- | --- |
| Step 2 | 94° C. 20 sec |
| Step 3 | 62° C. 30 sec |
| Step 4 | 68° C. 4 minutes |
| Step 5 | 94° C. 20 sec |
| Step 6 | 56° C. 30 sec |
| Step 7 | 68° C. 4 minutes |
| Step 8 | 68° C. 10 minutes |

The reaction was first carried out in accordance with Steps 1 to 4. 10 repeats (cycles) were carried out between Step 4 and Step 2, the temperature of Step 3 being reduced by 0.67° C. after each cycle. This was subsequently followed by the reaction in accordance with the conditions specified in Steps 5 to 8. 25 repeats (cycles) were carried out between Step 7 and Step 5, the time of Step 7 being increased by 5 sec on each cycle. On completion of the reaction, the reaction was cooled to 4° C.

3. Manufacture of a Vector for the Recombinant Expression of cDNA of the OK1 Protein Following amplification by means of PCR by using the plasmid A.t.-OK1-pGEM as a template using Gateway Technology (Invitrogen), the sequence coding the OK1 protein from *Arabidopsis thaliana* was next cloned in the vector pDONOR™ 201 (Invitrogen Prod. No.: 11798-014). Subsequently, the coding region of the OK1 protein from the vector obtained was cloned by sequence-specific recombination in the expression vector pDEST17™ (Invitrogen Prod. No.: 11803-014). The expression vector obtained was designated as A.t.-OK1-pDEST™17. The cloning resulted in a translational fusion of the cDNA coding the A.t-OK1 protein with the nucleotides present in the expression vector pDEST™17. The nucleotides originating from the vector pDEST™17, which are translationally fused with the cDNA coding the A.t.-OK1 protein, code 21 amino acids. These 21 amino acids include, amongst others, the start codon (ATG) and a so-called His tag (6 histidine residues directly after one another). After translation of these translationally fused sequences, this results in an A.t.-OK1 protein, which has the additional 21 amino acids coded by nucleotides originating from the vector at its N-terminus. The recombinant A.t.-OK1 protein resulting from this vector therefore contains 21 additional amino acids originating from the vector pDEST™17 at its N-terminus.

4. Heterological Expression of the OK1 Protein in *E. coli*

The expression vector A.t.-OK1-pDEST™17 obtained in accordance with Example 3 was transformed in the *E. coli* strain BL21 Star™ (DE3) (Invitrogen, Prod. No. C6010-03). A description of this expression system has already been given above (see Item 3, General Methods). Bacteria clones, containing the vector A.t.-OK1-pDEST™17, resulting from the transformation were next used to manufacture a preliminary culture, which was subsequently used for inoculating a main culture (see Item 3.c, General methods). The preliminary culture and the main culture where each incubated at 30° C. under agitation (250 rpm). When the main culture had reached an $OD_{600}$ of ca. 0.8, the expression of the recombinant A.t.-OK1 protein was induced by the addition of IPTG (isopropyl-beta-D-thiogalactopyranoside) until a final concentration of 1 mM was achieved. After the addition of IPTG, the main culture was incubated at 30° C. under agitation (250 rpm) until an $OD_{600}$ of ca. 1.8 was achieved. The main culture was then cooled for 30 minutes on ice before the cells of the main culture were separated from the culture medium by centrifugation (10 minutes at 4.000×g and 4° C.).

5. Purification of the Recombinantly Expressed OK1 Protein

The purification and concentration of the A.t.-OK1 protein from cells obtained in accordance with Example 4 was carried out using the method described under Item 4, General Methods.

6. Demonstration of Starch-Phosphorylating Activity of the OK1 Protein

The starch-phosphorylating activity of the A.t.-OK1 protein was demonstrated in accordance with the method described under Item 11, General Methods. In doing so, 5 µg of purified A.t.-OK1 Protein manufactured in accordance with Example 5 was in each case incubated in a Preparation A with 5 mg of starch isolated from a sex1-3 mutant of *Arabidopsis thaliana* in accordance with Example 1b) and in a Preparation B with 5 mg of starch obtained by enzymatic phosphorylation of starch isolated from a sex1-3 mutant of *Arabidopsis thaliana* in accordance with Example 1c), in each case in 500 µl of phosphorylation buffer containing 0.05 mM radioactively ($^{33}$P) labeled, randomised ATP (in total 1,130,00 cpm, ca. 0.55 µCi) for 30 minutes at room temperature under agitation. A Preparation C was used as a control, which was the same as Preparation B, except that it contained no OK1 protein, but was otherwise treated in the same way as Preparations A and B. Two tests, which were independent from one another, were carried out for all preparations (A, B, C).

Figure 3:
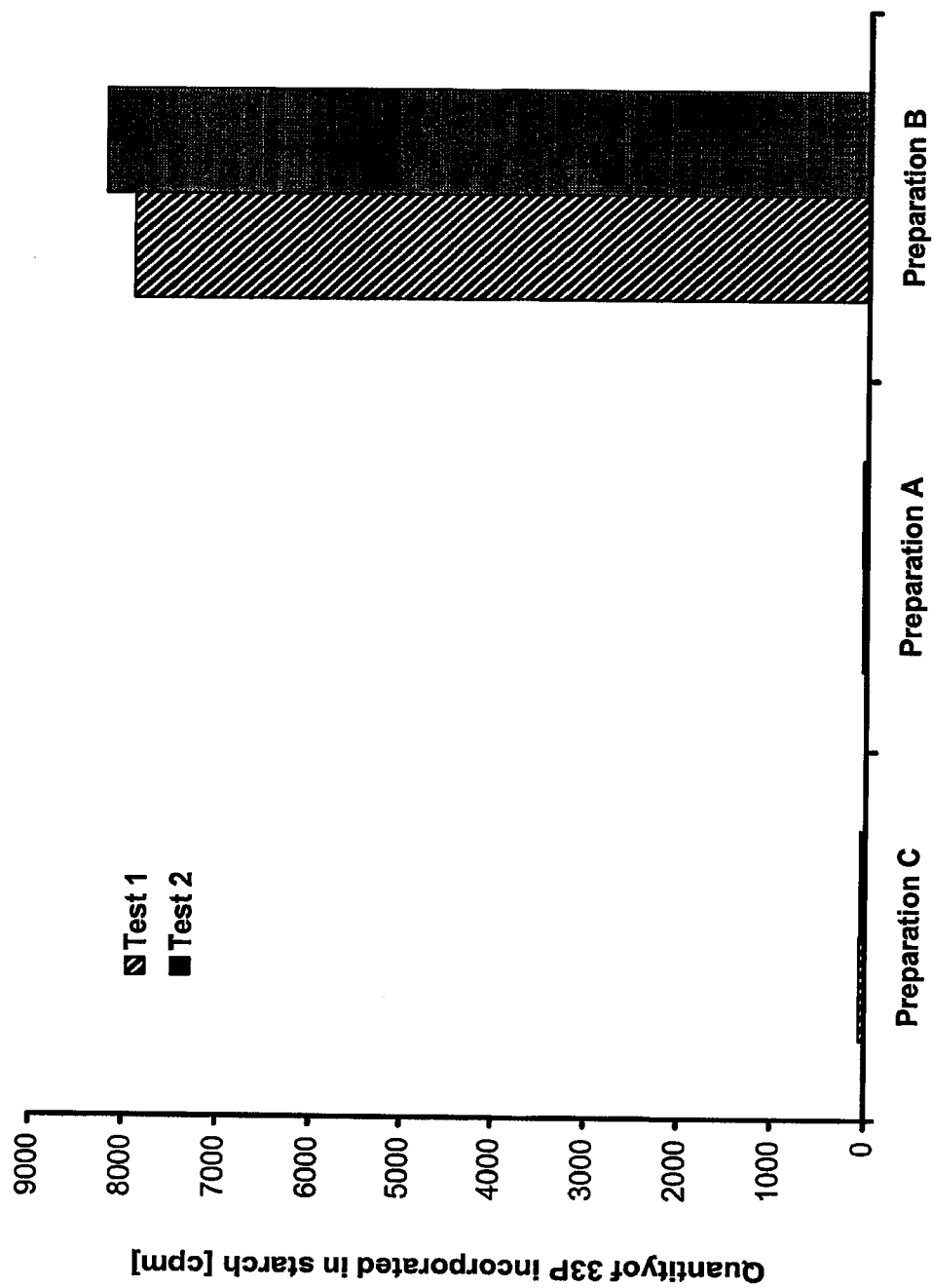
FIG. 3: Demonstration of the starch-phosphorylating activity of an OK1 protein (see Example 6). OK1 protein was incubated with non-phosphorylated starch isolated from leaves of an *Arabidopsis thaliana* sex1-3 mutant (Preparation A) and starch isolated from leaves of an *Arabidopsis thaliana* sex1-3 mutant, which was phosphorylated retrospectively in sex1-3 mutant, which was phosphorylated retrospectively in vitro with an R1 protein (Preparation B). Preparation C is the Same as Preparation B, Except that this Preparation C was incubated without OK1 protein. Two independent tests were carried out for each preparation (A, B, C) (Test 1 and Test 2). The respective amounts are shown, measured in cpm (counts per minute), on $^{33}$P labeled phosphate, which was introduced into non-phosphorylated starch (Preparation A) and phosphorylated starch (Preparation B).
Figure 4:
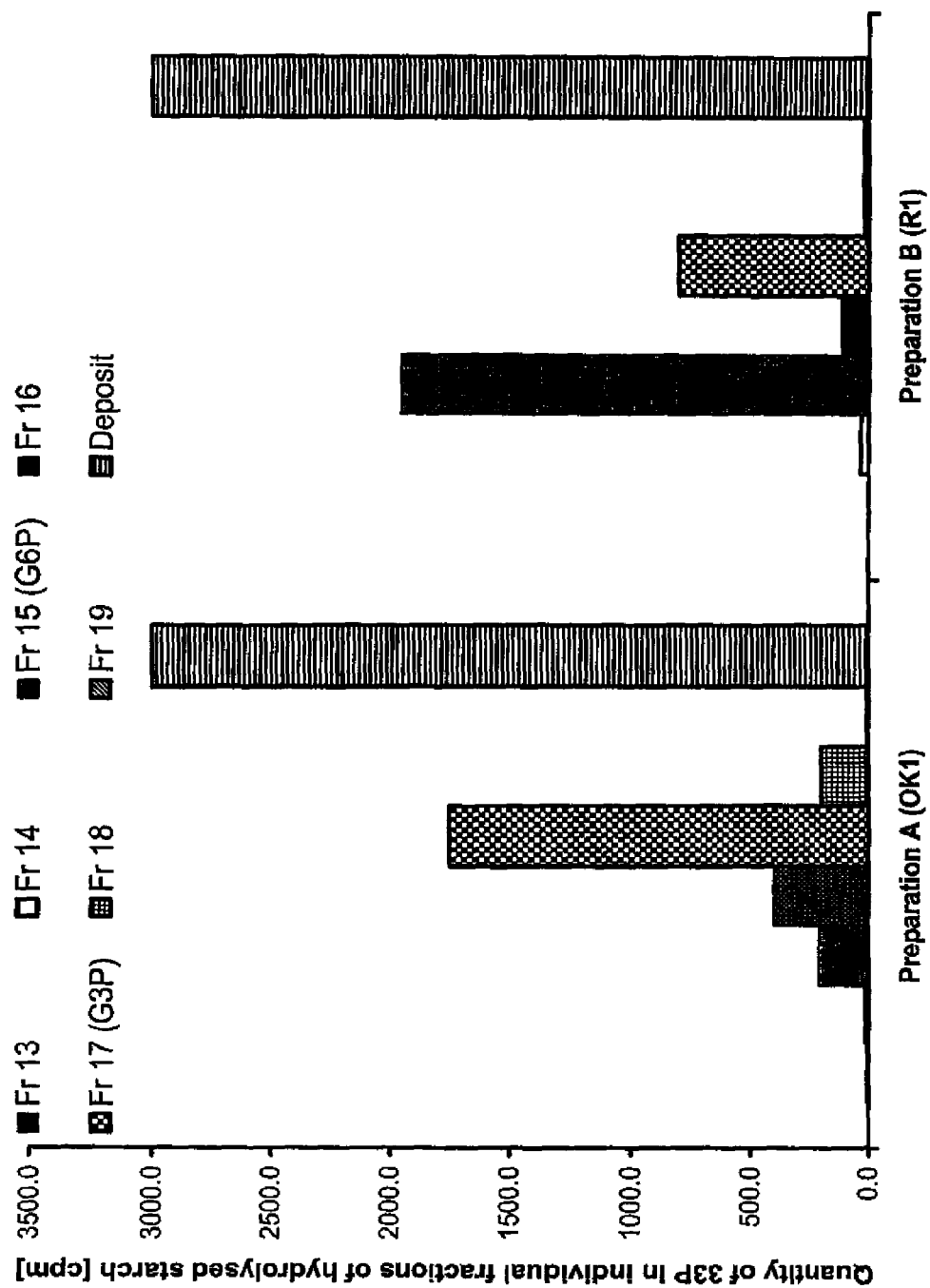
FIG. 4: Comparison of the C-atom positions of glucose molecules of the starch, which was phosphorylated from an R1 protein and an OK1 protein respectively (see Example 9). OK1 protein (Preparation A) was incubated in the presence of ATP labeled with $^{33}$P with starch isolated from leaves of an *Arabidopsis thaliana* sex1-3 mutant, which was phosphorylated retrospectively in vitro with an R1 protein. R1 protein (Preparation B) was incubated in the presence of ATP labeled with $^{33}$P with starch isolated from leaves of an *Arabidopsis thaliana* sex1-3 mutant. On completion of incubation, a total hydrolysis of the starch was carried out and the hydrolysis products were separated by means of HPAE chromatography. As standard, glucose-6-phosphate and glucose-3-phosphate were added to the hydrolysis products before separation. The hydrolysis products separated by means of HPAE chromatography were collected in individual fractions. The added glucose-6-phosphate eluted with fraction 15 and the added glucose-3-phosphate with fraction 17. The fractions obtained were subsequently investigated for the presence of radioactively labeled phosphate. The amount of $^{33}$P labeled phosphate which was introduced into the hydrolysis products of the phosphorylated starch by the OK1 protein or the R1 protein measured in the individual fractions, measured in cpm (counts per minute), is shown graphically.

Using a scintillation counter, the starches from Preparations A, B, and C were investigated for the presence of radioactively labeled phosphate (see Item 11 b), General Methods). The results are shown in Table 1 and in FIG. 3.

TABLE 1

Demonstration of starch-phosphorylating activity of the OK1 protein

| | Measured radioactivity [cpm] | |
| --- | --- | --- |
| | Test 1 | Test 2 |
| Preparation A (non-phosphorylated starch + OK1) | 42 | 47 |
| Preparation B (phosphorylated starch + OK1) | 7921 | 8226 |
| Preparation C (phosphorylated starch without protein) | 56 | 53 |

From the results obtained, it can be seen that the OK1 protein does not transfer phosphate groups from ATP to starch when non-phosphorylated starch is provided as a substrate, as the quota of phosphate groups transferred to non-phosphorylated starch by means of an OK1 protein, measured in cpm, does not exceed the quota of radioactively labeled phosphate groups in Preparation C (control). If, on the other hand, P-starch is provided as a substrate, the quota of radioactive phosphate groups, measured in cpm, which are transferred from ATP to P-starch, is significantly higher. From this, it can be seen that the OK1 protein requires P-starch as a substrate and that non-phosphorylated starch is not accepted as a substrate by the OK1 protein.

Figure 6:
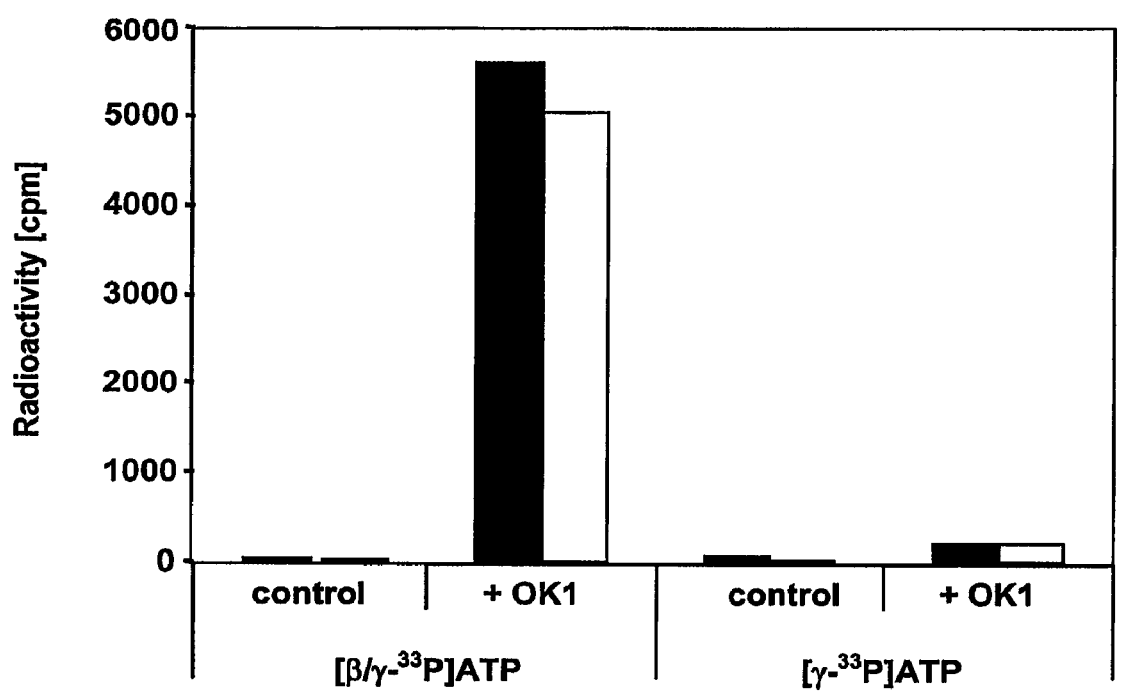
FIG. 6: Demonstration of the transfer of the beta-phosphate residue of ATP to starch in a reaction catalysed by an OK1 protein. Either ATP specifically labeled with $^{33}$P in the gamma position or randomised $^{33}$P ATP was used to phosphorylate starch, which had been isolated from leaves of an *Arabidopsis thaliana* sex1-3 mutant and phosphorylated in vitro by means of an R1 protein and, by means of an OK1 protein. No OK1 protein was added in any of the experiments designated as "control". Each preparation was tested twice, independently from one another. The results of both tests are shown.

If the test described above is carried out with ATP specifically labeled in the gamma position with $^{33}$P, then it is not possible to establish an incorporation of radioactively labeled phosphate in the starch. From this, it can be seen that the beta phosphate residue of ATP is transferred from an OK1 protein to starch. The results of such a test are shown in FIG. 6.

7. Demonstration of Autophosphorylation

Autophosphorylation of the A.t.-OK1 protein was demonstrated by means of the methods described above (see Item 12, General Methods). Here, 50 µg of purified A.t.-OK1 protein were incubated with radioactively labeled, randomised ATP in 220 µl of phosphorylation buffer (see above, Item 12 d), General Methods) at room temperature for 60 minutes under agitation. Subsequently, 100 µl in each case were removed from the incubation preparations and transferred to four fresh reaction vessels. In reaction vessel 1, the reaction was stopped by the addition of 40 µl 0.11 M EDTA. Reaction vessel 2 was incubated at 95° C. for 5 minutes. HCl was added to reaction vessel 3 up to a final concentration of 0.5 M, and NaOH was added to reaction vessel 4 up to a final concentration of 0.5 M. Reaction vessels 3 and 4 were each incubated for 25 minutes at 30° C. Subsequently, 50 µl in each case were removed from reaction vessels 1, 2, 3 and 4, mixed with SDS test buffer and separated by means of SDS acrylamide gel electrophoresis (7.5% acrylamide gel). For this purpose, samples from the reaction vessels were applied to each of two identical acrylamide gels. One of the gels obtained on completion of electrophoresis was subjected to autoradiography, while the second gel was stained with Coomassie Blue.

Figure 2:
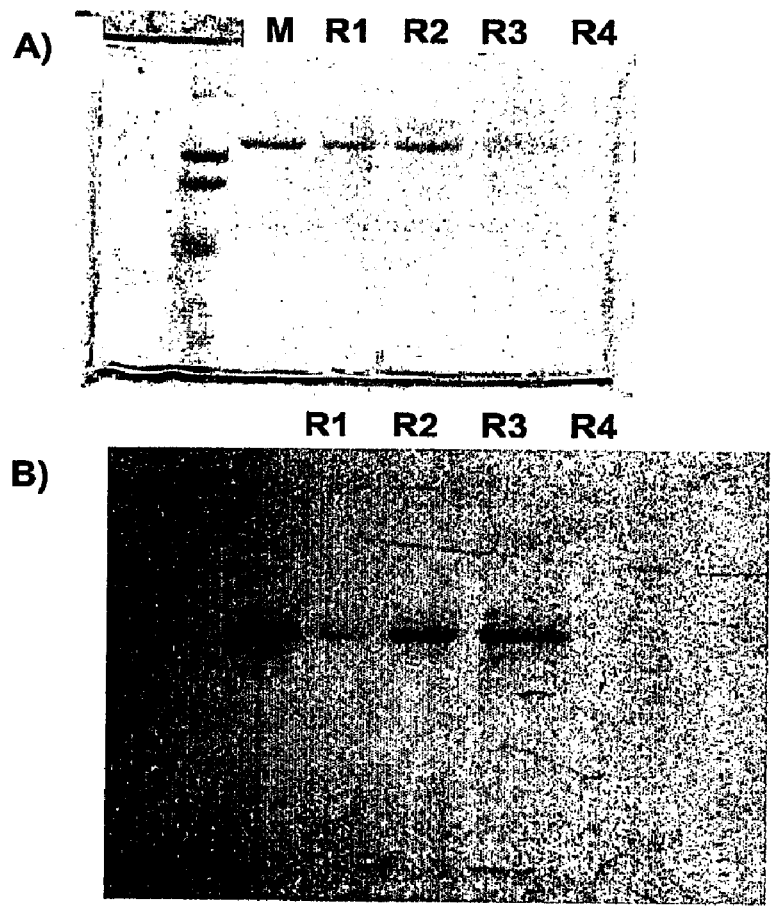
FIG. 2: Demonstration of the autophosphorylation of the OK1 protein.

In the gel stained with Coomassie Blue (see FIG. 2A)), it can be clearly seen that treatment with 0.5 M NaOH leads to a degradation of OK1 protein. The OK1 protein must therefore be described as unstable compared with NaOH. Incubations at 30° C., 95° C. and with 0.5 M HCl show that the OK1 protein is relatively stable under the stated incubation conditions. This can be concluded from the fact that, under these incubation conditions, in each case approximately the same amounts of OK1 protein can be demonstrated in the gel after staining with Coomassie Blue.

In the autoradiography (see FIG. 2B)), it can be seen by comparison with the phosphorylated OK1 protein incubated at 30° C. that an incubation of the phosphorylated OK1 protein at 95° C. leads to a significant reduction in the phosphate, which has bonded to the OK1 protein. The bond between the phosphate residue and an amino acid of the OK1 protein must therefore be described as heat-unstable. Furthermore, a slight reduction of the phosphate bonded to the OK1 protein can also be seen for the incubation with 0.5 M HCl and 0.5 M NaOH in comparison with phosphorylated OK1 protein incubated at 30° C. If the fact is taken into account that the quantity of OK1 protein in the autoradiography after treatment with 0.5 M NaOH is significantly less than in the samples treated with heat and acid on account of the instability of the OK1 protein compared with NaOH, then it can be concluded that the bond between the phosphate residue and an amino acid of the OK1 protein will be relatively stable with respect to bases. As the sample treated with acid contains approximately the same amounts of protein as the sample incubated at 30° C. and at 95° C., and yet has a significantly lower signal in the autoradiography than the sample treated at 30° C., it must be assumed that acid incubation conditions also split the bond between a phosphate residue and an amino acid of the OK1 protein to a certain extent. An instability in the bond between a phosphate residue and an amino acid of the OK1 protein could therefore also be established in the tests carried out. At the same time, the instability with respect to acids is significantly less marked than the instability with respect to heat.

Bonds between the amino acids histidine and phosphate are heat-unstable, acid-unstable but base-stable (Rosenberg, 1996, Protein Analysis and Purification, Birkhäuser, Boston, 242-244). The results described above are therefore an indication that a phosphohistidine is produced by the autophosphorylation of an OK1 protein.

Figure 5:
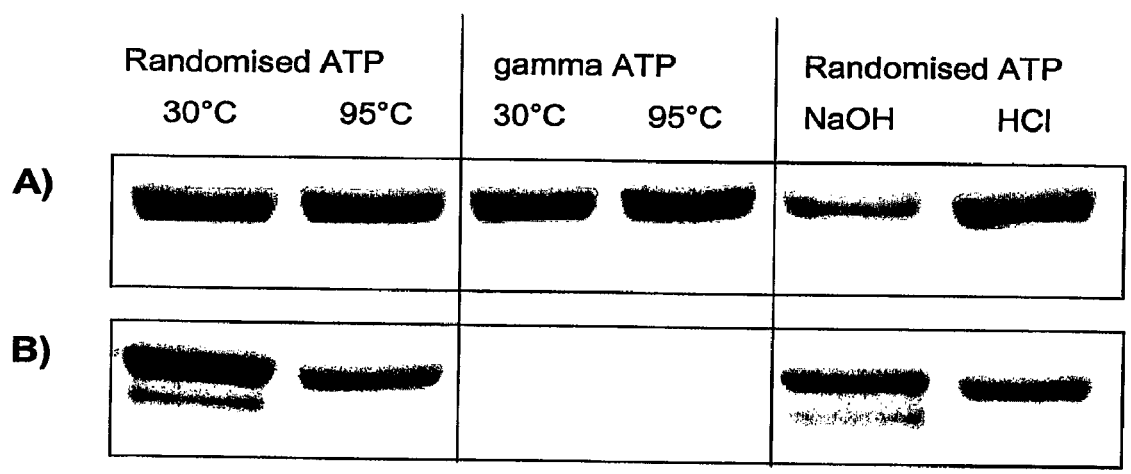
FIG. 5: Demonstration of the autophosphorylation of the OK1 protein.

If recombinantly expressed OK1 protein, as described above, is incubated with ATP specifically labeled with $^{33}$P in the gamma position, then no autophosphorylation can be detected. FIG. 5 A) shows the amount of protein in the respective reaction preparation that can still be demonstrated by means of Western blot analysis after the appropriate incubation steps. FIG. 5 B) shows an autoradiography of protein from the individual reaction preparations. It can be seen that, when ATP specifically labeled in the gamma position is used, no autophosphorylation of the OK1 protein takes place, whereas, when randomised ATP is used, autophosphorylation can be demonstrated. This means that when an OK1 protein is autophosphorylated, the phosphate residue of the beta position of the ATP is covalently bonded to an amino acid of the OK1 protein.

8. Demonstration of the C-Atom Positions, which are Phosphorylated by an OK1 protein, of the Glucose Molecules of Starch a) Manufacture of Phosphorylated Starch Phosphorylated starch was manufactured in accordance with Item 7, General Methods. To do this, 5 mg of non-phosphorylated starch, isolated from leaves of a sex1-3 mutant of *Arabidopsis thaliana* were used in a Preparation A with 25 µg of purified A.t.-OK1 protein and, in a second Preparation B, 5 mg of in vitro phosphorylated starch originally isolated from leaves of a sex1-3 mutant of *Arabidopsis thaliana* were used with 5 µg of purified R1 protein. The reaction was carried out in 500 µl of phosphorylation buffer in each case, which, in each case contained $^{33}$P labeled ATP (ca. 2.5×10$^6$ cpm), by incubating at room temperature for 1 hour under agitation. In addition, a control preparation was used, which contained 5 mg of starch isolated from leaves of a sex1-3 mutant of *Arabidopsis thaliana* and the said phosphorylation buffer, but no protein. The control preparation was treated in exactly the same way as Preparations A and B. The individual reactions were stopped by adding 125 µl 10% SDS in each case and washed with 900 µl in each case, once with 2% SDS, five times with 2 mM ATP and twice with H$_2$O. A centrifugation was carried out after each washing step (2 minutes in an Eppendorf table centrifuge at 13,000 rpm in each case). The starch pellets obtained were resuspended 1 ml H$_2$O in each case and 100 µl of each preparation were mixed after the addition of 3 ml of scintillation cocktail (Ready Safe™, BECKMANN) and subsequently measured with the help of a scintillation counter (LS 6500 Multi-Purpose Scintillation Counter, BECKMANN COULTER™).

The measurement gave the following results:

| Control: | 63 cpm/100 µL | 630 cpm/1000 µL |
|---|---|---|
| Preparation A (OK1): | 1351 cpm/100 µL | 13512 cpm/1000 µL |
| Preparation B (R1): | 3853 cpm/100 µL | 38526 cpm/1000 µL | b) Total Hydrolysis of the P-Starch

The suspensions of Preparations A, B and C obtained in accordance with Step a) were centrifuged again (5 minutes in an Eppendorf table centrifuge at 13,000 rpm), the pellets obtained resuspended in 90 µl 0.7 M HCl (Baker, for analysis) and subsequently incubated for 2 hours at 95° C. Preparations A, B and C were then centrifuged again (5 minutes in an Eppendorf table centrifuge at 13,000 rpm), and the supernatant transferred to a new reaction vessel. Sedimented residues of the preparations were resuspended in 100 ml $H_2O$ in each case and after the addition of 3 ml of scintillation cocktail (Ready Safe™, BECKMANN) were measured with the help of a scintillation counter (LS 6500 Multi-Purpose Scintillation Counter, BECKMANN COULTER™). Significant amounts of radioactivity could not be demonstrated in any of the residues, which means that all the hydrolysis products labeled with radioactive phosphate were located in the supernatant.

This was followed by neutralisation of the individual supernatants containing the hydrolysis products by the addition in each case of 30 µl 2 M NaOH (the amount of NaOH required for neutralisation was tested out in advance on blind samples). The neutralised hydrolysis products were placed on a 10 kDa Microcon filter, which had previously been rinsed twice with 200 µl $H_2O$ in each case, and centrifuged for ca. 25 minutes at 12,000 rpm in an Eppendorf table centrifuge. 10 µl were taken from the filtrate obtained (ca. 120 µl in each case) and, after the addition of 3 ml of scintillation cocktail (Ready Safe™, BECKMANN), were measured with the help of a scintillation counter (LS 6500 Multi-Purpose Scintillation Counter, BECKMANN COULTER™). The determination of the activity present in the individual preparations gave the following results:

| | | | |
|---|---|---|---|
| Preparation A (OK1): | 934 cpm/10 µL | 11,208 cpm/120 µL | 93 cpm/µl |
| Preparation B (R1): | 2518 cpm/10 µL | 30,216 cpm/120 µL | 252 cpm/µl | c) Separation of the Hydrolysis Products

The hydrolysis products obtained in accordance with Step b) were separated by means of HPAE using a Dionex system under the conditions stated above (see General Methods, Item 13 c)). The samples for separating the filtered supernatants of Preparations A and B obtained in accordance with Step b) were composed as follows:

Preparation A (OK1): 43 µl of the supernatant of Preparation A obtained in accordance with Step b) (equivalent to ca. 4,000 cpm), 32 µl $H_2O$, 2.5 µl 2.5 mM glucose-6-phosphate and 2.5 µl 5 mM glucose-3-phosphate (Σ Volume=80 µl).

Preparation B (R1): 16 µl of the supernatant of Preparation B obtained in accordance with Step b) (equivalent to ca. 4,000 cpm), 59 µl $H_2O$, 2.5 µl 2.5 mM glucose-6-phosphate and 2.5 µl 5 mM glucose-3-phosphate (Σ Volume=80 µl).

In each case, 60 µl, containing ca. 3,000 cpm, of the appropriate samples were injected for separation by means of HPAE. The HPAE was carried out in accordance with the conditions specified under Item 23 c). After passing through the HPAE column, the elution buffer was collected in fractions, each of 1 ml. Collection of the fractions was begun 10 minutes after injecting the sample. Based on the signal received from the PAD detector used, the elution of glucose-6-phosphate was assigned to fraction 15 and the elution of glucose-3-phosphate to fraction 17. In each case, 500 µl of the individual fractions were mixed with 3 ml of scintillation cocktail (Ready Safe™, BECKMANN) and subsequently measured with the help of a scintillation counter (LS 6500 Multi-Purpose Scintillation Counter, BECKMANN COULTER™). The following measurements were obtained for the individual fractions:

TABLE 4

Measured amounts of radioactivity [cpm] in individual fractions of hydrolysis products obtained by hydrolysis of starch phosphorylated by means of an OK1 protein or R1 protein.

| | Total cpm per fraction | |
|---|---|---|
| | Preparation A (OK1) | Preparation B (R1) |
| Fr 13 | 8.7 | 3.3 |
| Fr 14 | 13.1 | 32.2 |
| Fr 15 (G6P) | 207.3 | 1952.8 |
| Fr 16 | 399.8 | 112.3 |
| Fr 17 (G3P) | 1749.2 | 801.6 |
| Fr 18 | 196.7 | 17.3 |
| Fr 19 | 6.7 | 18.9 |
| Total | 2581.5 | 2938.3 |
| Deposit | 3000.0 | 3000.0 |
| Recovery | 86.0% | 97.9% |

The results are also shown graphically in FIG. 5.

After phosphorylation of starch catalysed by R1 protein, ca. 66% of the radioactively labeled phosphate, referred to the total measured radioactive phosphate in the analysed fractions, eluted after hydrolysing the starch with the fraction, which contained glucose-6-phosphate as standard, and ca. 27% with the fraction, which contained glucose-3-phosphate as standard. After phosphorylation of starch catalysed by OK1 protein, ca. 67% of the radioactively labeled phosphate, referred to the total measured radioactive phosphate in the analysed fractions, eluted after hydrolysing the starch with the fraction, which contained glucose-3-phosphate as standard, and ca. 8% with the fraction, which contained glucose-6-phosphate as standard. From this, it can be concluded that glucose molecules of the starch of R1 proteins are preferably phosphorylated in the C-6 position, whereas, from OK1 proteins, glucose molecules of the starch are preferably phosphorylated in the C-3 position.

9. Identification of an OK1 Protein in Rice

Using the methods described under Items 1 to 13, General Methods, it was also possible to identify a protein from *Oryza sativa* (variety M202), which transfers a phosphate residue from ATP to P-starch. The protein was designated as O.s.-OK1. Non-phosphorylated starch is not used by the O.s.-OK1 protein as a substrate, i.e. the O.s.-OK1 protein also does not need P-starch as a substrate. The nucleic acid sequence defining the identified O.s.-OK1 protein is shown under SEQ ID NO 3 and the amino acid sequence coding the O.s.-OK1 protein is shown under SEQ ID NO. 4. The amino acid sequence coding the O.s.-OK1 protein shown under SEQ ID NO 4 has an identity of 57% with the amino acid sequence coding the A.t.-OK1 protein shown under SEQ ID NO 2. The nucleic acid sequence coding the O.s.-OK1 protein shown under SEQ ID NO 3 has an identity of 61% with the nucleic acid sequence coding the A.t.-OK1 protein shown under SEQ ID NO 1.

Manufacture of the plasmid pMI50 containing the nucleic acid sequence coding an OK1 protein from *Oryza sativa*

The vector pMI50 contains a DNA fragment, which codes the complete OK1 protein from rice of the variety M202.

The amplification of the DNA from rice was carried out in five sub-steps.

The part of the open reading frame from position 11 to position 288 of the sequence specified under SEQ DIE NO 3 was amplified with the help of reverse transcriptase and polymerase chain reaction using the synthetic oligonucleotides Os_ok1-R9 (GGAACCGATAATGCCTACATGCTC) and Os_ok1-F6 (AAAACTCGAGGAGGATCAAT-GACGTCGCTGCGGCCCCTC) as a primer on RNA of immature rice seeds. The amplified DNA fragment was cloned in the vector pCR2.1 (Invitrogen catalogue number K2020-20). The plasmid obtained was designated as pML123.

The part of the open reading frame from position 250 to position 949 of the sequence specified under SEQ DIE NO 3 was amplified with the help of reverse transcriptase and polymerase chain reaction using the synthetic oligonucleotides Os_ok1-F4 (CCAGGTTAAGTTTGGTGAGCA) and Os_ok1-R6 (CAAAGCACGATATCTGACCTGT) as a primer on RNA of immature rice seeds. The amplified DNA fragment was cloned in the vector pCR2.1 (Invitrogen catalogue number K2020-20). The plasmid obtained was designated as pML120.

The part of the open reading frame from position 839 to position 1761 of the sequence specified under SEQ DIE NO 3 was amplified with the help of reverse transcriptase and polymerase chain reaction using the synthetic oligonucleotides Os_ok1-F7 (TTGTTCGCGGGATATTGTCAGA) and Os_ok1-R7 (GACAAGGGCATCAAGAGTAGTATC) as a primer on RNA of immature rice seeds. The amplified DNA fragment was cloned in the vector pCR2.1 (Invitrogen catalogue number K2020-20). The plasmid obtained was designated as pML121.

The part of the open reading frame from position 1571 to position 3241 of the sequence specified under SEQ DIE NO 3 was amplified with the help of reverse transcriptase and polymerase chain reaction using the synthetic oligonucleotides Os_ok1-F8 (ATGATGCGCCTGATAATGCT) and Os_ok1-R4 (GGCAAACAGTATGAAGCACGA) as a primer on RNA of immature rice seeds. The amplified DNA fragment was cloned in the vector pCR2.1 (Invitrogen catalogue number K2020-20). The plasmid obtained was designated as pML119.

The part of the open reading frame from position 2777 to position 3621 was amplified with the help of polymerase chain reaction using the synthetic oligonucleotides Os_ok1-F3 (CATTTGGATCAATGGAGGATG) and Os_ok1-R2 (CTATGGCTGTGGCCTGCTTTGCA) as a primer on genomic DNA of rice. The amplified DNA fragment was cloned in the vector pCR2.1 (Invitrogen catalogue number K2020-20). The plasmid obtained was designated as pML122.

The cloning together of the sub-parts of the open reading frame of OK1 was carried out as follows.

A 700 base pair along ApaI fragment of pML120, containing part of the open reading frame of OK1, was cloned in the ApaI site of pML121. The plasmid obtained was designated as pMI47.

A 960 base pair long fragment containing the areas of vectors from pML120 and pML123 coding for OK1 was amplified by means of polymerase chain reaction. In doing so, the primers Os_ok1-F4 (see above) and Os_ok1-R9 (see above), each in a concentration of 50 nm, and the primers Os_ok1-F6 and Os_ok1-R6, each in a concentration of 500 nm, were used. The amplified DNA fragment was cloned in the vector pCR2.1 (Invitrogen catalogue number K2020-20). The plasmid obtained was designated as pMI44.

An 845 base pair long fragment of pML122 was reamplified for introducing a XhoI site after the stop codon with the primers Os_ok1-F3 (see above) and Os_ok1-R2Xho (AAAACTCGAGCTATGGCTGTGGCCTGCTTTGCA) and cloned in the vector pCR2.1 (Invitrogen catalogue number K2020-20). The plasmid obtained was designated as t pMI45.

A 1671 base pair long fragment containing part of the open reading frame of OK1 was obtained from pML119 by digesting with the restriction enzymes SpeI and PstI. The fragment was cloned in pBluescript II SK+ (Genbank Acc.: X52328). The plasmid obtained was designated as pMI46.

A 1706 base pair long fragment containing part of the open reading frame of OK1 was excised with the restriction enzymes SpeI and XhoI from pMI46 and cloned in the vector pMI45, which had been excised with the same restriction enzymes. The plasmid obtained was designated as pMI47.

A 146 base pair long fragment containing part of the open reading frame of OK1 was excised with the restriction enzymes AflII/NotI from pMI43 and cloned in the vector pMI44, which had been excised with the same restriction enzymes. The plasmid obtained was designated as pMI49.

A 1657 base pair long fragment containing part of the open reading frame of OK1 was excised with the restriction enzymes NotI and NarI from the vector pMI49 and cloned in the vector pMI47, which had been excised with the same restriction enzymes. The plasmid obtained was designated as pMI50 and contains the whole coding region of the OK1 protein identified in rice.

10. Manufacture of an Antibody, which Specifically Detects an OK1 Protein

As an antigen, ca. 100 μg of purified A.t.-OK1 protein was separated by means of SDS gel electrophoresis, the protein bands containing the A.t.-OK1 protein excised and sent to the company EUROGENTEC S.A. (Belgium), which carried out the manufacture of the antibody under contract. Next, the preimmune serums of rabbits were investigated to see whether they would already detect a protein from an A. t. total extract before immunisation with recombinant OK1. The preimmune serums of two rabbits detected no proteins in the range 100-150 kDa and were thus chosen for immunisation. 4 injections of 100 μg of protein (Tag 0, 14, 28, 56) were given to each rabbit. 4 blood samples were taken from each rabbit: (Tag 38, Tag 66, Tag 87 and the final bleeding). Serum, obtained after the first bleeding, already showed a specific reaction with OK1 antigen in Western blot. However, in all further tests, the last bleeding of a rabbit was used 11. Manufacture of Transgenic Rice Plants, which have a Reduced Activity of an OK1 Protein a) Manufacture of a Construct for Inhibiting the OK1 Protein in Rice by Means of RNAi Technology The plasmid pML125, which was used for the transformation of rice plants, was obtained by specific recombination of the plasmids pML124 and pIR115 using the Gateway™ cloning system (Invitrogen).

pML124 was obtained, by cloning a 359 base pair long DNA fragment of pML119 (see above, Example 9), containing part of the open reading frame, which codes for the OK1 protein from rice, in the vector pENTR-1A (Invitrogen, product number 11813-011) excised with EcoRI.

The plasmid pIR115 is based on the plasmids pGSV71, pIR94, containing the promoter of the globulin gene from rice, pIR87 containing the intron 1 of the gene coding for alcohol dehydrogenase from maize and the "Gateway reading frame cassette A" (RfA) from the "vector conversion system" (Invitrogen product number 11828-019).

pGSV71 is a derivative of the plasmid pGSV7, which derives from the intermediate vector pGSV1. pGSV1 constitutes a derivative of pGSC1700, the construction of which has been described by Cornelissen and Vanderwiele (Nucleic Acid Research 17, (1989), 19-25). pGSV1 was obtained from pGSC1700 by deletion of the carbenicillin resistance gene and deletion of the T-DNA sequences of the TL-DNA region of the plasmid pTiB6S3.

pGSV7 contains the replication origin of the plasmid pBR322 (Bolivar et al., Gene 2, (1977), 95-113) as well as the replication origin of the *Pseudomonas* plasmid pVS1 (Itoh et al., Plasmid 11, (1984), 206). pGSV7 also contains the selectable marker gene aadA, from the transposon Tn1331 from *Klebsiella pneumoniae*, which gives resistance against the antibiotics spectinomycin and streptomycin (Tolmasky, Plasmid 24 (3), (1990), 218-226; Tolmasky and Crosa, Plasmid 29(1), (1993), 31-40).

The plasmid pGSV71 was obtained by cloning a chimeric bar gene between the border regions of pGSV7. The chimeric bar gene contains the promoter sequence of the cauliflower mosaic virus for initiating the transcription (Odell et al., Nature 313, (1985), 180), the bar gene from *Streptomyces hygroscopicus* (Thompson et al., Embo J. 6, (1987), 2519-2523) and the 3'-untranslated area of the nopaline synthase gene of the T-DNA of pTiT37 for terminating the transcription and polyadenylation. The bar gene provides tolerance against the herbicide glufosinate ammonium.

The plasmid pIR94 was obtained by amplifying the promoter of the globulin gene from rice by means of a polymerase chain reaction (30×20 sec 94° C., 20 sec 62° C., 1 min 68° C., 4 mM $Mg_2SO_4$) with the primers glb1-F2 (AAAA-CAATTGGCGCCTGGAGGGAGGAGA) and glb1-R1 (AAAACAATTGATGATCAATCAGACAATCACTAGAA) on the genomic DNA of rice of the variety M202 with High Fidelity Taq Polymerase (Invitrogen, catalogue number 11304-011) and cloned in pCR2.1 (Invitrogen catalogue number K2020-20).

The plasmid pIR87 was obtained by amplifying the intron 1 of the gene coding for alcohol hydrogenase from maize with the primers Adh(i)-1 (TTTTCTCGAGGTCCGCCT-TGTTTCTCCT) and Adh(i)-2 (TTTTCTCGAGCTG-CACGGGTCCAGGA) on the genomic DNA of maize. The product of the polymerase chain reaction (30×30 sec 94° C., 30 sec 59° C., 1 min 72° C., 2.5 mM $MgCl_2$) was digested with the restriction enzyme XhoI and cloned in the vector pBluescript II SK+ (Genbank # X52328), which had been excised with the same enzyme.

The plasmid pIR115 was obtained by cloning a synthetic piece of DNA consisting of the two oligonucleotides X1 (TGCAGGCTGCAGAGCTCCTAGGCTC-GAGTTAACACTAGTAAGCTTAATTAAGAT ATCATT-TAC) and X2 (AATTGTAAATGATATCTTAATTAAGCT-TACTAGTGTTAACTCGAGCCTAGGAGCT CTGCAGCCTGCA) in the vector pGSV71 excised with SdaI and MunI.

The plasmid pIR115 obtained was excised with SdaI, the protruding 3'-ends smoothed with T4 DNA polymerase and a HindIII/SphI fragment from pBinAR (Höfgen and Willmitzer, 1990, Plant Science 66, 221-230) with a size of 197 base pairs, smoothed by means of T4 DNA polymerase and containing the termination signal of the octopine synthase gene from *Agrobacterium tumefaciens*, was inserted. The plasmid obtained was designated as pIR96. A 986 base pair long DNA fragment from pIR94, containing the promoter of the globulin gene from rice, was cloned in the vector pIR96. The plasmid obtained was designated as pIR103.

The plasmid pIR107 was obtained by cloning the "RfA cassette" (see above) in the plasmid pIR103 excised with the restriction enzyme EcoRV.

A 540 base pair long fragment containing the intron 1 of the gene coding for alcohol hydrogenase from maize was excised from the plasmid pIR87 with the restriction enzyme XhoI and cloned in the plasmid pIR107, likewise excised with XhoI. The plasmid obtained was designated as pIR114. The plasmid pIR115 was obtained by cloning the "RfA cassette" (see above) in the plasmid pIR114 excised with Ecl136II. The plasmid obtained was designated as pML125.

b) Transformation of Rice Plants

Rice plants (variety M202) were transformed by means of *Agrobacterium* (containing the plasmid pML125) using the method described by Hiei et al. (1994, Plant Journal 6(2), 271-282).

c) Analysis of the Transgenic Rice Plants

With the help of quantitative RT PCR analysis, it was possible to identify rice plants, which had a reduced amount of mRNA coding OK1 protein.

12. Manufacture of Transgenic Potato Plants, which have a Reduced Activity of an OK1 Protein a) Manufacture of the Plasmid pBinb33-Hyg Starting from the plasmid pBinB33, the EcoRI-HindIII fragment including the B33 promoter, a part of the polylinker, and the ocs terminator were excised and spliced into the correspondingly excised vector pBIB-Hyg (Becker, 1990, Nucl. Acids Res. 18, 203).

The plasmid pBinB33 was obtained by splicing the promoter of the patatin gene B33 from *Solanum tuberosum* (Rocha-Sosa et al., 1989) as a DraI fragment (nucleotide-1512-+14) into the vector pUC19 excised with SstI, the ends of which had been smoothed with the help of the T4 DNA polymerase. This resulted in the plasmid pUC19-B33. The B33 promoter was excised from this plasmid with EcoRI and SmaI and cloneed into the correspondingly excised vector pBinAR (Höfgen and Willmitzer, 1990, Plant Science 66, 221-230). This resulted in the plant expression vector pBinB33.

b) Manufacture of the Vector A.t.-OK1-pBinB33-Hyg

The coding sequence of the A.t.-OK1 protein was excised with the restriction endonucleases Bsp120I and SalI from the plasmid OK1-pGEM and cloned into the vector pBinB33-Hyg excised with SmaI and SalI. The plasmid obtained was designated as A.t.-OK1-pBinB33-Hyg.

c) Transformation of Potato Plants

*Agrobacterium tumefaciens* (strain GV2260) was transformed with the plasmid A.t.-OK1-pBinB33-Hyg. Subsequently, potato plants of the variety Désirée were transformed with the help of the *agrobacteria* containing the plasma A.t.-OK1-pBinB33-Hyg in accordance with the method described by Rocha-Sosa et al. (EMBO J. 8, (1989), 23-29), and plants regenerated.

d) Analysis of the Transgenic Potato Plants and the Starch Synthesised from these By means of quantitative RT PCR analysis, it was possible to identify plants, which had a reduced activity of the endogenous OK1 protein in the tubers.

A Western blot analysis, which was carried out with the antibodies described under Example 10, confirmed that plants, which had a reduced amount of mRNA of the endogenous OK1 proteins, also had a reduced amount of OK1 protein compared with wild type plants that had not been transformed.

Plants, which had a reduced amount of OK1 protein and a reduced amount of mRNA coding OK1 protein compared with corresponding wild type plants, were again raised in the greenhouse. Starch, which was isolated from the tubers of these plants, showed a reduced content of phosphate covalently bonded to the starch concerned.

13. Analysis of *Arabidopsis thaliana* Plants, which have a Reduced Activity of an OK1 Protein T-DNA insertion mutants of *Arabidopsis thaliana* (obtainable from Salk Institute Genomic Analysis Laboratory, 10010 N. Torrey Pines Road, La Jolla, Calif. 92037, http://signal.salk.edu/under the ACC. No.: Salk__110814, alias N610814), which were homozygotic with regard to the insertion in the OK1 gene, were raised under the following conditions:

| | |
|---|---|
| Light phase: | 16 hours, 20° C. |
| Dark phase: | 8 hours, 16° C. |

Shortly before the onset of bloom formation, the plants were cultivated with a light phase of 12 hours at 20° C. and a dark phase of 12 hours at 17° C.

From the seeds obtained from the mutant line (Salk__110814), plants were cultivated for analysis from 3 different seeds of the original seed crop (Salk__110814-1, Salk__110814-2, Salk__110814-3).

At the end of the dark phase, 10 leaves were removed from each of 6 wild type plants and bleached in 70% ethanol at 50° C. In addition, 6 leaves were removed from each of 4 different plants of the mutant lines Salk__110814-1, Salk__110814-2 and Salk__110814-3 in each case, which in each case were homozygotic with regard to the T-DNA insertion in an OK1 gene, and bleached in 70% ethanol at 50° C. The leaves were then incubated for 10 minutes in Lugol's solution before excess Lugol's solution was rinsed from the leaves with tap water. None of the leaves of wild type plants showed any colouring with Lugol's solution. On the other hand, all leaves of the mutant lines Salk__110814-1, Salk__110814-2 and Salk__110814-3 exhibited a dark-brown or a black colouration. The mutant lines therefore show a high starch phenotype in comparison with the wild type plants. During cultivation, no difference with regard to the growth could be established between the mutant lines and the wild type plants.

Genetically modified *Arabidopsis thaliana* plants, which were transformed with an RNAi construct containing "inverted repeats" of the coding region of an OK1 gene under the control of the 35S promoter, were analysed with the help of Western blot analysis using the antibodies described in Example 10. It was possible to identify several independent lines, which had a reduced amount of OK1 protein in comparison with wild type plants. These lines were cultivated under the cultivation conditions specified in Example 13. At the end of the dark phase (12 hours at 17° C.), 5 leaves were removed from each of the individual lines, bleached in ethanol and stained with Lugol's solution. All plants showed a high starch phenotype compared with corresponding wild type plants. During cultivation, no difference with regard to the growth could be established between the genetically modified plants and the wild type plants. The plants genetically modified by means of RNAi technology therefore exhibited the same characteristics as the mutant lines Salk__110814-1, Salk__110814-2 and Salk__110814-3.

Figures 7, 8:
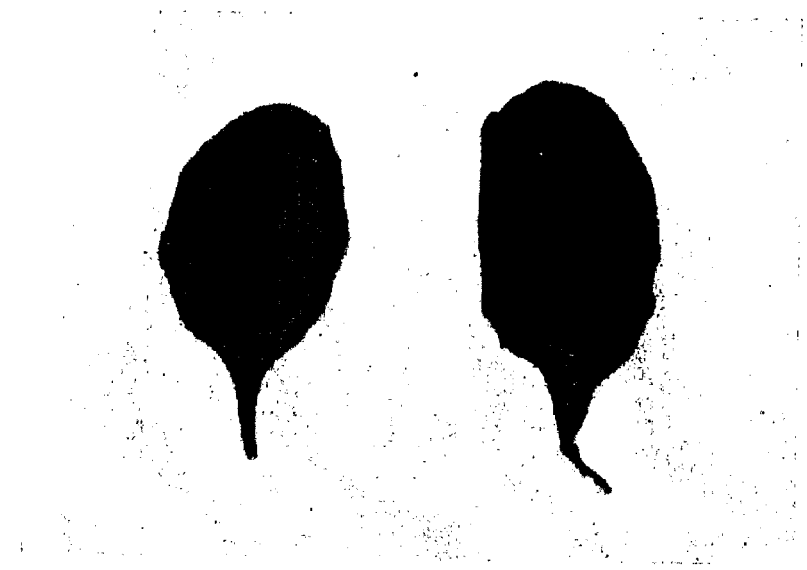
FIG. 7: Leaf, stained with Lugol's solution, of a mutant, which has a reduced activity of an OK1 protein in comparison with a leaf of a wild type plant.
FIG. 8: Western blot analysis of plants, which have a reduced amount of OK1 protein. The plant lines A.t.-alpha-OK1-1, A.t.-alpha-OK1-2, A.t.-alpha-OK1-3, A.t.-alpha-OK1-4 and A.t.-alpha-OK1-5 were genetically modified with the help of RNAi technology. WT indicates wild type plants.

Four *Arabidopsis thaliana* plants in each case of the lines A.t.-alpha-OK1-1, A.t.-alpha-OK1-2, A.t.-alpha-OK1-3, A.t.-alpha-OK1-4 and A.t.-alpha-OK1-5 resulting from independent transformation events, in which the amount of OK1 protein is reduced by means of RNAi technology, were examined at different times for their leaf starch content. The reduction in the amount of OK1 protein in the respective lines was demonstrated by means of Western blot analysis (see FIG. 8). The leaf starch content of the individual lines was determined with the help of the Boehringer Mannheim starch kit (Product No.: 0207748). To do this, all the leaves of four plants of the individual lines in each case were harvested and the leaves homogenised by crushing in a mortar. 40 mg to 60 mg of the homogenised leaf material was washed twice with 80% ethanol in each case and the supernatant discarded. After again washing in 1 ml of water, the remaining material that was not soluble in ethanol was freeze-dried, subsequently dissolved in 0.5 ml 0.2M KOH at 95° C. for 1 h, and the solution obtained adjusted to a pH value of 7 with 88 μL 1 M acetic acid. 25 μl of the solution obtained in each case were mixed with 50 μl amyloglucosidase solution (Boehringer Mannheim starch kit, Product No.: 0207748), to which 1 unit of alpha-amylase (from *Bacillus amyloliquefaciens*, Boehringer, Prod-No. 161764) was added, and incubated for 1 h at 55° C. 20 μl of the solution treated with amyloglucosidase and alpha-amylase were subsequently used for determining the glucose by means of an enzymatically coupled photometric test (see Boehringer Ingelheim product information sheet for the determination of native starch, Product No.: 0207748). In parallel with the transgenic lines, the starch content in leaves of *Arabidopsis thaliana* wild type plants (ecotype Columbia) was also determined. The wild type plants and the transgenic plants were cultivated under identical conditions: 12 hours light phase followed by 12 hours dark phase.

In each case, leaves of the respective transgenic plant lines and wild type plants were harvested ca. 4.5 weeks after seed germination at the end of a dark phase, at the end of a light phase and at the end of a second dark phase, which directly followed the light phase. Two independent extracts were produced for each of the transgenic plant lines, from which two measurements of the starch content were carried out in each case. Four independent extracts were produced for each of the wild type plants, from which two measurements of the starch content were carried out in each case. The determination of the leaf starch content gave the following results:

TABLE 4

Amount of leaf starch in *Arabidopsis thaliana* plants, in which the amount of OK1 protein is reduced with the help of RNAi technology.

| | Line | Starch content (mg/g FW) | Standard deviation* |
|---|---|---|---|
| End of dark phase 1 | A.t.-alpha-OK1-1 | 4.09 | 0.55 |
| | A.t.-alpha-OK1-2 | 4.93 | 0.94 |
| | A.t.-alpha-OK1-3 | 5.59 | 0.52 |
| | A.t.-alpha-OK1-4 | 6.36 | 0.87 |
| | A.t.-alpha-OK1-5 | 1.49 | 0.99 |
| | Wild type | 0.78 | 0.14 |
| End of light phase | A.t.-alpha-OK1-1 | 9.30 | 0.96 |
| | A.t.-alpha-OK1-2 | 9.86 | 1.45 |
| | A.t.-alpha-OK1-3 | 11.68 | 1.60 |
| | A.t.-alpha-OK1-4 | 9.53 | 1.25 |
| | A.t.-alpha-OK1-5 | 6.61 | 0.71 |
| | Wild type | 5.61 | 0.72 |

TABLE 4-continued

Amount of leaf starch in *Arabidopsis thaliana* plants, in which the amount of OK1 protein is reduced with the help of RNAi technology.

|  | Line | Starch content (mg/g FW) | Standard deviation* |
|---|---|---|---|
| End of dark phase 2 | A.t.-alpha-OK1-1 | 3.92 | 0.83 |
|  | A.t.-alpha-OK1-2 | 4.35 | 1.07 |
|  | A.t.-alpha-OK1-3 | 6.00 | 0.63 |
|  | A.t.-alpha-OK1-4 | 5.34 | 1.35 |
|  | A.t.-alpha-OK1-5 | 1.46 | 0.56 |
|  | Wild type | 0.62 | 0.18 |

*Standard deviation with the general formula: Root $[(n\Sigma x^2 - (\Sigma x)^2)/n(n-1)]$

14. Analysis of Starch Isolated from Plants, which have a Reduced Activity of an OK1 Protein Starch was isolated from leaves of the plants described in Example 13 and hydrolysed in accordance with the method described under General Methods, Item 13, and subsequently separated by means of HPAE analysis. The areas of the separated signals obtained for C-3 phosphate and C-6 phosphate by means of HPAE analysis were calculated (software: Chromelion 6.20 from Dionex, USA) and the values obtained were compared with one another. The ratio of C-6 phosphate to C-3 phosphate in wild type plants was 2.1. On the other hand, in the plants described in Example 13, in which the activity of an OK1 protein was reduced by means of RNAi technology, the C-6 phosphate to C-3 phosphate ratio, which was determined with the help of the analysis of starch isolated from the lines A.t.-alpha-OK1-1, A.t.-alpha-OK1-2, A.t.-alpha-OK1-3, A.t.-alpha-OK1-4 and A.t.-alpha-OK1-5, was on average 2.5. The analysis of starch of the line A.t.-alpha-OK1-5 gave the lowest value for the ratio of C-6 phosphate to C-3 phosphate (ratio of 2.2), and starch of the line A.t.-alpha-OK1-1 gave the highest value (ratio 2.7).

Starch isolated from leaves of the mutants described in Example 13, which have a reduced activity of an OK1 protein, also exhibited an increase in the C-6 phosphate to C-3 phosphate ratio in the starches concerned.

The absolute amounts of C-6 phosphate and C-3 phosphate bonded to the starch in wild type plants that had not been genetically modified compared with C-6 phosphate and C-3 phosphate bonded to the starch in the genetically modified plants described in Example 13, in which the activity of an OK1 protein was reduced by means of RNAi technology, showed that the absolute content of C-3 phosphate bonded to the starch had similar values for wild type plants and genetically modified plants. However, the absolute value that was obtained for C-6 phosphate bonded to the starch was significantly increased in the plants genetically modified by means of RNAi technology compared with that in starch isolated from wild type plants.

The invention claimed is:

1. A modified starch obtained from a genetically modified plant, or propagation material or a harvestable part therefrom, comprising one or more genetically modified plant cells, said genetically modified plant cell having a reduced activity of at least one OK1 protein in comparison with corresponding wild type plant cells that have not been genetically modified, wherein the modified starch has a ratio of C-6 phosphate to C-3 phosphate which is increased compared to starch isolated from wild type plants.

2. A method for manufacturing a modified starch comprising extracting the starch from a plant cell having a reduced activity of at least one OK1 protein in comparison with corresponding wild type plant cells that have not been genetically modified, wherein the modified starch has a ratio of C-6 phosphate to C-3 phosphate which is increased compared to starch isolated from wild type plants.

3. A method for manufacturing a modified starch comprising extracting the starch from a plant and/or from a starch-storing part thereof comprising one or more genetically modified plant cells, said genetically modified plant cell having a reduced activity of at least one OK1 protein in comparison with corresponding wild type plant cells that have not been genetically modified, wherein the modified starch has a ratio of C-6 phosphate to C-3 phosphate which is increased compared to starch isolated from wild type plants.

4. A method for manufacturing a modified starch comprising extracting the starch from a harvestable plant part comprising one or more genetically modified plant cells, said genetically modified plant cell having a reduced activity of at least one OK1 protein in comparison with corresponding wild type plant cells that have not been genetically modified, wherein the modified starch has a ratio of C-6 phosphate to C-3 phosphate which is increased compared to starch isolated from wild type plants.

5. A modified starch obtained by a method according to claim 2.

6. A method for manufacturing a derived starch, comprising deriving a modified starch according to claim 5.

7. A derived starch obtained by a method according to claim 6.

* * * * *